US011241491B2

(12) United States Patent
Baric et al.

(10) Patent No.: US 11,241,491 B2
(45) Date of Patent: Feb. 8, 2022

(54) METHODS AND COMPOSITIONS FOR DENGUE VIRUS SEROTYPE 4 EPITOPES

(71) Applicant: The University of North Carolina at Chapel Hill, Chapel Hill, NC (US)

(72) Inventors: Ralph Baric, Haw River, NC (US); Matthew Begley, Durham, NC (US); Douglas Widman, Newton Center, MA (US); Aravinda Desilva, Chapel Hill, NC (US); Usha Nivarthi, Morrisville, NC (US); Boyd Yount, Hillsborough, NC (US); Ellen Young, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/615,350

(22) PCT Filed: May 23, 2018

(86) PCT No.: PCT/US2018/034151
§ 371 (c)(1),
(2) Date: Nov. 20, 2019

(87) PCT Pub. No.: WO2018/217906
PCT Pub. Date: Nov. 29, 2018

(65) Prior Publication Data
US 2020/0155663 A1    May 21, 2020

Related U.S. Application Data

(60) Provisional application No. 62/561,942, filed on Sep. 22, 2017, provisional application No. 62/510,133, filed on May 23, 2017.

(51) Int. Cl.
| | |
|---|---|
| *A61K 39/12* | (2006.01) |
| *A61P 31/14* | (2006.01) |
| *C07K 14/005* | (2006.01) |
| *C12N 7/00* | (2006.01) |
| *A61K 39/00* | (2006.01) |

(52) U.S. Cl.
CPC ............ *A61K 39/12* (2013.01); *A61P 31/14* (2018.01); *C07K 14/005* (2013.01); *C12N 7/00* (2013.01); *A61K 2039/5254* (2013.01); *A61K 2039/575* (2013.01); *A61K 2039/70* (2013.01); *C12N 2770/24122* (2013.01); *C12N 2770/24123* (2013.01); *C12N 2770/24134* (2013.01)

(58) Field of Classification Search
None
See application file for complete search history.

(56) References Cited

U.S. PATENT DOCUMENTS

| | | |
|---|---|---|
| 2013/0216575 A1 | 8/2013 | Coller et al. |
| 2016/0151477 A1 | 6/2016 | Bett et al. |
| 2016/0257719 A1 | 9/2016 | Messer et al. |

OTHER PUBLICATIONS

CDC website, https://www.cdc.gov/dengue/prevention/dengue-vaccine.html, Dengue Vaccine, accessed on Jul. 2, 2021.*
CDC website, https://www.cdc.gov/dengue/prevention/index.html, Dengue virus prevention, accessed on Jul. 2, 2021.*
GenBank Accession# ABA61185.1, polyprotein [Dengue virus 2], 2006.*
Amanna et al. "Duration of Humoral Immunity to Common Viral and Vaccine Antigens" New England Journal of Medicine, 357(19):1903-1915 (2007).
Beltramello et al. "The Human Immune Response to Dengue Virus Is Dominated by Highly Cross-Reactive Antibodies Endowed with Neutralizing and Enhancing Activity" Cell Host Microbe, 8(3):271-283 (2010).
Bhatt et al. "The global distribution and burden of dengue" Nature, 496(7446):504-507 (2013).
Cockburn et al. "Structural insights into the neutralization mechanism of a higher primate antibody against dengue virus" The EMBO Journal, 31:767-779 (2012).
De Alwis et al. "Identification of human neutralizing antibodies that bind to complex epitopes on dengue virions" PNAS, 109(19):7439-7444 (2012).
De Alwis et al. "In-Depth Analysis of the Antibody Response of Individuals Exposed to Primary Dengue Virus Infection" PLoS Neglected Tropical Diseases, 5(6):e1188 (2011).
Dejnirattisai et al. "Cross-Reacting Antibodies Enhance Dengue Virus Infection in Humans" Science, 328(5979):745-748 (2010).
Dejnirattisai et al. "A new class of highly potent, broadly neutralizing antibodies isolated from viremic patients infected with dengue virus" Nature Immunology, 16(2):170-177 (2015).
Dowd et al. "A Dynamic Landscape for Antibody Binding Modulates Antibody-Mediated Neutralization of West Nile Virus" PLoS Pathogens, 7(6):e1002111 (2011).
Durbin et al. "Attenuation and Immunogenicity in Humans of a Live Dengue Virus TYPE-4 Vaccine Candidate with a 30 Nucleotide Deletion in its 3'-Untranslated Region" American Journal of Tropical Medicine and Hygiene, 65(5):405-413 (2001).
Durbin et al. "Development and clinical evaluation of multiple investigational monovalent DENV vaccines to identify components for inclusion in a live attenuated tetravalent DENV vaccine" Vaccine, 29(42):7242-7250 (2011).
Fibriansah et al. "A highly potent human antibody neutralizes dengue virus serotype 3 by binding across three surface proteins" Nature Communications, 6(6341), 10 pages (2015).

(Continued)

*Primary Examiner* — Benjamin P Blumel
(74) *Attorney, Agent, or Firm* — Myers Bigel, P.A.

(57) ABSTRACT

The present invention provides compositions and methods of use comprising a chimeric dengue virus E glycoprotein comprising a dengue virus E glycoprotein backbone, which comprises amino acid substitutions that introduce a dengue virus E glycoprotein epitope from a dengue virus serotype that is different from the dengue virus serotype of the dengue virus E glycoprotein backbone.

13 Claims, 15 Drawing Sheets

Specification includes a Sequence Listing.

(56) References Cited

OTHER PUBLICATIONS

Fibriansah et al. "A potent anti-dengue human antibody preferentially recognizes the conformation of E protein monomers assembled on the virus surface" EMBO Molecular Medicine, 6(3):358-371 (2014).
Fibriansah et al. "Cryo-EM structure of an antibody that neutralizes dengue virus type 2 by locking E protein dimers" Science, 349(6243):88-91 (2015).
Friberg et al. "Analysis of Human Monoclonal Antibodies Generated by Dengue Virus-Specific Memory B Cells" Viral Immunology, 25(5):348-359 (2012).
Gallichotte et al. "A New Quaternary Structure Epitope on Dengue Virus Serotype 2 Is the Target of Durable Type-Specific Neutralizing Antibodies" mBio, 6(5), 8 pages (2015).
Gallichotte et al. "Epitope Addition and Ablation via Manipulation of a Dengue Virus Serotype 1 Infectious Clone" mSphere, 2(1):e00380-16 (2017).
GenBank Accession No. AAB70694 "polyprotein [Dengue virus 1]" NCBI (4 pages) (Sep. 19, 1997).
GenBank Accession No. ADA00411 "polyprotein precursor [Dengue virus 2]" NCBI (4 pages) (Aug. 16, 2011).
GenBank Accession No. AFI55000 "polyprotein [Dengue virus 3]" NCBI (4 pages) (Apr. 30, 2012).
GenBank Accession No. AHN50410 "polyprotein [Dengue virus 4]" NCBI (5 pages) (Mar. 31, 2014).
GenBank Accession No. DQ211652 "West Nile virus strain NY99, complete genome" NCBI (5 pages) (Jun. 7, 2006).
GenBank Accession No. FJ882599 "Dengue virus 4 isolate DENV-4/US/BID-V2446/1999, complete genome" NCBI (5 pages) (May 5, 2009).
GenBank Accession No. GU289914 "Dengue virus 2 strain S16803, complete genome" NCBI (5 pages) (Aug. 16, 2011).
GenBank Accession No. JF262780 "Dengue virus 4 isolate P73-1120, complete genome" NCBI (5 pages) (Jan. 8, 2012).
GenBank Accession No. JQ411814 "Dengue virus 3 isolate UNC3001, complete genome" NCBI (5 pages) (Apr. 30, 2012).
GenBank Accession No. JX503529 "Yellow fever virus strain YF/Vaccine/USA/Sanofi-Pasteur-17D-204/UF795AA/YFVax, complete genome" NCBI (5 pages) (Sep. 16, 2012).
GenBank Accession No. KC963424 "Dengue virus 4 strain TVP-376 polyprotein gene, partial cds" NCBI (2 pages) (Aug. 3, 2013).
GenBank Accession No. KF543272 "Dengue virus 4 isolate U0811386 polyprotein gene, partial cds" NCBI (2 pages) (Nov. 24, 2013).
GenBank Accession No. KJ160504 "Dengue virus 4 isolate rDENV4, complete genome" NCBI (5 pages) (Mar. 31, 2014).
GenBank Accession No. NC_001474 "Dengue virus 2, complete genome" NCBI (7 pages) (Jul. 11, 2019).
GenBank Accession No. U14163 "Japanese encephalitis virus SA14 polyprotein mRNA, complete cds" NCBI (5 pages) (Sep. 13, 1994).
GenBank Accession No. U88535 "Dengue virus type 1 clone WestPac, complete genome" NCBI (5 pages) (Sep. 19, 1997).
Halstead "Dengue" The Lancet, 370(9599):1644-1652 (2007) (Abstract).
Halstead "Neutralization and Antibody-Dependent Enhancement of Dengue Viruses" Advances in Virus Research, 60:421-467 (2003) (Abstract).
Holmes et al. "The origin, emergence and evolutionary genetics of dengue virus" Infection, Genetics and Evolution, 3(1):19-28 (2003) (Abstract).
Imrie et al. "Antibody to Dengue 1 Detected More Than 60 Years after Infection" Viral Immunology, 20(4): 672-675 (2007).
International Preliminary Report on Patentability corresponding to International Patent Application No. PCT/US2018/034151 (6 pages) (dated Dec. 5, 2019).
Kanakaratne et al. "Severe Dengue Epidemics in Sri Lanka, 2003-2006" Emerging Infectious Diseases, 15(2):192-199 (2009).
Klein et al. "Structure of a Dengue Virus Envelope Protein Late-Stage Fusion Intermediate" Journal of Virology, 87(4):2287-2293 (2013).
Kostyuchenko et al. "Near-Atomic Resolution Cryo-Electron Microscopic Structure of Dengue Serotype 4 Virus" Journal of Virology, 88(1):477-482 (2014).
Kraus et al. "Comparison of Plaque- and Flow Cytometry-Based Methods for Measuring Dengue Virus Neutralization" Journal of Clinical Microbiology, 45(11):3777-3780 (2007).
Kuhn et al. "Structure of Dengue Virus: Implications for Flavivirus Organization, Maturation, and Fusion" Cell, 108(5):717-725 (2002).
Kurosaki et al. "Memory B cells" Nature Reviews Immunology, 15:149-159 (2015) (Abstract).
Lai et al. "Epitope Determinants of a Chimpanzee Dengue Virus Type 4 (DENV-4)-Neutralizing Antibody and Protection against DENV-4 Challenge in Mice and Rhesus Monkeys by Passively Transferred Humanized Antibody" Journal of Virology, 81(23): 12766-12774 (2007).
Lambeth et al. "Flow Cytometry-Based Assay for Titrating Dengue Virus" Journal of Clinical Microbiology, 43(7):3267-3272 (2005).
Lindesmith et al. "Broad Blockade Antibody Responses in Human Volunteers After Immunization With A Multivalent Norovirus VLP Candidate Vaccine: Immunological Analyses from a Phase I Clinical Trial" PLoS Medicine, 12(3), 32 pages (2015).
Lindesmith et al. "Particle Conformation Regulates Antibody Access to a Conserved GII.4 Norovirus Blockade Epitope" Journal of Virology, 88(16):8826-8842 (2014).
Lok et al. "Binding of a neutralizing antibody to dengue virus alters the arrangement of surface glycoproteins" Nature Structural & Molecular Biology, 15(3):312-317 (2008).
Mathew et al. "B-Cell Responses During Primary and Secondary Dengue Virus Infections in Humans" Journal of Infectious Diseases, 204(10):1514-1522 (2011).
Messer et al. "Development and Characterization of a Reverse Genetic System for Studying Dengue Virus Serotype 3 Strain Variation and Neutralization" PLoS Neglected Tropical Diseases, 6(2):e1486 (2012).
Messer et al. "Functional Transplant of a Dengue Virus Serotype 3 (DENV3)-Specific Human Monoclonal Antibody Epitope into DENV1" Journal of Virology, 90(10):5090-5097 (2016).
Modis et al. "A ligand-binding pocket in the dengue virus envelope glycoprotein" Proceedings of the National Academy of Sciences, 100(12):6986-6991 (2003).
Modis et al. "Structure of the dengue virus envelope protein after membrane fusion" Nature, 427:313-319 (2004).
Nivarthi et al. "Mapping the Human Memory B Cell and Serum Neutralizing Antibody Responses to Dengue Virus Serotype 4 Infection and Vaccine" Journal of Virology, 91(5):e02041-16 (2017).
Oliphant et al. "Antibody Recognition and Neutralization Determinants on Domains I and II of West Nile Virus Envelope Protein" Journal of Virology, 80(24):12149-12159 (2006).
Paes et al. "Atomic-Level Mapping of Antibody Epitopes on a GPCR" Journal of the American Chemical Society, 131(20):6952-6954 (2009).
Roehrig "Antigenic structure of flavivirus proteins" Advances in Virus Research, 59:141-176 (2003) (Abstract).
Rossi et al. "Genetic and phenotypic characterization of sylvatic dengue virus type 4 strains" Virology, 423(1):58-67 (2012).
Rouvinski et al. "Recognition determinants of broadly neutralizing human antibodies against dengue viruses" Nature, 520:109-113 (2015).
Simmons et al. "Dengue" The New England Journal of Medicine, 366:1423-1432 (2012).
Smith et al. "Human Monoclonal Antibodies Derived From Memory B Cells Following Live Attenuated Dengue Virus Vaccination or Natural Infection Exhibit Similar Characteristics" Journal of Infectious Diseases, 207(12):1898-1908 (2013).
Smith et al. "Isolation of Dengue Virus-Specific Memory B Cells with Live Virus Antigen from Human Subjects following Natural Infection Reveals the Presence of Diverse Novel Functional Groups of Antibody Clones" Journal of Virology, 88(21):12233-12241 (2014).
Smith et al. "Persistence of Circulating Memory B Cell Clones with Potential for Dengue Virus Disease Enhancement for Decades following Infection" Journal of Virology, 86(5):2665-2675 (2012).

(56) References Cited

OTHER PUBLICATIONS

Sukupolvi-Petty et al. "Functional Analysis of Antibodies against Dengue Virus Type 4 Reveals Strain-Dependent Epitope Exposure That Impacts Neutralization and Protection" Journal of Virology, 87(16):8826-8842 (2013).

Teoh et al. "The Structural Basis for Serotype-Specific Neutralization of Dengue Virus by a Human Antibody" Science Translational Medicine, 4(139), 10 pages (2012).

Thomas et al. "Critical issues in dengue vaccine development" Current Opinion in Infectious Diseases, 24(5):442-450 (2011) (Abstract).

Vasilakis et al. "Chapter 1 The History and Evolution of Human Dengue Emergence" Advances in Virus Research, 72:1-76 (2008) (Abstract).

Wahala et al. "Dengue virus neutralization by human immune sera: Role of envelope protein domain III-reactive antibody" Virology, 392(1):103-113 (2009).

Wahala et al. "Natural Strain Variation and Antibody Neutralization of Dengue Serotype 3 Viruses" PLoS Pathogens, 6(3):e1000821 (2010).

Wahala et al. "Recombinant Dengue Type 2 Viruses with Altered E Protein Domain III Epitopes Are Efficiently Neutralized by Human Immune Sera" Journal of Virology, 86(7):4019-4023 (2012).

Zhang et al. "Conformational Changes of the Flavivirus E Glycoprotein" Structure, 12(9):1607-1618 (2004).

Zhang et al. "Cryo-EM structure of the mature dengue virus at 3.5-Å resolution" Nature Structural & Molecular Biology, 20(1):105-111 (2013).

International Search Report and the Written Opinion of the International Searching Authority corresponding to International Patent Application No. PCT/US2018/034151 (9 pages) (dated Sep. 27, 2018).

* cited by examiner

Alignment of DENV1-4, YFV and JEV glycoprotein amino acid sequences

```
                                1                                                   50
SEQ ID NO: 3     DENV3_E_AA#2   MRCVGIGNRD FVEGLSGATW VDVVLEHGGC VTTMAKNKPT LDIELQKTEA   50
SEQ ID NO: 1     DENV1_E_AA     MRCVGIGNRD FVEGLSGATW VDVVLEHGSC VTTMAKDKPT LDIELLKTEV   50
SEQ ID NO: 4     DENV4_E_AA     MRCVGVGNRD FVEGVSGGAW VDLVLEHGGC VTTMAQGKPT LDFELTKTTA   50
SEQ ID NO: 2     DENV_2_E_AA    MRCIGISNRD FVEGVSGGSW VDIVLEHGSC VTTMAKNKPT LDFELIKTEA   50
SEQ ID NO: 20    YF_17D         AHCIGITDRD FIEGVHGGTW VSATLEQDKC VTVMAPDKPS LDISLETVAI   50
SEQ ID NO: 21    JESA14         FNCLGMGNRD FIEGASGATW VDLVLEGDSC LTIMANDKPT LDVRMINIEA   50

51                                                 100
SEQ ID NO: 3     DENV3_E_AA#2   TQLATLRKLC IEGKITNITT DSRCPTQGEA VLPEEQDQNY VCKHTYVDRG  100
SEQ ID NO: 1     DENV1_E_AA     TNPAVLRKLC IEAKISNTTT DSRCPTQGEA TLVEEQDTNF VCRRTFVDRG  100
SEQ ID NO: 4     DENV4_E_AA     KEVALLRTYC IEASISNITT ATRCPTQGEP YLKEEQDQQY ICRRDVVDRG  100
SEQ ID NO: 2     DENV_2_E_AA    KQPATLRKYC IEAKLTNTTT ESRCPTQGEP SLNEEQDKRF VCKHSMVDRG  100
SEQ ID NO: 20    YF_17D         DRPAEVRKVC YNAVLTHVKI NDKCPSTGEA HLAEENEGDN ACKRTYSDRG  100
SEQ ID NO: 21    JESA14         SQLAEVRSYC YHASVTDIST VARCPTTGEA HNEKRADSSY VCKQGFTDRG  100

101                                                150
SEQ ID NO: 3     DENV3_E_AA#2   WGNGCGLFGK GSLVTCAKFQ CLEPIEGKVV QYENLKYTVI ITVHTGDQHQ  150
SEQ ID NO: 1     DENV1_E_AA     WGNGCGLFGK GSLITCAKFK CVTKLEGKIV QYENLKYSVI VTVHTGDQHQ  150
SEQ ID NO: 4     DENV4_E_AA     WGNGCGLFGK GGVVTCAKFS CSGKITGNLV QIENLEYTVV VTVHNGDTHA  150
SEQ ID NO: 2     DENV_2_E_AA    WGNGCGLFGK GGIVTCAMFT CKKNMEGKVV QPENLEYTIV VTPHSGEEHA  150
SEQ ID NO: 20    YF_17D         WGNGCGLFGK GSIVACAKFT CAKSMSLFEV DQTKIQYVIR AQLHVGAKQE  150
SEQ ID NO: 21    JESA14         WGNGCGLFGK GSIDTCAKFS CTSKAIGRTI QPENIKYEVG IFVHGTTTSE  150

151                                                200
SEQ ID NO: 3     DENV3_E_AA#2   VGNET        QGVTAEIT PQASTTEAIL PEYGTLGLEC SPRTGLDFNE  193
SEQ ID NO: 1     DENV1_E_AA     VGNETTE      HGTTATIT PQAPTSEIQL TDYGALTLDC SPRTGLDFNE  195
SEQ ID NO: 4     DENV4_E_AA     VGNDTSN     .HGVTATIT PRSPSVEVKL PDYGELTLDC EPRSGIDFNE  195
SEQ ID NO: 2     DENV_2_E_AA    VGNDTGK... ..HGKEIKVT PQSSITEAEL TGYGTVTMEC SPRTGLDFNE  195
SEQ ID NO: 20    YF_17D         NWTTDI         KTLKFD ALSGSQEVEF IGYGKATLEC QVQTAVDFGN  192
SEQ ID NO: 21    JESA14         NHGNYSAQVG ASQAAKFTVT PNAPSITLKL GDYGEVTLDC EPRSGLNTEA  200

201                                                250
SEQ ID NO: 3     DENV3_E_AA#2   MILLTMKNKA WMVHRQWFFD LPLPWTSGAT TETPTWNRKE LLVTFKNAHA  243
```

Figure 7

```
SEQ ID NO: 1        DENV1_E_AA     MVLLTMEKKS WLVHKQWFLD LPLPWTSGAS TSQETWNRQD LLVTFKTAHA  245
SEQ ID NO: 4        DENV4_E_AA     MIMLKMKKKT WLVHKQWFLD LPLPWTAGAD TSEVHWNYKE RMVTFKVPHA  245
SEQ ID NO: 2        DENV_2_E_AA    MVLLQMENKA WLVHRQWFLD LPLPWLPGAD TQGSNWIQKE TLVTFKNPHA  245
SEQ ID NO: 20       YF_17D         SYIAEMETES WIVDRQWAQD ITLPWQSG.  SGGVWREMH  HLVEFEPPHA  239
SEQ ID NO: 21       JESA14         FYVMTVGSKS FLVHREWFHD LALPWTSP   SSTAWRNRE  LLMEFEEAHA  247

251                                         300
SEQ ID NO: 3        DENV3_E_AA#2   KKQEVVVLGS QEGAMHTALT GATEIQNSGG TS    IFAG HLKCRLKMDK  289
SEQ ID NO: 1        DENV1_E_AA     KKQEVVVLGS QEGAMHTALT GATEIQTSGT TT....IFAG HLKCRLKMDK  291
SEQ ID NO: 4        DENV4_E_AA     KRQDVTVLGS QEGAMHSALA GATEVDSGDG NH....MFAG HLKCKVRMEK  291
SEQ ID NO: 2        DENV_2_E_AA    KKQDVVVLGS QEGAMHTALT GATEIQMSSG NL....LFTG HLKCRLRMDK  291
SEQ ID NO: 20       YF_17D         ATIRVLALGN QEGSLKTALT GAMRVTKDTN DNNLYKLHGG HVSCRVKLSA  289
SEQ ID NO: 21       JESA14         TKQSVVALGS QEGGLHQALA GAIVVEYSSS VK....LTSG HLKCRLKMDK  293

301                                         350
SEQ ID NO: 3        DENV3_E_AA#2   LELKGMSYAM CTNTFVLKKE VSETQHGTIL IKVEYKGEDA PCKIPF.STE  338
SEQ ID NO: 1        DENV1_E_AA     LTLKGMSYVM CTGSFKLEKE VAETQHGTVL VQVKYEGTDA PCKIPF.SSQ  340
SEQ ID NO: 4        DENV4_E_AA     LRIKGMSYTM CSGKFSIDKE MAETQHGTTV VKVKYEGAGA PCKVPI.EIR  340
SEQ ID NO: 2        DENV_2_E_AA    LQLKGMSYSM CTGKFKVVKE IAETQHGTIV IRVQYEGDGS PCKIPF.EIM  340
SEQ ID NO: 20       YF_17D         LTLKGTSYKI CTDKMFFVKN PTDTGHGTVV MQVKVSKGAP CRIPVI.VAD  338
SEQ ID NO: 21       JESA14         LALKGTTYGM CTEKFSFAKN PADTGHGTVV IELSYSGSDG PCKIPIVSVA  343

351                                         400
SEQ ID NO: 3        DENV3_E_AA#2   DGQGKAHNGR LITANPVVTK K..EEPVNIE AEPPFGESNI VIGIGDNALK  386
SEQ ID NO: 1        DENV1_E_AA     DEKGVTQNGR LITANPIVTD K..EKPVNIE AEPPFGESYI VVGAGEKALK  388
SEQ ID NO: 4        DENV4_E_AA     DVNKEKVVGR VISSTPLAEN T...NSVTNIE LEPPFGDSYI VIGVGNSALT  388
SEQ ID NO: 2        DENV_2_E_AA    DLEKRHVLGR LITVNPIVTE K. DSPVNIE AEPPFGDSYI IIGVDPGQLK  388
SEQ ID NO: 20       YF_17D         DLTAAINKGI LVTVNPIAST N  DDEVLIE VNPPFGDSYI IVGRGDSRLT  386
SEQ ID NO: 21       JESA14         SLNDMTPVGR LVTVNPFVAT SSANSKVLVE MEPPFGDSYI VVGRGDKQIN  393

401        424
SEQ ID NO: 3        DENV3_E_AA#2   INWYKKGSSI GKMFEATARG ARRM                              410
SEQ ID NO: 1        DENV1_E_AA     LSWFKKGSSI GKMFEATARG AR..                              410
SEQ ID NO: 4        DENV4_E_AA     LHWFRKGSSI GKMFESTYRG AK..                              410
SEQ ID NO: 2        DENV_2_E_AA    LNWFKKGSSI GQMFETTMRG AK..                              410
SEQ ID NO: 20       YF_17D         YQWHKEGSSI GKLFTQTMKG VERL                              410
SEQ ID NO: 21       JESA14         HHWHKAGSTL GKAFSTT                                     410
```

Figure 7 (cont'd)

```
SEQ ID NO: 2   DENV2              MRCIGISNRDFVEGVSGGSWVDIVLEHGSCVTTMAKNKPTLDFELIKTEAKQPATLRKYC   60
SEQ ID NO: 9   DENV2/4 M14        MRCIGISNRDFVEGVSGGSWVDIVLEHGSCVTTMAKNKPTLDFELIKTEAKEVALLRTYC   60
SEQ ID NO: 22  DENV2/4 M14+       MRCIGISNRDFVEGVSGGSWVDIVLEHGSCVTTMAKNKPTLDFELTKTTAKEVALLRTYC   60
SEQ ID NO: 10  DENV2/4 M-Complete MRCIGISNRDFVEGVSGGSWVDIVLEHGSCVTTMAKNKPTLDFELTKTTAKEVALLRTYC   60
SEQ ID NO: 24  DENV2/4 Modified   MRCIGISNRDFVEGVSGGSWVDIVLEHGSCVTTMAKNKPTLDFELIKTEAKEVALLRTYC   60
SEQ ID NO: 25  DENV2/4 EDII Swap  MRCIGISNRDFVEGVSGGSWVDIVLEHGGCVTTMAQGKPTLDFELTKTTAKEVALLRTYC   60
SEQ ID NO: 4   DENV4              MRCVGVGNRDFVEGVSGGAWVDLVLEHGSCVTTMAQGKPTLDFELTKTTAKEVALLRTYC   60
                                  ***.* ********** .***:******.*******:.:************* *****

SEQ ID NO: 2   DENV2              IEAKLTNTTESRCPTQGEPSLNEEQDKRFVCKHSMVDRGWGNGCGLFGKGGIVTCAMFT   120
SEQ ID NO: 9   DENV2/4 M14        IEAKLTNTTESRCPTQGEPSLNEEQDKRFVCKHSMVDRGWGNGCGLFGKGIVTCAKFS   120
SEQ ID NO: 22  DENV2/4 M14+       IEAKLTNTTESRCPTQGEPSLNEEQDKRFVCKHSMVDRGWGNGCGLFGKGIVTCAKFS   120
SEQ ID NO: 10  DENV2/4 M-Complete IEASISNITTASRCPTQGEPYLKEEQDQQYICKHSMVDRGWGNGCGLFGKGIVTCAKFS   120
SEQ ID NO: 24  DENV2/4 Modified   IEAKISNITTESRCPTQGEPYLKEEQDQQYICKHSMVDRGWGNGCGLFGKGIVTCAKFS   120
SEQ ID NO: 25  DENV2/4 EDII Swap  IEASISNITTATRCPTQGEPYLKEEQDQQYICRRDVVDRGWGNGCGLFGKGVVTCAKFS   120
SEQ ID NO: 4   DENV4              IEASISNITTATRCPTQGEPYLKEEQDQQYICRRDVVDRGWGNGCGLFGKGVVTCAKFS   120
                                  ***.:*:.** ********:*:*****:::**::..:*******************:

SEQ ID NO: 2   DENV2              CKKNMEGKVVQPENLEYTIVVTPHSGEEHAVGNDTGKHGKEIKVTPQSSITEAELTGYGT   180
SEQ ID NO: 9   DENV2/4 M14        CSGKITGNLVQPENLEYTIVVTPHSGEEHAVGNDTGKHGKEIKVTPQSSITEAELTGYGT   180
SEQ ID NO: 22  DENV2/4 M14+       CSGKITGNLVQIENLEYTIVVTPHSGEEHAVGNDTGKHGKEIKVTPQSSITEAELTGYGT   180
SEQ ID NO: 10  DENV2/4 M-Complete CSGKITGNLVQPENLEYTIVVTPHSGEEHAVGNDTGKHGKEIKVTPQSSITEAELTGYGT   180
SEQ ID NO: 24  DENV2/4 Modified   CSGKITGNLVQPENLEYTIVVTPHSGEEHAVGNDTGKHGKEIKVTPQSSITEAELTGYGT   180
SEQ ID NO: 25  DENV2/4 EDII Swap  CSGKITGNLVQIENLEYTIVVTPHSGEEHAVGNDTGKHGKEIKVTPQSSITEAELTGYGT   180
SEQ ID NO: 4   DENV4              CSGKITGNLVQIENLEYTVVVTVHNGDTHAVGNDTSNHGVTATITPRSPSVEVKLPDYGE   180
                                  *.    :: :.* : *****.::.* . ***********..::..      .:*  **

SEQ ID NO: 2   DENV2              VTMECSPRTGLDFNEMVLLQMENKAWLVHRQWFLDLPLPWLPGADTQGSNWIQKETLVTF   240
SEQ ID NO: 9   DENV2/4 M14        VTMECSPRTGLDFNEMVLLKMKKKTWLVHKQWFLDLPLPWTAGADTSEVHWNYKETLVTF   240
SEQ ID NO: 22  DENV2/4 M14+       VTMECSPRSGIDFNEMVLLKMKKKTWLVHKQWFLDLPLPWTAGADTSEVHWNYKETLVTF   240
SEQ ID NO: 10  DENV2/4 M-Complete VTMECSPRTGIDFNEMVLLKMKKKTWLVHKQWFLDLPLPWTAGADTSEVHWNYKETLVTF   240
SEQ ID NO: 24  DENV2/4 Modified   VTMECSPRTGIDFNEMVLLKMKKKTWLVHKQWFLDLPLPWTAGADTSEVHWNYKETLVTF   240
SEQ ID NO: 25  DENV2/4 EDII Swap  VTMECSPRTGLDFNEMILMKKKTWLVHKQWFLDLPLPWTAGADTSEVHWNYKERMVTF   240
SEQ ID NO: 4   DENV4              LTLDCEPRSGIDFNEMILMKRKKTWLVHKQWFLDLPLPWTAGADTSEVHWNYKERMVTF   240
                                  :*  .:*::**:****:*  : :*:****:*********** .***.:  *.:*:**
```

Figure 8

| | | | |
|---|---|---|---|
| SEQ ID NO: 2 | DENV2 | KNPHAKKQDVVVLGSQEGAMHTALTGATEIQMSSGNLLFTGHLKCRLRMDKLQLKGMSYS | 300 |
| SEQ ID NO: 9 | DENV2/4 M14 | KNPHAKKQDVVVLGSQEGAMHTALTGATEVDSGDGNHMFAGHLKCRLRMDKLQLKGMSYS | 300 |
| SEQ ID NO: 22 | 2DENV2/4 M14+ | KNPHAKKQDVVVLGSQEGAMHTALTGATEVDSGDGNHMFAGHLKCRLRMDKLQLKGMSYS | 300 |
| SEQ ID NO: 10 | DENV2/4 M-Complete | KNPHAKRQDVTVLGSQEGAMHTALTGATEVDSGDGNHMFAGHLKCRLRMDKLQLKGMSYS | 300 |
| SEQ ID NO: 24 | DENV2/4 Modified | KNPHAKRQDVTVLGSQEGAMHTALTGATEVDSGDGNHMFTGHLKCRLRMDKLQLKGMSYS | 30 |
| SEQ ID NO: 25 | DENV2/4 EDII Swap | KVPHAKRQDVTVLGSQEGAMHSALAGATEVDSGDGNHMFAGHLKCRLRMDKLQLKGMSYS | 300 |
| SEQ ID NO: 4 | DENV4 | KVPHAKRQDVTVLGSQEGAMHSALAGATEVDSGDGNHMFAGHLKCVRMEKLRIKGMSYT | 300 |
| | | * **: ********::*** .. . .:*:**********:.:***: | |
| SEQ ID NO: 2 | DENV2 | MCTGKFKVKEIAETQHGTIVIRVQYEGDGSPCKIPFEIMDLEKRHVLGRLITVNPIVTE | 360 |
| SEQ ID NO: 9 | DENV2/4 M14 | MCTGKFKVKEIAETQHGTIVIRVQYEGDGSPCKIPFEIMDLEKRHVLGRLITVNPIVTE | 360 |
| SEQ ID NO: 22 | 2DENV2/4 M14+ | MCTGKFKVKEIAETQHGTIVIRVQYEGDGSPCKIPFEIMDLEKRHVLGRLITVNPIVTE | 360 |
| SEQ ID NO: 10 | DENV2/4 M-Complete | MCTGKFKVKEIAETQHGTIVIRVQYEGDGSPCKIPFEIMDLEKRHVLGRLITVNPIVTE | 360 |
| SEQ ID NO: 24 | DENV2/4 Modified | MCTGKFKVKEIAETQHGTIVIRVQYEGDGSPCKIPFEIMDLEKRHVLGRLITVNPIVTE | 360 |
| SEQ ID NO: 25 | DENV2/4 EDII Swap | MCTGKFKVKEIAETQHGTIVIRVQYEGDGSPCKIPFEIMDLEKRHVLGRLITVNPIVTE | 360 |
| SEQ ID NO: 4 | DENV4 | MCSGKFSIDKEMAETQHGTTVVKVKYEGAGAPCKVPIEIRDVNKEKVVGRVISSTPLAEN | 360 |
| | | :...: **:** *::*: ******:.:.*.:** . .*:. .. | |
| SEQ ID NO: 2 | DENV2 | KDSPVNIEAEPPFGDSYIIIGVDPGQLKLNWFKK | 394 |
| SEQ ID NO: 9 | DENV2/4 M14 | KDSPVNIEAEPPFGDSYIIIGVDPGQLKLNWFKK | 394 |
| SEQ ID NO: 22 | 2DENV2/4 M14+ | KDSPVNIEAEPPFGDSYIIIGVDPGQLKLNWFKK | 394 |
| SEQ ID NO: 10 | DENV2/4 M-Complete | KDSPVNIEAEPPFGDSYIIIGVDPGQLKLNWFKK | 394 |
| SEQ ID NO: 24 | DENV2/4 Modified | KDSPVNIEAEPPFGDSYIIIGVDPGQLKLNWFKK | 394 |
| SEQ ID NO: 25 | DENV2/4 EDII Swap | KDSPVNIELPPFGDSYIIIGVDPGQLKLNWFKK | 394 |
| SEQ ID NO: 4 | DENV4 | TNSVTNIELPPFGDSYIVIGVGNSALTLHWFRK | 394 |
| | | .:*. .* *****:.:. . .*.*:*:..* | |

Figure 8 (cont'd)

METHODS AND COMPOSITIONS FOR DENGUE VIRUS SEROTYPE 4 EPITOPES

RELATED APPLICATIONS

This application is a 35 U.S.C. § 371 national phase application of International Application Serial No. PCT/US2018/034151, filed May 23, 2018, which claims the benefit, under 35 U.S.C. § 119(e), of U.S. Provisional Application Ser. No. 62/510,133, filed May 23, 2017, and U.S. Provisional Application Ser. No. 62/561,942, filed Sep. 22, 2017, the entire contents of each of which are incorporated by reference herein.

STATEMENT OF GOVERNMENT SUPPORT

This invention was made with government support under Grant Nos. AI107731, AI106695 and AI109761 awarded by the National Institutes of Health. The United States government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-816_ST25.txt, 139,185 bytes in size, generated on Nov. 15, 2019 and filed via EFS-Web, is provided in lieu of a paper copy. This Sequence Listing is hereby incorporated herein by reference into the specification for its disclosures.

BACKGROUND OF THE INVENTION

Dengue is a mosquito-borne flavivirus that is spreading at an unprecedented rate and has developed into a major health and economic burden in over 50 countries. Even though infected individuals develop potent and long-lasting serotype-specific neutralizing antibodies (Abs), the epitopes engaged by human neutralizing Abs have not been identified.

The four serotypes of dengue virus are the causative agents of dengue fever and dengue hemorrhagic fever. People exposed to primary DENV infections develop long-term neutralizing antibody responses principally only to the infecting serotype. An effective vaccine against dengue needs to elicit long lasting protective antibody responses to all four serotypes simultaneously. We and others have defined antigenic sites on the envelope (E) protein of viruses of dengue serotypes 1, 2 and 3 targeted by human neutralizing antibodies. The mechanisms of serotype 4 neutralization by human antibodies are poorly understood. Here, we report on the properties of human antibodies that neutralize dengue serotype 4. People exposed to serotype 4 infections or a live attenuated serotype 4 vaccine developed strongly neutralizing antibodies that bound to similar sites on the viral E protein. These studies provide a foundation for developing and evaluating DENV4 vaccines.

SUMMARY OF THE INVENTION

The present invention provides a chimeric dengue virus E glycoprotein comprising the amino acid sequence:

(SEQ ID NO: 5)
MRCVGIGNRDFVEGLSGATWVDVVLEHGSCVTTMAKDKPTLDIELLKTEV

KEVALLRTLCIEAKISNTTTDSRCPTQGEATLVEEQDTNFVCRRTFVDRG

WGNGCGLFGKGSLITCAKFKCVTKITGNLVQYENLKYSVIVTVHTGDQHQ

VGNETTEHGTTATITPQAPTSEIQLTDYGALTLDCSPRTGLDFNEMVLLK

MKKKTWLVHKQWFLDLPLPWTAGASTSQETWNRKDLLVTFKTAHAKKQEV

VVLGSQEGAMHTALTGATEVDSGDTTHMFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKK
(DENV1/4 M12).

The present invention further provides a chimeric dengue virus E glycoprotein comprising the amino acid sequence:

(SEQ ID NO: 6)
MRCVGIGNRDFVEGLSGATWVDVVLEHGSCVTTMAKDKPTLDIELLKTEV

KEVALLRTLCIEAKISNTTTDSRCPTQGEATLVEEQDTNFVCRRTFVDRG

WGNGCGLFGKGSLITCAKFSCSGKITGNLVQYENLKYSVIVTVHTGDQHQ

VGNETTEHGTTATITPQAPTSEIQLTDYGALTLDCSPRTGLDFNEMVLLK

MKKKTWLVHKQWFLDLPLPWTAGASTSEVHWNYKDLLVTFKTAHAKKQEV

VVLGSQEGAMHTALTGATEVDSGDTTHMFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKK
(DENV1/4 M14).

Also provided herein is a chimeric dengue virus E glycoprotein comprising the amino acid sequence:

(SEQ ID NO: 7)
MRCVGIGNRDFVEGLSGATWVDVVLEHGSCVTTMAKDKPTLDIELTKTTV

KEVALLRTLCIEASISNITTASRCPTQGEAYLKEEQDQQYICRRTFVDRG

WGNGCGLFGKGSLITCAKFSCSGKITGNLVQYENLKYSVIVTVHTGDQHQ

VGNETTEHGTTATITPQAPTSEIQLTDYGALTLDCSPRTGLDFNEMVLLK

MKKKTWLVHKQWFLDLPLPWTAGASTSEVHWNYKDLLVTFKTAHAKRQEV

TVLGSQEGAMHTALTGATEVDSGDTTHMFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKK
(DENV1/4 M-Complete).

In addition, the present invention provides a chimeric dengue virus E glycoprotein comprising the amino acid sequence:

(SEQ ID NO: 8)
MRCIGISNRDFVEGVSGGSWVDIVLEHGSCVTTMAKNKPTLDFELIKTEA

KEVALLRTYCIEAKLTNTTTESRCPTQGEPSLNEEQDKRFVCKHSMVDRG

WGNGCGLFGKGGIVTCAMFTCKKKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTQGSNWIQKETLVTFKNPHAKKQDV

-continued

```
VVLGSQEGAMHTALTGATEVDSGDGNHMFAGHLKCRLMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV 2/4 M12).
```

Further provided herein is a chimeric dengue virus E glycoprotein comprising the amino acid sequence:

```
                                        (SEQ ID NO: 9)
MRCIGISNRDFVEGVSGGSWVDIVLEHGSCVTTMAKNKPTLDFELIKTEA

KEVALLRTYCIEAKLTNTTTESRCPTQGEPSLNEEQDKRFVCKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKKQDV

VVLGSQEGAMHTALTGATEVDSGDGNHMFAGHLKCRLMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV 2/4 M14).
```

Additionally provided herein is a chimeric dengue virus E glycoprotein comprising the amino acid sequence:

```
                                       (SEQ ID NO: 10)
MRCIGISNRDFVEGVSGGSWVDIVLEHGSCVTTMAKNKPTLDFELTKTTA

KEVALLRTYCIEASISNITTASRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKRQDV

TVLGSQEGAMHTALTGATEVDSGDGNHMFAGHLKCRLMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENY 2/4 M-complete).
```

Further provided herein is a chimeric dengue virus E glycoprotein comprising the amino acid sequence:

```
                                       (SEQ ID NO: 11)
MRCVGIGNRDFVEGLSGATWVDVVLEHGGCVTTMAKNKPTLDIELQKTEA

KEVALLRTLCIEGKITNITTDSRCPTQGEAVLPEEQDQNYVCKHTYVDRG

WGNGCGLFGKGSLVTCAKFQCLEKITGNLVQYENLKYTVIITVHTGDQHQ

VGNETQGVTAEITPQASTTEAILPEYGTLGLECSPRTGLDFNEMILLKMK

KKTWMVHRQWFFDLPLPWTAGATTETPTWNRKELLVTFKNAHAKKQEVVV

LGSQEGAMHTALTGATEVDSGDGTHMFAGHLKCRLMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKK
(DENV3/4 M12).
```

The present invention also provides a chimeric dengue virus E glycoprotein comprising the amino acid sequence:

```
                                       (SEQ ID NO: 12)
MRCVGIGNRDFVEGLSGATWVDVVLEHGGCVTTMAKNKPTLDIELQKTEA

KEVALLRTLCIEGKITNITTDSRCPTQGEAVLPEEQDQNYVCKHTYVDRG

WGNGCGLFGKGSLVTCAKFSCSGKITGNLVQYENLKYTVIITVHTGDQHQ

VGNETQGVTAEITPQASTTEAILPEYGTLGLECSPRTGLDFNEMILLKMK

KKTWMVHRQWFFDLPLPWTAGATTSEVHWNYKELLVTFKNAHAKKQEVVV

LGSQEGAMHTALTGATEVDSGDGTHMFAGHLKCRLKMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKK
(DENV3/4 M14).
```

A chimeric dengue virus E glycoprotein is also provided herein, comprising the amino acid sequence:

```
                                       (SEQ ID NO: 13)
MRCVGIGNRDFVEGLSGATWVDVVLEHGGCVTTMAKNKPTLDIELTKTTA

KEVALLRTLCIEGSISNITTASRCPTQGEAYLKEEQDQQYICKHTYVDRG

WGNGCGLFGKGSLVTCAKFSCSGKITGNLVQYENLKYTVIITVHTGDQHQ

VGNETQGVTAEITPQASTTEAILPEYGTLGLECSPRTGLDFNEMILLKMK

KKTWMVHKQWFFDLPLPWTAGATTSEVHWNYKELLVTFKNAHAKRQEVTV

LGSQEGAMHTALTGATEVDSGDGTHMFAGHLKCRLMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKK
(DEN V3/4 M-Complete).
```

A chimeric dengue virus E glycoprotein is also provided herein, comprising the amino acid sequence:

```
                                       (SEQ ID NO: 22)
MRCIGISNRDFVEGVSGGSWVDIVLEHGSCVTTMAKNKPTLDFELTKTTA

KEVALLRTYCIEAKLTNTTTESRCPTQGEPSLNEEQDKRFVCKHSMVDRG

WGNGCGLFGKGGIVTCAKFSCSGKITGNLVQIENLEYTIVVTPHSGEEHA

VGNDTGKHGKEIKVTPQSSITEAELTGYGTVTMECSPRSGIDFNEMVLLK

MKKKTWLVHKQWFLDLPLPWTAGADTSEVHWNDKETLVTFKNPHAKKQDV

VVLGSQEGAMHTALTGATEVDSGDGNHMFAGHLKCRLMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV2/4 M14/).
```

A chimeric dengue virus E glycoprotein is also provided herein, comprising the amino acid sequence:

```
                                       (SEQ ID NO: 24)
MRCIGISNRDFVEGVSGGSWVDIVLEHGSCVTTMAKNKPTLDFELTKTTA

KEVALLRTYCIEAKISNITTESRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKQDV

TVLGSQEGAMHTALTGATEVDSGDGNHMFAGHLKCRLMDKLQLKGMSYS
```

-continued

```
MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV2/4 M-Complete Modified Swap).
```

A chimeric dengue virus E glycoprotein is also provided herein, comprising the amino acid sequence:

```
                                              (SEQ ID NO: 25)
MRCIGISNRDFVEGVSGGSWVDIVLEHGSCVTTMAKNKPTLDFELIKTEA

KEVALLRTYCIEASISNITTATRCPTQGEPYLKEEQDQQYICRRDVVDRG

WGNGCGLFGKGGVVTCAKFSCSGKITGNLVQIENLEYTIVVTPHSGEEHA

VGNDTGKHGKEIKVTPQSSITEAELTGYGTVTMECSPRTGLDFNEMILMK

MKKKTWLVHKQWFLDLPLPWTAGADTSEVHWNYKERMVTFKVPHAKRQDV

TVLGSQEGAMHSALAGATEVDSGDGNHMFTGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV2/4 EDII Swap).
```

The present invention also provides a nucleic acid molecule encoding the chimeric dengue virus E glycoprotein of this invention, a vector comprising the nucleic acid molecule of this invention, a flavivirus particle comprising the chimeric dengue virus E glycoprotein of this invention and/or the nucleic acid molecule of this invention, a virus like particle (VLP) comprising the chimeric dengue virus E glycoprotein of this invention, and a composition comprising the chimeric dengue virus E glycoprotein of this invention and/or the nucleic acid molecule of this invention, the vector of this invention, the flavivirus particle of this invention and/or the VLP of this invention, in a pharmaceutically acceptable carrier.

Further provided herein is a method of producing an immune response to a dengue virus in a subject, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

Also provided herein is a method of treating a dengue virus infection in a subject in need thereof, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

In a further embodiment, the present invention provides a method of preventing a dengue virus infection in a subject, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

Additionally provided herein is a method of protecting a subject from the effects of dengue virus infection, the method comprising administering to the subject an effective amount of the chimeric dengue virus E glycoprotein of this invention, the nucleic acid molecule of this invention, the vector of this invention, the flavivirus particle of this inven-
tion, the VLP of this invention, the composition of this invention, and any combination thereof.

A method is also provided herein of detecting a neutralizing antibody to a dengue virus, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

In addition, the present invention provides a method of identifying a neutralizing antibody to a dengue virus, comprising: (a) contacting an antibody with the E glycoprotein of this invention; and (b) determining if the antibody binds to the E glycoprotein, wherein binding by the antibody to the E glycoprotein identifies the antibody as a neutralizing antibody to a dengue virus.

Furthermore the present invention provides a method of identifying an immunogenic composition that induces a neutralizing antibody to a dengue virus in a subject, the method comprising: (a) contacting a biological sample from a subject that has been administered the immunogenic composition with the E glycoprotein of this invention; (b) determining if the biological sample comprises an antibody that binds the E glycoprotein; and (c) identifying the immunogenic composition as inducing a neutralizing antibody to a dengue virus in the subject if the biological sample comprises an antibody that binds to the E glycoprotein.

In another embodiment, the present invention provides a method of identifying an immunogenic composition that induces a neutralizing antibody to a dengue virus in a subject, the method comprising: (a) administering an immunogenic composition comprising a dengue virus antigen to a subject in an amount effective to induce antibodies against the dengue virus antigen; (b) contacting a biological sample from the subject with the E glycoprotein of any of claims 1-9; (c) determining if the biological sample comprises an antibody that binds the E glycoprotein; and (d) identifying the immunogenic composition as inducing a neutralizing antibody to a dengue virus in the subject if the biological sample comprises an antibody that binds to the E glycoprotein.

BRIEF DESCRIPTION OF THE DRAWINGS

(FIG. 2A) Neutralization of DENV1, 2, 3 and 4. (FIG. 2B) Binding to DENV4 whole virions, recombinant E protein ectodomain (rE) and recombinant E protein domain III (rEDIII). Both antibodies bound well to whole DENV4 virions and strongly neutralized DENV4. The MAbs bound poorly to rE or EDIII.

(FIG. 4A) Binding of hMAbs D4-126, D4-131 to DENV4, DENV3 and rDENV4/3 viruses. (FIG. 4B) DENV4 and rDENV4/3 neutralization by hMAbs D4-126, D4-131. Both hMAbs failed to bind and neutralize the rDENV4/3 virus.

FIG. 7. Alignment of E glycoprotein sequences of dengue virus serotypes and other flaviviruses.

FIG. 8. Alignment of E glycoprotein sequences of dengue virus serotypes and chimeras thereof. DENV4 residues were implanted into the DENV2 E glycoprotein to generate the chimeras.

DETAILED DESCRIPTION OF THE INVENTION

Figure 1A:
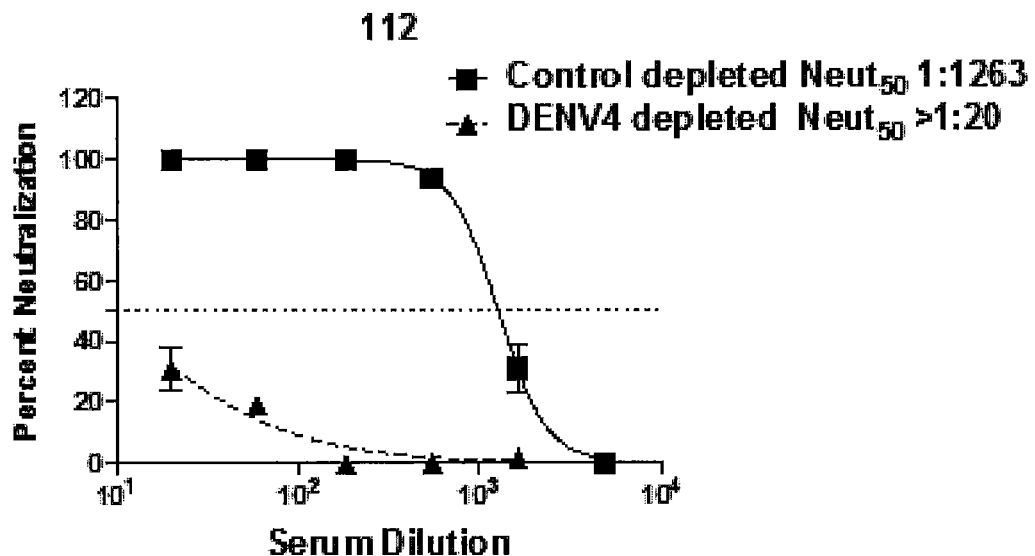
FIGS. 1A-1D. DENV4 is neutralized by type-specific antibodies in human primary immune and vaccine sera. A primary DENV4-immune sample 112 (FIG. 1A) and (FIG. 1B) and a DENV4 NIH monovalent vaccine sample 256.01.36 (FIG. 1C) and (FIG. 1D) were depleted of antibodies binding to DENV4 antigen (FIG. 1A) and (FIG. 1C) or DENV2 antigen (FIG. 1B) and (FIG. 1D). Control depletions were performed using bovine serum albumin as an antigen. Results presented here for antibody depletions are representative of data obtained with three primary DENV4 immune and four DENV4 monovalent vaccine sera (Table 2).
Figure 1B:
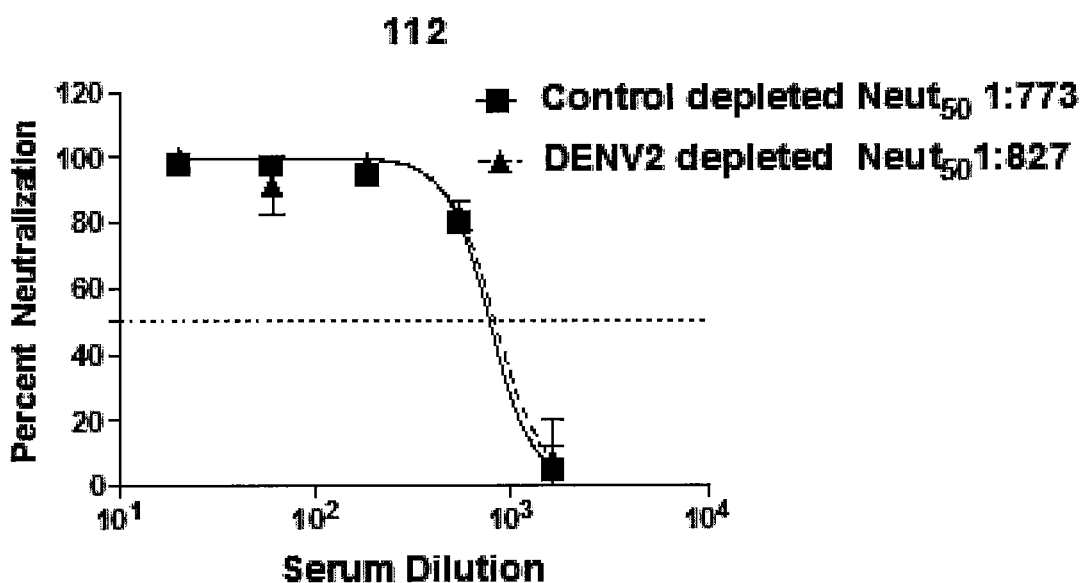
Figure 1C:
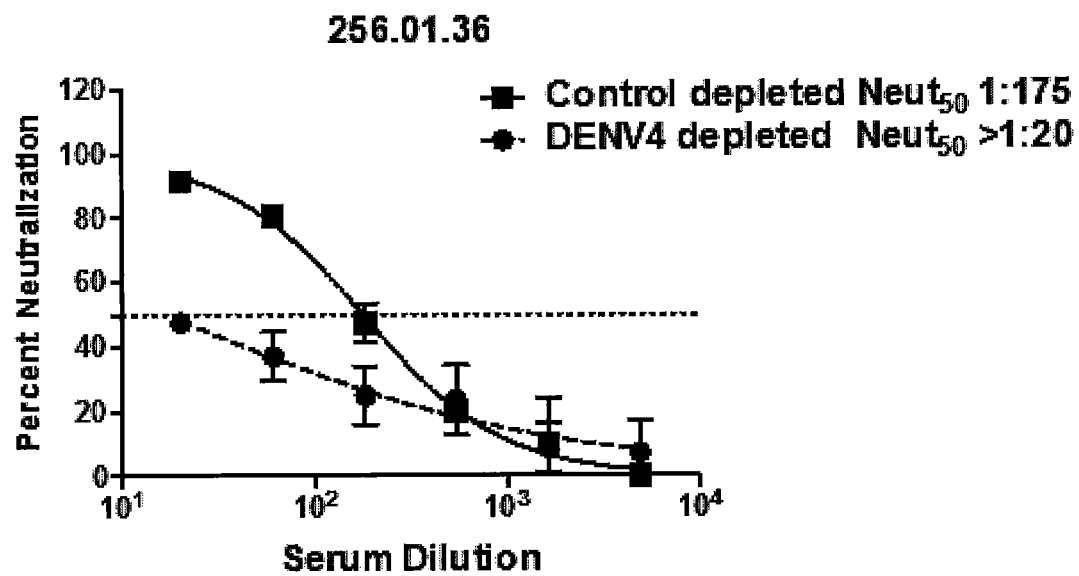
Figure 1D:
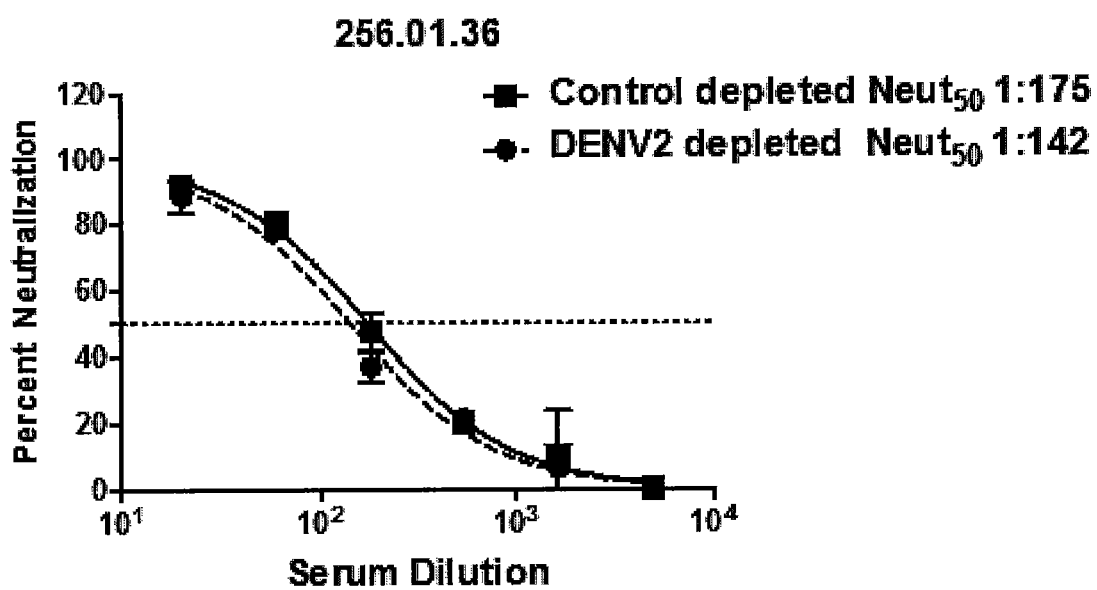

The present invention is based, in part on the unexpected discovery that amino acid residues that define an epitope specific for a particular DENV serotype can be transferred into the backbone amino acid sequence of a different DENV serotype to create chimeric molecules. Thus, in one embodiment, the present invention provides a chimeric dengue virus E glycoprotein comprising the amino acid sequence:

(SEQ ID NO: 5)
MRCVGIGNRDFVEGLSGATWVDVVLEHGSCVTTMAKDKPTLDIELLKTEV

KEVALLRTLCIEAKISNTTTDSRCPTQGEATLVEEQDTNFVCRRTFVDRG

WGNGCGLFGKGSLITCAKFKCVTKITGNLVQYENLKYSVIVTVHTGDQHQ

VGNETTEHGTTATITPQAPTSEIQLTDYGALTLDCSPRTGLDFNEMVLLK

MKKKTWLVHKQWFLDLPLPWTAGASTSQETWNRKDLLVTFKTAHAKKQEV

VVLGSQEGAMHTALTGATEVDSGDTTHMFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKK
(DENV1/4 M12).

The present invention further provides a chimeric dengue virus E glycoprotein comprising the amino acid sequence:

(SEQ ID NO: 6)
MRCVGIGNRDFVEGLSGATWVDVVLEHGSCVTTMAKDKPTLDIELLKTEV

KEVALLRTLCIEAKISNTTTDSRCPTQGEATLVEEQDTNFVCRRTFVDRG

WGNGCGLFGKGSLITCAKFSCSGKITGNLVQYENLKYSVIVTVHTGDQHQ

VGNETTEHGTTATITPQAPTSEIQLTDYGALTLDCSPRTGLDFNEMVLLK

MKKKTWLVHKQWFLDLPLPWTAGASTSEVHWNYKDLLVTFKTAHAKKQEV

VVLGSQEGAMHTALTGATEVDSGDTTHMFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKK
(DENV1/4 M14).

Also provided herein is a chimeric dengue virus E glycoprotein comprising the amino acid sequence:

(SEQ ID NO: 7)
MRCVGIGNRDFVEGLSGATWVDVVLEHGSCVTTMAKDKPTLDIELTKTTV

KEVALLRTLCIEASISNITTASRCPTQGEAYLKEEQDQQYICRRTFVDRG

WGNGCGLFGKGSLITCAKFSCSGKITGNLVQYENLKYSVIVTVHTGDQHQ

VGNETTEHGTTATITPQAPTSEIQLTDYGALTLDCSPRTGLDFNEMVLLK

MKKKTWLVHKQWFLDLPLPWTAGASTSEVHWNYKDLLVTFKTAHAKRQEV

TVLGSQEGAMHTALTGATEVDSGDTTHMFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKK
(DENV1/4 M-Complete).

In addition, the present invention provides a chimeric dengue virus E glycoprotein comprising the amino acid sequence:

(SEQ ID NO: 8)
MRCIGISNRDFVEGVSGGSWVDIVLEHGSCVTTMAKNKPTLDFELIKTEA

KEVALLRTYCIEAKLTNTTTESRCPTQGEPSLNEEQDKRFVCKHSMVDRG

WGNGCGLFGKGGIVTCAMFTCKKKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTQGSNWIQKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DGW107 E Protein small DV4 epitope swap - DENV 2/4 M12).

Further provided herein is a chimeric dengue virus E glycoprotein comprising the amino acid sequence:

(SEQ ID NO: 9)
MRCIGISNRDFVEGVSGGSWVDIVLEHGSCVTTMAKNKPTLDFELIKTEA

KEVALLRTYCIEAKLTNTTTESRCPTQGEPSLNEEQDKRFVCKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV 2/4 M14).

Additionally provided herein is a chimeric dengue virus E glycoprotein comprising the amino acid sequence:

(SEQ ID NO: 10)
MRCIGISNRDFVEGVSGGSWVDIVLEHGSCVTTMAKNKPTLDFELTKTTA

KEVALLRTYCIEASISNITTASRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKRQDV

TVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV 2/4 M complete).

In some embodiments, the chimeric dengue virus E glycoprotein comprising the amino acid sequence identified herein as DENV 2/4 M12 (SEQ ID NO:8), DENV 2/4 M14 (SEQ ID NO:9), and/or DENV 2/4 M complete (SEQ ID NO:10) can comprise additional substitutions (e.g., from the DENV 4 amino acid sequence) into the DENV 2 sequence at residues K64, E71 and/or K247. In some embodiments, the substitutions can be K64S, E71A and/or K247R. Additional amino acid sequences of this invention are included herein and in the attached SEQUENCE LISTING.

Further provided herein is a chimeric dengue virus E glycoprotein comprising the amino acid sequence:

(SEQ ID NO: 11)
MRCVGIGNRDFVEGLSGATWVDVVLEHGGCVTTMAKNKPTLDIELQKTEA

KEVALLRTLCIEGKITNITTDSRCPTQGEAVLPEEQDQNYVCKHTYVDRG

WGNGCGLFGKGSLVTCAKFQCLEKITGNLVQYENLKYTVIITVHTGDQHQ

VGNETQGVTAEITPQASTTEAILPEYGTLGLECSPRTGLDFNEMILLKMK

KKTWMVHRQWFFDLPLPWTAGATTETPTWNRKELLVTFKNAHAKKQEVVV

LGSQEGAMHTALTGATEVDSGDGTHMFAGHLKCRLKMDKLELKGMSYAMC

TNTFVLKKEVSETQHGTILIKVEYKGEDAPCKIPFSTEDGQKAHNGRLI

TANPVVTKKEEPVNIEAEPPFGESNIVIGIGDNALKINWYKK
(DENV3/4 M12).

The present invention also provides a chimeric dengue virus E glycoprotein comprising the amino acid sequence:

(SEQ ID NO: 12)
MRCVGIGNRDFVEGLSGATWVDVVLEHGGCVTTMAKNKPTLDIELQKTEA

KEVALLRTLCIEGKITNITTDSRCPTQGEAVLPEEQDQNYVCKHTYVDRG

WGNGCGLFGKGSLVTCAKFSCSGKITGNLVQYENLKYTVIITVHTGDQHQ

VGNETQGVTAEITPQASTTEAILPEYGTLGLECSPRTGLDFNEMILLKMK

KKTWMVHRQWFFDLPLPWTAGATTSEVHWNYKELLVTFKNAHAKKQEVVV

LGSQEGAMHTALTGATEVDSGDGTHMFAGHLKCRLKMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKK
(DENV3/4 M14).

A chimeric dengue virus E glycoprotein is also provided herein, comprising the amino acid sequence:

(SEQ ID NO: 13)
MRCVGIGNRDFVEGLSGATWVDVVLEHGCVTTMAKNKPTLDIELTKTTA

KEVALLRTLCIEGSISNITTASRCPTQGEAYLKEEQDQQYICKHTYVDRG

WGNGCGLFGKGSLVTCAKFSCSGKITGNLVQYENLKYTVIITVHTGDQHQ

VGNETQGVTAEITPQASTTEAILPEYGTLGLECSPRTGLDFNEMILLKMK

KKTWMVHKQWFFDLPLPWTAGATTSEVHWNYKELLVTFKNAHAKRQEVTV

LGSQEGAMHTALTGATEVDSGDGTHMFAGHLKCRLKMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKK
(DENV3/4 M-Complete).

Additional embodiments of the invention include an amino acid sequence:

(SEQ ID NO: 14)
MNNQRKKARNTPFNMLKRERNRVSTVQQLTKRFSLGMLQGRGPLKLFMAL

VAFLRFLTIPPTAGILKRWGTIKKSKAINVLRGFRKEIGRMLNILNRRRR

SAGMIIMLIPTVMAFHLTTRNGEPHMIVSRQEKGKSLLFKTEDGVNMCTL

MAMDLGELCEDTITYNCPLLRQNEPEDIDCWCNSTSTWVTYGTCTTTGEH

RREKRSVALVPHVGMGLETRTETWMSSEGAWKHAQRIETWILRHPGFTIM

AAILAYTIGTTHFQRALIFILLTAVAPSMTMRCIGISNRDFVEGVSGGSW

VDIVLEHGSCVTTMAKNKPTLDFELTKTTAKEVALLRTYCIEAKISNITT

ESRCPTQGEPYLKEEQDQQYICKHSMVDRGWGNGCGLFGKGGIVTCAKFS

CSGKITGNLVQPENLEYTIVVTPHSGEEHAVGNDTGKHGKEIKVTPQSSI

TEAELTGYGTVTMECSPRTGLDFNEMVLLKMKKKTWLVHKQWFLDLPLPW

TAGADTSEVHWNYKETLVTFKNPHAKKQDVTVLGSQEGAMHTALTGATEV

DSGDGNHMFAGHLKCRLRMDKLQLKGMSYSMCTGKFKVVKEIAETQHGTI

VIRVQYEGDGSPCKIPFEIMDLEKRHVLGRLITVNPIVTEKDSPVNIEAE

PPFGDSYIIIGVDPGQLKLNWFKKGSSIGQMFETTMRGAKRMAILGDTAW

DFGSLGGVFTSIGKALHQVFGAIYGAAFSGVSWTMKILIGVIITWIGMNS

RSTSLSVSLVLVGIVTLYLGVMVQADSGCVVSWKNKELKCGSGIFITDNV

HTWTEQYKFQPESPSKLASAIQKAQEEGICGIRSVTRLENLMWKQITPEL

-continued

NHILAENEVKLTIMTGDIKGIMQAGKRSLRPQPTELKYSWKTWGKAKMLS
TESHNQTFLIDGPETAECPNTNRAWNSLEVEDYGFGVFTTNIWLKLKEKQ
DAFCDSKLMSAAIKDNRAVHADMGYWIESALNDTWKIEKASFIEVKNCHW
PKSHTLWSNGVLESEMIIPKNLAGPVSQHNYRPGYHTQIAGPWHLGKLEM
DFDFCDGTTVVVTEDCGNRGPSLRTTTASGKLITEWCCRSCTLPPLRYRG
EDGCWYGMEIRPLKEKEENLVNSLVTAGHGQVDNFSLGVLGMALFLEEML
RTRVGTKHAILLVAVSFVTLITGNMSFRDLGRVVVMVGATMTDDIGMGVT
YLALLAAFKVRPTFAAGLLLRKLTSKELMMTTIGIVLLSQSTIPETILEL
TDALALGMMVLKMVRNMEKYQLAVTIMAILCVPNAVILQNAWKVSCTILA
VVSVSPLLLTSSQQKTDWIPLALTIKGLNPTAIFLTTLSRTSKKRSWPLN
EAIMAVGMVSILASSLLKNDIPMTGPLVAGGLLTVCYVLTGRSADLELER
AADVKWEDQAEISGSSPILSITISEDGSMSIKNEEEEQTLTILIRTGLLV
ISGLFPVSIPITAAAWYLWEVKKQRAGVLWDVPSPPPMGKAELEDGAYRI
KQKGILGYSQIGAGVYKEGTFHTMWHVTRGAVLMHKGKRIEPSWADVKKD
LISYGGGWKLEGEWKEGEEVQVLALEPGKNPRAVQTKPGLFRTNAGTIGA
VSLDFSPGTSGSPIIDKKGKVVGLYGNGVVTRSGAYVSAIAQTEKSIEDN
PEIEDDIFRKRRLTIMDLHPGAGKTKRYLPAIVREAIKRGLRTLILAPTR
VVAAEMEEALRGLPIRYQTPAIRAEHTGREIVDLMCHATFTMRLLSPVRV
PNYNLIIMDEAHFTDPASIAARGYISTRVEMGEAAGIFMTATPPGSRDPF
PQSNAPIIDEERE IPERSWNSGHEWVTDFKGKTVWFVPSIKAGNDIAACL
RKNGKKVIQLSRKTFDSEYVKTRTNDWDFVVTTDISEMGANFKAERVIDP
RRCMKPVILTDGEERVILAGPMPVTHSSAAQRRGRIGRNPKNENDQYIYM
GEPLENDEDCAHWKEAKMLLDNINTPEGIIPSMFEPEREKVDAIDGEYRL
RGEARKTFVDLMRRGDLPVWLAYKVAAEGINYADRRWCFDGIKNNQILEE
NVEVEIWTKEGERKKLKPRWLDARIYSDPLALKEFKEFAAGRKSLTLNLI
TEMGRLPTFMTQKARDALDNLAVLHTAEAGGRAYNHALSELPETLETLLL
LTLLATVTGGIFLFLMSGRGIGKMTLGMCCIITASILLWYAQIQPHWIAA
SIILEFFLIVLLIPEPEKQRTPQDNQLTYVVIAILTVVAATMANEMGFLE
KTKKDLGLGSIATQQPESNILDIDLRPASAWTLYAVATTFVTPMLRHSIE
NSSVNVSLTAIANQATVLMGLGKGWPLSKMDIGVPLLAIGCYSQVNPITL
TAALLLLVAHYAIIGPGLQAKATREAQKRAAAGIMKNPTVDGITVIDLDP
IPYDPKFEKQLGQVMLLVLCVTQVLMMRTTWALCEALTLATGPISTLWEG
NPGRFWNTTIAVSMANIFRGSYLAGAGLLFSIMKNTTNTRRGTGNIGETL
GEKWKSRLNALGKSEFQIYKKSGIQEVDRTLAKEGIKRGETDHHAVSRGS
AKLRWFVERNMVTPEGKVVDLGCGRGGWSYYCGGLKNVREVKGLTKGGPG
HEEPIPMSTYGWNLVRLQSGVDVFFIPPEKCDTLLCDIGESSPNPTVEAG
RTLRVLNLVENWLNNNTQFCIKVLNPYMPSVIEKMETLQRKYGGALVRNP
LSRNSTHEMYWVSNASGNIVSSVNMISRMLINRFTMRHKKATYEPDVDLG
SGTRNIGIESEIPNLDIIGKRIEKIKQEHETSWHYDQDHPYKTWAYHGSY
ETKQTGSASSMVNGVVRLLTKPWDVVPMVTQMAMTDTTPFGQQRVFKEKV
DTRTQEPKEGTKKLMKITAEWLWKELGKKKTPRMCTREEFTRKVRSNAAL

-continued

GAIFTDENKWKSAREAVEDSRFWELVDKERNLHLEGKCETCVYNMMGKRE
KKLGEFGKAKGSRAIWYMWLGARFLEFEALGFLNEDHWFSRENSLSGVEG
EGLHKLGYILRDVSKKEGGAMYADDTAGWDTRITLEDLKNEEMVTNHMEG
EHKKLAEAIFKLTYQNKVVRVQRPTPRGTVMDIISRRDQRGSGQVGTYGL
NTFTNMEAQLIRQMEGEGVFKNIQHLTVTEEIAVQNWLARVGRERLSRMA
ISGDDCVVKPLDDRFASALTALNDMGKIRKDIQQWEPSRGWNDWTQVPFC
SHHFHELIMKDGRVLVVPCRNQDELIGRARISQGAGWSLRETACLGKSYA
QMWSLMYFHRRDLRLAANAICSAVPSHWVPTSRTTWSIHAKHEWMTTEDM
LTVWNRVVVIQENPWMEDKTPVESWEEIPYLGKREDQWCGSLIGLTSRAT
WAKNIQAAINQVRSLIGNEEYTDYMPSMKRFRREEEEAGVLW (DENV2/4 M-Complete Modified Swap).

Some embodiments of the invention can include any portion, fragment, domain, N-terminal, C-terminal of SEQ ID NO:14. For example, some embodiments of the invention include a fragment of 10, 20, 30, 40, 50, 60, 70, 80, 90, 100, 110, 120, 130, 140, 150, 160, 170, 180, 190, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3,000 contiguous amino acids, including any values not explicitly recited herein. These fragments can be at either end and/or at any internal location in the amino acid sequence (e.g., residues 1-50 and/or residues 75-100).

Additional embodiments of the invention include an amino acid sequence:

(SEQ ID NO: 15)

MNNQRKKARNTPFNMLKRERNRVSTVQQLTKRFSLGMLQGRGPLKLFMAL
VAFLRFLTIPPTAGILKRWGTIKKSKAINVLRGFRKEIGRMLNILNRRRR
SAGMIIMLIPTVMAFHLTTRNGEPHMIVSRQEKGKSLLFKTEDGVNMCTL
MAMDLGELCEDTITYNCPLLRQNEPEDIDCWCNSTSTWVTYGTCTTTGEH
RREKRSVALVPHVGMGLETRTETWMSSEGAWKHAQRIETWILRHPGFTIM
AAILAYTIGTTHFQRALIFILLTAVAPSMTMRCIGISNRDFVEGVSGGSW
VDIVLEHGSCVTTMAKNKPTLDFELIKTEAKEVALLRTYCIEASISNITT
ATRCPTQGEPYLKEEQDQQYICRRDVVDRGWGNGCGLFGKGGVVTCAKFS
CSGKITGNLVQIENLEYTIVVTPHSGEEHAVGNDTGKHGKEIKVTPQSSI
TEAELTGYGTVTMECSPRTGLDFNEMILMKMKKKTWLVHKQWFLDLPLPW
TAGADTSEVHWNYKERMVTFKVPHAKRQDVTVLGSQEGAMHSALAGATEV
DSGDGNHMFTGHLKCRLRMDKLQLKGMSYSMCTGKFKVVKEIAETQHGTI
VIRVQYEGDGSPCKIPFEIMDLEKRHVLGRLITVNPIVTEKDSPVNIEAE
PPFGDSYIIIGVDPGQLKLNWFKKGSSIGQMFETTMRGAKRMAILGDTAW
DFGSLGGVFTSIGKALHQVFGAIYGAAFSGVSWTMKILIGVIITWIGMNS
RSTSLSVSLVLVGIVTLYLGVMVQADSGCVVSWKNKELKCGSGIFITDNV
HTWTEQYKFQPESPSKLASAIQKAQEEGICGIRSVTRLENLMWKQITPEL
NHILAENEVKLTIMTGDIKGIMQAGKRSLRPQPTELKYSWKTWGKAKMLS

-continued

```
TESHNQTFLIDGPETAECPNTNRAWNSLEVEDYGFGVFTTNIWLKLKEKQ

DAFCDSKLMSAAIKDNRAVHADMGYWIESALNDTWKIEKASFIEVKNCHW

PKSHTLWSNGVLESEMIIPKNLAGPVSQHNYRPGYHTQIAGPWHLGKLEM

DFDFCDGTTVVVTEDCGNRGPSLRTTTASGKLITEWCCRSCTLPPLRYRG

EDGCWYGMEIRPLKEKEENLVNSLVTAGHGQVDNFSLGVLGMALFLEEML

RTRVGTKHAILLVAVSFVTLITGNMSFRDLGRVVVMVGATMTDDIGMGVT

YLALLAAFKVRPTFAAGLLLRKLTSKELMMTTIGIVLLSQSTIPETILEL

TDALALGMMVLKMVRNMEKYQLAVTIMAILCVPNAVILQNAWKVSCTILA

VVSVSPLLLTSSQQKTDWIPLALTIKGLNPTAIFLTTLSRTSKKRSWPLN

EAIMAVGMVSILASSLLKNDIPMTGPLVAGGLLTVCYVLTGRSADLELER

AADVKWEDQAEISGSSPILSITISEDGSMSIKNEEEEQTLTILIRTGLLV

ISGLFPVSIPITAAAWYLWEVKKQRAGVLWDVPSPPPMGKAELEDGAYRI

KQKGILGYSQIGAGVYKEGTFHTMWHVTRGAVLMHKGKRIEPSWADVKKD

LISYGGGWKLEGEWKEGEEVQVLALEPGKNPRAVQTKPGLFRTNAGTIGA

VSLDFSPGTSGSPIIDKKGKVVGLYGNGVVTRSGAYVSAIAQTEKSIEDN

PEIEDDIFRKRRLTIMDLHPGAGKTKRYLPAIVREAIKRGLRTLILAPTR

VVAAEMEEALRGLPIRYQTPAIRAEHTGREIVDLMCHATFTMRLLSPVRV

PNYNLIIMDEAHFTDPASIAARGYISTRVEMGEAAGIFMTATPPGSRDPF

PQSNAPIIDEEREIPERSWNSGHEWVTDFKGKTVWFVPSIKAGNDIAACL

RKNGKKVIQLSRKTFDSEYVKTRTNDWDFVVTTDISEMGANFKAERVIDP

RRCMKPVILTDGEERVILAGPMPVTHSSAAQRRGRIGRNPKNENDQYIYM

GEPLENDEDCAHWKEAKMLLDNINTPEGIIPSMFEPEREKVDAIDGEYRL

RGEARKTFVDLMRRGDLPVWLAYKVAAEGINYADRRWCFDGIKNNQILEE

NVEVEIWTKEGERKKLKPRWLDARIYSDPLALKEFKEFAAGRKSLTLNLI

TEMGRLPTFMTQKARDALDNLAVLHTAEAGGRAYNHALSELPETLETLLL

LTLLATVTGGIFLFLMSGRGIGKMTLGMCCIITASILLWYAQIQPHWIAA

SIILEFFLIVLLIPEPEKQRTPQDNQLTYVVIAILTVVAATMANEMGFLE

KTKKDLGLGSIATQQPESNILDIDLRPASAWTLYAVATTFVTPMLRHSIE

NSSVNVSLTAIANQQATVLMGLGKGWPLSKMDIGVPLLAIGCYSQVNPITL

TAALLLLVAHYAIIGPGLQAKATREAQKRAAAGIMKNPTVDGITVIDLDP

IPYDPKFEKQLGQVMLLVLCVTQVLMMRTTWALCEALTLATGPISTLWEG

NPGRFWNTTIAVSMANIFRGSYLAGAGLLFSIMKNTTNTRRGTGNIGETL

GEKWKSRLNALGKSEFQIYKKSGIQEVDRTLAKEGIKRGETDHHAVSRGS

AKLRWFVERNMVTPEGKVVDLGCGRGGWSYYCGGLKNVREVKGLTKGGPG

HEEPIPMSTYGWNLVRLQSGVDVFFIPPEKCDTLLCDIGESSPNPTVEAG

RTLRVLNLVENWLNNNTQFCIKVLNPYMPSVIEKMETLQRKYGGALVRNP

LSRNSTHEMYWVSNASGNIVSSVNMISRMLINRFTMRHKKATYEPDVDLG

SGTRNIGIESEIPNLDIIGKRIEKIKQEHETSWHYDQDHPYKTWAYHGSY

ETKQTGSASSMVNGVVRLLTKPWDVVPMVTQMAMTDTTPFGQQRVFKEKV

DTRTQEPKEGTKKLMKITAEWLWKELGKKKTPRMCTREEFTRKVRSNAAL

GAIFTDENKWKSAREAVEDSRFWELVDKERNLHLEGKCETCVYNMMGKRE

KKLGEFGKAKGSRAIWYMWLGARFLEFEALGFLNEDHWFSRENSLSGVEG

EGLHKLGYILRDVSKKEGGAMYADDTAGWDTRITLEDLKNEEMVTNHMEG

EHKKLAEAIFKLTYQNKVVRVQRPTPRGTVMDIISRRDQRGSGQVGTYGL

NTFTNMEAQLIRQMEGEGVFKNIQHLTVTEEIAVQNWLARVGRERLSRMA

ISGDDCVVKPLDDRFASALTALNDMGKIRKDIQQWEPSRGWNDWTQVPFC

SHHFHELIMKDGRVLVVPCRNQDELIGRARISQGAGWSLRETACLGKSYA

QMWSLMYFHRRDLRLAANAICSAVPSHWVPTSRTTWSIHAKHEWMTTEDM

LTVWNRVWIQENPWMEDKTPVESWEEIPYLGKREDQWCGSLIGLTSRATW

AKNIQAAINQVRSLIGNEEYTDYMPSMKRFRREEEEAGVLW (DENV2/4/EDII Swap).
```

Some embodiments of the invention can include any portion, fragment, domain, N-terminal, C-terminal of SEQ ID NO:15. For example, some embodiments of the invention include a fragment of 10, 20, 30, 40, 50, 60, 70, 80, 90, 100, 110, 120, 130, 140, 150, 160, 170, 180, 190, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3,000 contiguous amino acids, including any values not explicitly recited herein. These fragments can be at either end and/or at any internal location in the amino acid sequence (e.g., residues 1-50 and/or residues 75-100).

Additional embodiments of the invention include a chimeric dengue virus E glycoprotein comprising the amino acid sequence:

```
                                        (SEQ ID NO: 22)
MRCIGISNRDFVEGVSGGSWVDIVLEHGSCVTTMAKNKPTLDFELTKTTA

KEVALLRTYCIEAKLTNTTTESRCPTQGEPSLNEEQDKRFVCKHSMVDRG

WGNGCGLFGKGGIVTCAKFSCSGKITGNLVQIENLEYTIVVTPHSGEEHA

VGNDTGKHGKEIKVTPQSSITEAELTGYGTVTMECSPRSGIDFNEMVLLK

MKKKTWLVHKQWFLDLPLPWTAGADTSEVHWNDKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV2/4 M14+).
```

Additional embodiments of the invention include a chimeric dengue virus E glycoprotein comprising the amino acid sequence:

```
                                        (SEQ ID NO: 23)
FHLTTRNGEPHMIVSRQEKGKSLLFKTEDGVNMCTLMAMDLGELCEDTIT

YNCPLLRQNEPEDIDCWCNSTSTWVTYGTCTTTGEHRREKRSVALVTHVG

MGLETRTETWMSSEGAWKHAQRIETWILRHPGFTIMAAILAYTIGTTHFQ

RALIFILLTAVAPSMT (prM protein for DENV2/4+ hinge).
```

Additional embodiments of the invention include a chimeric dengue virus E glycoprotein comprising the amino acid sequence:

(SEQ ID NO: 24)
MRCIGISNRDFVEGVSGGSWVDIVLEHGSCVTTMAKNKPTLDFELTKTTA

KEVALLRTYCIEAKISNITTESRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKKQDV

TVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV2/4 M-Complete Modified Swap).

Additional embodiments of the invention include a chimeric dengue virus E glycoprotein comprising the amino acid sequence:

(SEQ ID NO: 25)
MRCIGISNRDFVEGVSGGSWVDIVLEHGSCVTTMAKNKPTLDFELIKTEA

KEVALLRTYCIEASISNITTATRCPTQGEPYLKEEQDQQYICRRDVVDRG

WGNGCGLFGKGGVVTCAKFSCSGKITGNLVQIENLEYTIVVTPHSGEEHA

VGNDTGKHGKEIKVTPQSSITEAELTGYGTVTMECSPRTGLDFNEMILMK

MKKKTWLVHKQWFLDLPLPWTAGADTSEVHWNYKERMVTFKVPHAKRQDV

TVLGSQEGAMHSALAGATEVDSGDGNHMFTGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK
(DENV2/4/EDII Swap).

FIG. 8 is an alignment of the amino acid sequences of DENV2, DENV4 and the chimeras of this invention, showing the specific residues that are substituted in each amino acid sequence of the respective chimeras.

It is also contemplated that embodiments of this invention can include any fragment of the amino acid sequence of the chimeric E glycoprotein sequences provided herein. For example, some embodiments of the invention can include a fragment of any 10, 20, 30, 40, 50, 60, 70, 80, 90, 100, 110, 120, 130, 140, 150, 160, 170, 180, 190, 200, 250, 300 or 350 contiguous amino acids, including any values not explicitly recited herein. These fragments can be at either end and/or at any internal location in the amino acid sequence (e.g., residues 1-50 and/or residues 75-100).

The present invention also provides a nucleic acid molecule encoding the chimeric dengue virus E glycoprotein of this invention, a vector comprising the nucleic acid molecule of this invention, a flavivirus particle comprising the chimeric dengue virus E glycoprotein of this invention and/or the nucleic acid molecule of this invention, a virus like particle (VLP) comprising the chimeric dengue virus E glycoprotein of this invention, and a composition comprising the chimeric dengue virus E glycoprotein of this invention and/or the nucleic acid molecule of this invention, the vector of this invention, the flavivirus particle of this invention and/or the VLP of this invention, in a pharmaceutically acceptable carrier.

Further provided herein is a method of producing an immune response to a dengue virus in a subject, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

Also provided herein is a method of treating a dengue virus infection in a subject in need thereof, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

In a further embodiment, the present invention provides a method of preventing a dengue virus infection in a subject, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

Additionally provided herein is a method of protecting a subject from the effects of dengue virus infection, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

A method is also provided herein of detecting a neutralizing antibody to a dengue virus, the method comprising administering to the subject an effective amount of the chimeric dengue virus E glycoprotein of this invention, the nucleic acid molecule of this invention, the vector of this invention, the flavivirus particle of this invention, the VLP of this invention, the composition of this invention, and any combination thereof.

In addition, the present invention provides a method of identifying a neutralizing antibody to a dengue virus, comprising: (a) contacting an antibody with the E glycoprotein of this invention; and (b) determining if the antibody binds to the E glycoprotein, wherein binding by the antibody to the E glycoprotein identifies the antibody as a neutralizing antibody to a dengue virus.

Furthermore the present invention provides a method of identifying an immunogenic composition that induces a neutralizing antibody to a dengue virus in a subject, the method comprising: (a) contacting a biological sample from a subject that has been administered the immunogenic composition with the E glycoprotein of this invention; (b) determining if the biological sample comprises an antibody that binds the E glycoprotein; and (c) identifying the immunogenic composition as inducing a neutralizing antibody to a dengue virus in the subject if the biological sample comprises an antibody that binds to the E glycoprotein.

In another embodiment, the present invention provides a method of identifying an immunogenic composition that induces a neutralizing antibody to a dengue virus in a subject, the method comprising: (a) administering an immunogenic composition comprising a dengue virus antigen to a subject in an amount effective to induce antibodies against the dengue virus antigen; (b) contacting a biological sample from the subject with the E glycoprotein of the invention; (c) determining if the biological sample comprises an antibody that binds the E glycoprotein; and (d) identifying the immunogenic composition as inducing a neutralizing antibody to a dengue virus in the subject if the biological sample comprises an antibody that binds to the E glycoprotein.

In some embodiments, the flavivirus E glycoprotein backbone can be from any flavivirus, including but not limited to, yellow fever virus (YFV), Japanese encephalitis virus (JEV) or West Nile virus (WNV).

The present invention also provides a flavivirus particle or virus like particle (VLP) comprising the chimeric dengue virus E glycoprotein or chimeric flavivirus E glycoprotein of this invention.

In addition, the present invention provides an isolated nucleic acid encoding the chimeric dengue virus E glycoprotein or the chimeric flavivirus E glycoprotein of this invention, as well as an isolated nucleic acid encoding the isolated dengue virus epitope of this invention, an isolated nucleic acid encoding the polypeptide of this invention, an isolated nucleic acid encoding the flavivirus particle, VLP or viral coat of the chimeric flavivirus of this invention.

Further provided herein is a composition comprising the isolated dengue virus epitope this invention, the polypeptide of this invention, the chimeric VLP of this invention, the chimeric dengue virus E glycoprotein or chimeric flavivirus E glycoprotein of this invention, the flavivirus particle or VLP of this invention, the nucleic acid of this invention and any combination thereof, in a pharmaceutically acceptable carrier.

The term "dengue virus E protein domain I and domain II hinge region" and similar terms would be understood in the art to include the three-dimensional interface between domain I and II in the dengue virus E glycoprotein and, optionally, the adjacent amino acid residues. In addition, those skilled in the art will appreciate that certain amino acid residues in the hinge region may facilitate proper folding and presentation of the epitope, even if they do not form part of the epitope per se. In representative embodiments, the dengue virus E protein domain I and domain II hinge region comprises, consists essentially of, or consists of amino acid positions 47-59, 124-133, 199-222 and/or 206-228 of the E protein of dengue virus serotype 3 (DENV3; e.g., GenBank® Database Accession No. JQ411814) or the corresponding positions of the E protein of other dengue viruses (e.g., dengue virus serotype 1 (DENV1; e.g., GenBank® Database Accession No. U88535), serotype 2 (DENV2; e.g., GenBank® Database Accession No. NC_001474) or serotype 4 (DENV4); full E glycoprotein sequences are shown in FIGS. 7 and 8 and corresponding amino acid numbers are provided in Table 7).

The term "at least a portion of a dengue virus E protein domain III" and similar terms refer to those portions of E protein domain III that form part of the epitope as well as those amino acid residues that facilitate proper folding and presentation of the epitope, even if they do not form part of the epitope per se. In representative embodiments, the dengue virus E protein domain III comprises, consists essentially of, or consists of amino acid positions 305-308, 323-325, 359-362 and/or 389-390 of the E protein of dengue virus serotype 3 or the corresponding positions of the E protein of other dengue viruses (e.g., dengue virus serotypes 1 (DENV1), 2 (DENV2) or DENV4; full E glycoprotein sequences are shown in FIG. 7 and corresponding amino acid numbers are provided in Table 7). Likewise, in some embodiments, amino acid positions of the E protein of dengue serotype 2 (DENV2) were replaced with amino acid residues of dengue serotype 4 (DENV4) (FIG. 8).

In some embodiments, production of the chimera of this invention can be carried out by introducing some (e.g., 1, 2, 3, 4, 5, 6, 7, 8, 9, 10, etc.) or all of the amino acid substitutions identified in Table 7. Not every amino acid identified in Table 7 is required to be substituted to produce a chimeric protein of this invention. For example, in some embodiments further substitutions and/or omission of substitutions of about 1, 2, 3, 4 or 5 amino acids at either end of the contiguous amino acid sequences identified in Table 7 as the respective epitope regions can be included in production of a chimera of this invention. The number of substitutions necessary to produce the desired conformational epitope can be readily determined by one of ordinary skill in the art according to the teachings herein and according to protocols well known in the art.

In some embodiments, the present invention provides a chimeric flavivirus E glycoprotein in which amino acid substitutions are made to introduce a dengue virus epitope into a flavivirus E glycoprotein from a flavivirus that is not a dengue virus. Nonlimiting examples of flaviviruses that can be used include yellow fever virus (YFV) (e.g., GenBank® Database Accession No. JX503529) Japanese encephalitis virus (JEV) (e.g., GenBank® Database Accession No. U14163), West Nile virus (WNV) (e.g., GenBank® Database Accession No. DQ211652) and any other flavivirus now known or later identified. Thus, the present invention provides, for example a chimeric flavivirus E glycoprotein comprising a DENV1, DENV2, DENV3, or DENV4 domain I and domain II hinge region in a YFV, JEV or WNV E glycoprotein backbone. Also provided is a chimeric dengue virus E glycoprotein comprising a DENV1, DENV2, DENV3 or DENV4 domain I and domain II hinge region as well as a domain III region in a YFV, JEV or WNV E glycoprotein backbone.

In other embodiments, "at least a portion of a dengue virus E protein domain III" (and similar terms) comprises, consists essentially of, or consists of at least about 6, 8, 10, 12, 15, 20, 30, 40, 50, 60, 70, 80, 90 or 100 amino acids, optionally contiguous amino acids, and/or less than about 12, 15, 20, 30, 40, 50, 60, 70, 80, 90 or 100 amino acids, optionally contiguous amino acids, including any combination of the foregoing as long as the lower limit is less than the upper limit.

In representative embodiments, the peptide spacer comprises, consists of, or consists essentially of about 1, 2, 3 or less, 4 or less, 5 or less, 6 or less, 7 or less, 8 or less, 9 or less, 10 or less, 11 or less, 12 or less, 13 or less, 14 or less, 15 or less, 16 or less, 17 or less, 18 or less, 19 or less, 20 or less, 25 or less, 30 or less, 35 or less, 40 or less, 45 or less, 50 or less, 55 or less, 60 or less, 70 or less, 80 or less, 90 or less or 100 or less amino acids. In some embodiments, the peptide spacer comprises, consists of, or consists essentially of about 1 to about 5, 10, 15, 20, 25, 30, 35, 40, 45, 50, 55, 60, 70, 80, 90 or 100 amino acids. In some embodiments, the peptide spacer comprises, consists of, or consists essentially of about 3 to about 10, 15, 20, 25, 30, 35, 40, 45, 50, 55, 60, 70, 80, 90 or 100 amino acids. In some embodiments, the peptide spacer comprises, consists of, or consists essentially of about 4 to about 10, 15, 20, 25, 30, 35, 40, 45, 50, 55, 60, 70, 80, 90 or 100 amino acids. In some embodiments, the peptide spacer comprises, consists of, or consists essentially of about 5 to about 10, 15, 20, 25, 30, 35, 40, 45, 50, 55, 60, 70, 80, 90 or 100 amino acids. In some embodiments, the peptide spacer comprises, consists of, or consists essentially of about 10 to about 20, 25, 30, 35, 40, 45, 50, 55, 60, 70, 80, 90 or 100 amino acids. In some embodiments, the peptide spacer comprises, consists of, or consists essentially of about 15 to about 20, 25, 30, 35, 40, 45, 50, 55, 60, 70, 80, 90 or 100 amino acids. In some embodiments, the peptide spacer comprises, consists of, or consists essentially of about 20 to about 25, 30, 35, 40, 45, 50, 55, 60, 70, 80, 90 or 100 amino acids.

In some embodiments, the spacer brings the E protein domain I/II hinge region and the domain III region involved in the quaternary epitope about 10 or less, 15 or less, 20 or less, 25 or less, 30 or less, 35 or less, 40 or less, 45 or less, 50 or less, 60 or less or 70 or less angstroms apart. In some embodiments, the spacer brings the E protein domain I/II hinge region and the domain III region involved in the quaternary epitope about 10 to 20, 25, 30, 35, 40, 45, 50, 60 or 70 angstroms apart. In some embodiments, the spacer brings the E protein domain I/II hinge region and the domain III region involved in the quaternary epitope about 15 to 25, 30, 35, 40, 45, 50, 60 or 70 angstroms apart. In some embodiments, the spacer brings the E protein domain I/II hinge region and the domain III region involved in the quaternary epitope about 20 to 30, 35, 40, 45, 50, 60 or 70 angstroms apart. In some embodiments, the spacer brings the E protein domain I/II hinge region and the domain III region involved in the quaternary epitope about 25 to 35, 40, 45, 50, 60 or 70 angstroms apart. In embodiments, the spacer brings the E protein domain I/II hinge region and the domain III region involved in the quaternary epitope about 30 to 40, 45, 50, 60 or 70 angstroms apart. In some embodiments, the spacer brings the E protein domain I/II hinge region and the domain III region involved in the quaternary epitope about 35 to 45, 50, 60 or 70 angstroms apart.

The peptide spacer can be derived in whole or in part from a native E protein, or can be partially or wholly synthetic.

In some embodiments, the peptide spacer forms a secondary structure, e.g., a beta-sheet, beta-barrel and/or an alpha helical structure. In some embodiments, the peptide spacer comprises one or more disulfide bonds (e.g., cystine residues).

It is known in the art that many attempts to produce dengue virus vaccines result in the production of non-neutralizing antibodies, which may increase the likelihood of pathology upon subsequent exposure to natural infection or vaccine. Another approach to provide an engineered epitope is to deliver all or a portion of the dengue virus E protein incorporated into another flavivirus particle or VLP. In representative embodiments, the heterologous flavivirus can be West Nile virus or Yellow Fever virus. Portions of the E protein can be grafted into the E protein of the heterologous flavivirus backbone, e.g., to reduce the generation of non-neutralizing dengue virus antibodies to non-neutralizing epitopes present in the dengue virus E protein and/or other dengue virus structural proteins.

Thus, a chimeric flavivirus or chimeric flavivirus VLP can present the quaternary dengue virus epitope in proper conformation while reducing the generation of non-neutralizing antibodies to other portions of the dengue virus E protein and/or other structural proteins that are not presented in the chimeric flavivirus or flavivirus VLP.

Thus, as another aspect, the invention provides a chimeric flavivirus particle or chimeric flavivirus VLP comprising a chimeric flavivirus E protein, the chimeric flavivirus E protein comprising a dengue virus E protein domain I and domain II hinge region and at least a portion of the dengue virus E protein domain III. In embodiments of the invention, the dengue virus E protein region(s) are substituted for the corresponding region(s) of the heterologous flavivirus E protein. In embodiments, amino acid sequences from the dengue virus prM protein and/or the dengue virus C protein are not incorporated into the chimeric flavivirus or chimeric flavivirus VLP.

In some embodiments of the invention the individual and conformational epitopes of the flavivirus E glycoprotein or dengue virus E glycoprotein can be presented on a synthetic backbone or support structure so that the epitopes within the synthetic backbone or support structure mimic the conformation and arrangement of the epitopes within the structure of the E glycoprotein, virus particle or VLP.

In still further embodiments of the invention, the present invention provides peptide mimitopes (see, Meloen et al. (2000) *J. Mol. Recognit.* 13, 352-359) that mimic the individual and conformational epitopes of the E glycoproteins of the invention. Mimitopes may be identified using any technique known in the art, such as by surface stimulation, random peptide libraries or phage display libraries, using an antibody or antibodies to the individual and conformational epitopes of the E glycoproteins of the invention.

The invention further provides a nucleic acid molecule (e.g., isolated nucleic acid molecule) encoding a dengue virus epitope or a polypeptide of the invention.

The invention further provides a nucleic acid molecule (e.g., an isolated nucleic acid molecule) encoding a chimeric flavivirus VLP or a viral coat of a chimeric flavivirus particle of the invention.

Also provided are vectors encoding the nucleic acid molecules of the invention.

Also provided are cells comprising the vectors, nucleic acid molecules, dengue virus epitopes, polypeptides, chimeric flavivirus VLPs or chimeric flavivirus particles of the invention.

The invention also provides immunogenic compositions comprising the cells, vectors, nucleic acid molecules, dengue virus epitopes, polypeptides, chimeric flavivirus VLPs or chimeric flavivirus particles of the invention. In some embodiments, the immunogenic composition is monovalent. In some embodiments, the immunogenic composition is multivalent (e.g., tetravalent) for dengue virus serotypes DEN1, DEN2, DEN 3 and/or DEN4.

The invention encompasses methods of producing an immune response to a dengue virus in a subject, the method comprising administering to the subject an effective amount of a dengue virus epitope, a polypeptide, a chimeric flavivirus VLP or chimeric flavivirus particle, nucleic acid, vector, cell or immunogenic composition of the invention.

Further, the present invention can advantageously be practiced to induce an immune response against one, two, three or all four of DEN1, DEN2, DEN3 and DEN4. It is well-known in the art that effective and safe multivalent dengue vaccines have been a challenge to design because of the problem of interference among serotypes. For example, the immune response may be predominantly directed against only some of the target serotypes. Multiple vaccinations are then required to try to achieve a response against all serotypes; however, in the case of dengue virus, this approach can be dangerous because repeated administrations to a subject with pre-existing antibodies can lead to dengue hemorrhagic fever.

A still further aspect of the invention is a method of treating a dengue virus infection, comprising administering to the subject an effective amount of a dengue virus epitope, a polypeptide, a chimeric flavivirus VLP or chimeric flavivirus particle, nucleic acid molecule, vector, cell, or immunogenic composition of the invention.

A still further aspect of the invention is a method of preventing a dengue virus infection, comprising administering to the subject an effective amount of a dengue virus epitope, a polypeptide, a chimeric flavivirus VLP or chimeric flavivirus particle, nucleic acid molecule, vector, cell, or immunogenic composition of the invention.

A still further aspect of the invention is a method of protecting a subject from the effects of dengue virus infection, comprising administering to the subject an effective amount of a dengue virus epitope, a polypeptide, a chimeric flavivirus VLP or chimeric flavivirus particle, nucleic acid, vector, cell, or immunogenic composition of the invention.

The invention can also be practiced to identify antibodies that bind (e.g., specifically bind) to the quaternary dengue virus epitope, e.g., to identify neutralizing antibodies to a dengue virus. For example, the invention can be employed as a diagnostic to qualitatively determine if a vaccine candidate is inducing neutralizing antibodies. In general, due to the abundance of non-neutralizing antibodies induced by many candidate dengue virus vaccines, antibody titers alone without further characterization of the antibody specificity provides incomplete information.

In representative embodiments, the invention provides a method of detecting a neutralizing antibody to a dengue virus, the method comprising the step of determining whether an antibody binds to a dengue virus epitope, a polypeptide, or a chimeric VLP or chimeric flavivirus of the invention, wherein binding by the antibody to the dengue virus epitope, the polypeptide, the chimeric VLP or the chimeric flavivirus indicates that the antibody is a neutralizing antibody to a dengue virus.

In further representative embodiments, the invention provides a method of identifying a neutralizing antibody to a dengue virus, the method comprising: (a) contacting an antibody to a dengue virus epitope, a polypeptide, or a chimeric VLP or chimeric flavivirus of the invention; and (b) determining if the antibody binds to the dengue virus epitope, the polypeptide, the chimeric VLP or the chimeric flavivirus; wherein binding by the antibody to the dengue virus epitope, the polypeptide, the chimeric VLP or the chimeric flavivirus indicates that the antibody is a neutralizing antibody to a dengue virus.

The invention also provides a method of identifying a neutralizing antibody to a dengue virus, the method comprising: (a) contacting an antibody to a dengue virus epitope, a polypeptide, or a chimeric VLP or chimeric flavivirus of the invention; (b) determining if the antibody binds to the dengue virus epitope, the polypeptide, the chimeric VLP or the chimeric flavivirus; and (c) identifying the antibody as a neutralizing antibody to a dengue virus if the antibody binds to the dengue virus epitope, the polypeptide, the chimeric VLP or the chimeric flavivirus.

Still further, the invention provides a method of identifying an immunogenic composition that induces a neutralizing antibody to a dengue virus in a subject, the method comprising the step of determining whether a biological sample obtained from a subject that has been administered the immunogenic composition comprises an antibody that binds to a dengue virus epitope, a polypeptide, or a chimeric VLP or chimeric flavivirus of the invention, wherein if the biological sample comprises an antibody that binds to the dengue virus epitope, the polypeptide, the chimeric VLP or the chimeric flavivirus, it indicates that the immunogenic composition induces a neutralizing antibody to a dengue virus in the subject.

The invention also provides a method of identifying an immunogenic composition that induces a neutralizing antibody to a dengue virus in a subject, the method comprising: (a) contacting a biological sample from a subject that has been administered the immunogenic composition with a dengue virus epitope, a polypeptide, or a chimeric VLP or chimeric flavivirus of the invention; and (b) determining if the biological sample comprises an antibody that binds to the dengue virus epitope, the polypeptide, the chimeric VLP or the chimeric flavivirus; wherein if the biological sample comprises an antibody that binds to the dengue virus epitope, the polypeptide, the chimeric VLP or the chimeric flavivirus, it indicates that the immunogenic composition induces a neutralizing antibody to a dengue virus in the subject.

In yet another embodiment, the invention provides a method of identifying an immunogenic composition that induces a neutralizing antibody to a dengue virus in a subject, the method comprising: (a) contacting a biological sample from a subject that has been administered the immunogenic composition with a dengue virus epitope, a polypeptide, or a chimeric VLP or chimeric flavivirus of the invention; (b) determining if the biological sample comprises an antibody that binds to the dengue virus epitope, the polypeptide, the chimeric VLP or the chimeric flavivirus; and (c) identifying the immunogenic composition as inducing a neutralizing antibody to a dengue virus in the subject if the biological sample comprises an antibody that binds to the dengue virus epitope, the polypeptide, the chimeric VLP or the chimeric flavivirus.

In other representative embodiments, the invention provides a method of identifying an immunogenic composition that induces a neutralizing antibody to a dengue virus in a subject, the method comprising: (a) administering an immunogenic composition comprising a dengue virus antigen to a subject in an amount effective to induce antibodies against the dengue virus antigen; (b) contacting a biological sample from the subject with a dengue virus epitope, a polypeptide, or a chimeric VLP or chimeric flavivirus of the invention; (c) determining if the biological sample comprises an antibody that binds to the dengue virus epitope, the polypeptide, the chimeric VLP or chimeric flavivirus; and (d) identifying the immunogenic composition as inducing a neutralizing antibody to a dengue virus in the subject if the biological sample comprises an antibody that binds to the dengue virus epitope, the polypeptide, the chimeric VLP or the chimeric flavivirus.

There are four serotypes of dengue virus (DEN1, DEN2, DEN3 and DEN4). Within each serotype there are a number of different strains or genotypes. The dengue virus antigens and epitopes of the invention can be derived from any dengue virus, including all serotypes, strains and genotypes, now known or later identified.

In embodiments of the invention, the dengue virus is UNC1017 strain (DEN1), West Pacific 74 strain (DEN1), S16803 strain (DEN2), UNC2005 strain (DEN2), UNC3001 strain (DEN3), UNC3043 (DEN3 strain 059.AP-2 from Philippines, 1984), UNC3009 strain (DEN3, D2863, Sri Lanka 1989), UNC3066 (DEN3, strain 1342 from Puerto Rico 1977), CH53489 strain (DEN3), UNC4019 strain (DEN4), or TVP-360 (DEN4).

In embodiments of the invention, an "immunogenically active fragment" of a dengue virus polypeptide (e.g., the E protein, or the EDI, EDII or EDIII domain) comprises, consists essentially of or consists of at least about 6, 8, 10, 12, 15, 20, 30, 50, 75, 100, 125, 150, 200, 250, 300, 350, 400, 450 or more amino acids, optionally contiguous amino acids, and/or less than about 495, 475, 450, 425, 400, 350, 300, 250, 200, 150, 100, 75 or 50 amino acids, optionally contiguous amino acids, including any combination of the foregoing as long as the lower limit is less than the upper limit, and the "immunogenically active fragment" induces an immune response (e.g., IgG and/or IgA that react with the native antigen), optionally a protective immune response, against dengue virus in a host and induces the production of antibodies that specifically bind to the quaternary dengue virus epitope newly identified by the inventors.

The term "epitope" as used herein means a specific combination of amino acid residues in an amino acid sequence that, when present in the proper conformation, provides a reactive site for an antibody (e.g., B cell epitope) or T cell receptor (e.g., T cell epitope).

Portions of a given polypeptide that include a B-cell epitope can be identified using any number of epitope mapping techniques that are known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci.* USA 81:3998-4002; Geysen et al. (1986) *Molec. Immunol.* 23:709-715.

Similarly, conformational epitopes can be readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenically active fragments can also be identified based on their ability to stimulate lymphocyte proliferation in response to stimulation by various fragments from the antigen of interest.

The present invention can be practiced for prophylactic, therapeutic and/or diagnostic purposes. In addition, the invention can be practiced to produce antibodies for any purpose, such as diagnostic or research purposes, or for passive immunization by transfer to another subject.

The present invention further provides a kit comprising one or more compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

Administration to a subject can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous (including administration into the footpad), intradermal, intrapleural, intracerebral, and/or intrathecal routes.

The epitopes, polypeptides, VLPs and viral vectors of the invention can be delivered per se or by delivering a nucleic acid (e.g., DNA) that encodes the same.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, a viral adjuvant expresses the cytokine.

In embodiments of the invention, multiple dosages (e.g., two, three or more) of a composition of the invention can be administered without detectable pathogenicity (e.g., Dengue Shock Syndrome/Dengue Hemorrhagic Fever).

In embodiments of the invention, the multivalent vaccines of the invention do not result in immune interference, e.g., a balanced immune response is induced against all antigens presented. In embodiments of the invention, the balanced response results in protective immunity against DEN1, DEN2, DEN3 and DEN4.

In embodiments of the invention, the multivalent vaccine can be administered to a subject that has anti-dengue maternal antibodies present.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03.

Thus, the term "consisting essentially of" when used in a claim of this invention is not intended to be interpreted to be equivalent to "comprising."

As used herein, the terms "nucleic acid" or "nucleic acid molecule" encompass both RNA and DNA, including cDNA, genomic DNA, synthetic (e.g., chemically synthesized) DNA and chimeras of RNA and DNA. The nucleic acid molecule may be double-stranded or single-stranded. The nucleic acid molecule may be synthesized using nucleotide analogs or derivatives (e.g., inosine or phosphorothioate nucleotides). Such nucleotides can be used, for example, to prepare nucleic acid molecules that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame. A fusion protein can also comprise two or more heterologous amino acid sequences connected or linked by a spacer or linker amino acid sequence.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of dengue virus infection.

"Effective amount" as used herein refers to an amount of a vector, nucleic acid, epitope, polypeptide, cell, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the term "treat,", "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing dengue virus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating dengue virus infection in a subject, whether against one or multiple strains, genotypes or serotypes of dengue virus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to dengue virus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by dengue virus. Alternatively, a subject according to the invention can also include a subject not previously known or suspected to be infected by dengue virus or in need of treatment for dengue virus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

In embodiments of the invention, the subject has maternal antibodies to dengue virus.

A "subject in need" of the methods of the invention (e.g., a subject in need thereof) can be a subject known to be, or suspected of being, infected with, or at risk of being infected with, dengue virus.

Pharmaceutical formulations (e.g., immunogenic formulation) comprising the dengue virus epitopes, polypeptides, chimeric flavivirus VLPs or chimeric flavivirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., Vaccine 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829, which is hereby incorporated by reference in its entirety.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science And Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10% by weight. The surfactant is generally nontoxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5% by weight. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729, which is hereby incorporated by reference in its entirety. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 µg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

In embodiments of the invention, the dosage of a virus particle of this invention can be in a range of about $10^4$ to about $10^7$ plaque forming units (PFUs). In embodiments of this invention, the dosage of a VLP of this invention can be in a range of about 500 micrograms to about 5 milligrams. In embodiments of this invention, the dosage of a protein of this invention can be in a range of about $10^0$ to about $10^4$ micrograms+/−adjuvant.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

EXAMPLES

Example 1

Dengue virus is an important human pathogen responsible for considerable morbidity and mortality worldwide. Four DENV serotypes circulate worldwide and vaccines must protect against each serotype. Current vaccines under development or on the market are tetravalent live virus attenuated vaccines containing the E and the prM glycoproteins of each serotype DENV1-4. However in humans, many vaccines elicit unbalanced responses, especially concerning as current vaccines elicit weak immune responses to either DENV 2 or DENV 4. Consequently, a new strategy is needed to enhance the immune response simultaneously to both DENV 2 and DENV 4 in a balanced formulation. The DENV E glycoprotein forms a dimer and is divided into three discrete domains designated EDI, EDII and EDIII. The major DENV4 neutralizing sites are encoded by human monoclonal antibodies hm126 and hm131. The goal of these studies was to use reverse genetics to build recombinant chimeric viruses that encode the major neutralizing epitopes of DENV2 and DENV4 in the same recombinant virus. This new chimeric virus is designed to enhance the response to DENV 4 neutralizing epitopes presented in the context of the DENV2 E glycoprotein, while maintaining functional neutralizing epitopes that elicit robust immune responses against DENV 2.

Using serotype specific antibodies to guide immunogen design, we have made chimeric dengue viruses that contain neutralizing epitopes from both of the 2 different serotypes in a single virus. To accomplish this, we present the structure of the DENV E glycoprotein, which forms a dimer that assembles into 30 larger rafts composed of three dimers of E protein. Consequently, a total of 180 E proteins cover the surface of each dengue virus particle. Importantly, DENV2 neutralizing monoclonals 2D22 and 3F9 have been shown to specifically neutralize DENV 2 and their quaternary epitopes have been determined to lie mainly on domains EDI and EDIII respectively of the E protein. DENV 4 has been shown to be specifically neutralized by monoclonals hmAB126 and hmAB131 which primarily bind across dimers on EDII. We designed recombinant DENV2/4 chimeras by insertion of residues that reconstitute DENV4 neutralizing antibody sites 126/131 in DENV2 (M12) encodes residues of hmAB 126 epitope and M14 encodes residues for hmAB126 and hmAB 131). The combined epitopes of hmAB126 and hmAB131 can be transplanted from DENV 4 to DENV 2 by changing those variable amino acids of DENV 2 into residues encoded by DENV 4 for that specific area of the E protein. We have designed DENV 2/4 viruses with transplants of increasing size; DENV 2/4 M12 (SEQ ID NO:8), DENV 2/4 M14 (SEQ ID NO:9) and DENV 2/4 M Complete (SEQ ID NO:10) (Table 5), simply by moving residues from DENV4 into DENV2. The smallest, DENV M12, converts only a small area of DENV 2 into DENV 4, encoding the hm126 antibody epitope. This virus can be used to measure DENV 4 specific antibodies to this single epitope in polyclonal sera. DENV M14 reconstructs both DENV4 hm126 and hm131 targeted epitopes into DENV 2. The largest, DENV 2/4 M complete (SEQ ID NO:10), converts nearly all of domain 2 into DENV 4. This final design incorporates new features into epitope exchange by taking into consideration the interactions between the E proteins both within each dimers and then between dimers encoded in the larger rafts. The impact is potentially profound as this approach captures the larger antigenic site while stabilizing interactions within and between dimers of the larger raft, enhancing stability and recombinant virus viability. Since ED1 and EDIII occur in an alternating pattern on the virus surface and are adjacent to other EDI and EDIII domains, this forms a large surface area that is solely DENV 2. In contrast, EDII mostly boarders other EDII encoding monomers and thus forms a large contiguous surface area of DENV4 residues made of 6 EDIIs that run down the center of the larger raft. Since contiguous areas and borders present critical epitopes of DENV4 and DENV2, this approach has the potential to increase the stability of the chimeric virus. This virus may be used in a vaccine to simultaneously immunize people against both DENV 2 and DENV 4 because it contains immune dominant epitopes from both viruses. The DENV 2/4 M Complete (SEQ ID NO:10), encoding the largest DENV4 epitope transplant, has been electroporated into Vero cells and produced virus that is recognizable by dengue monoclonal antibodies. In addition, DENV 1/4 viruses (Table 4) and DENV 3/4 viruses (Table 6) with transplants of increasing size were prepared in an analogous manner.

In summary, we have designed DENV 2/4 viruses with small to large DENV4 epitope transplants. The viruses with small transplants can be used to precisely map antibody responses to each epitope and combined antigenic site in polyclonal sera. The DENV 2/4 M Complete (SEQ ID NO:10) virus with the largest transplant is a good vaccine candidate, because it carries the immune dominate epitopes in a format most similar to that seen in the native virus and, thus, may be best able to present these epitopes to the immune system of the largest variety of people. In addition, these viruses may have increased stability, which could make them useful vaccine candidates.

Example 2

The four serotypes of dengue virus are the causative agents of dengue fever and dengue hemorrhagic fever. People exposed to primary DENV infections develop long-term neutralizing antibody responses principally only to the infecting serotype. An effective vaccine against dengue needs to elicit long lasting protective antibody responses to all four serotypes simultaneously. We and others have defined antigenic sites on the envelope (E) protein of viruses of dengue serotypes 1, 2 and 3 targeted by human neutralizing antibodies. The mechanisms of serotype 4 neutralization by human antibodies are poorly understood. Here, we report on the properties of human antibodies that neutralize dengue serotype 4. People exposed to serotype 4 infections or a live attenuated serotype 4 vaccine developed strongly neutralizing antibodies that bound to similar sites on the viral E protein. These studies provide a foundation for developing and evaluating DENV4 vaccines.

DENV4 is Neutralized by Type-Specific Antibodies in Human Immune Serum

To study the properties of serum polyclonal DENV4 neutralizing human antibodies, we assembled a panel of blood samples from people exposed to DENV4 infections or people who had received a monovalent live-attenuated DENV4 vaccine (Table 1).

Individuals exposed to DENV have specific antibodies in circulation as well as DENV-specific memory B cells (MBCs). Some of the dengue specific antibodies in circulation bind only to viruses of the serotype of infection (type-specific), while others cross-react with two or more serotypes. Using serum samples from people exposed to DENV4 natural infections or a monovalent live-attenuated DENV4 vaccine, we performed antibody depletion studies to determine the relative contributions of serotype cross-reactive and type-specific antibodies to DENV4 neutralization. Polystyrene beads coated with the homotypic (DENV4) or heterotypic (DENV2) DENV serotypes were incubated with the immune serum samples to deplete specific populations of antibodies. Depletion of DENV4 or DENV2 binding antibodies was confirmed by ELISA before using the samples in DENV4 neutralization assays. Depleting the DENV4 immune serum samples with the homotypic DENV4 antigen led to the removal of nearly all the DENV-specific (serotype cross-reactive and DENV4 type-specific antibodies) antibodies in the sample. As anticipated, depleting with DENV4 antigen led to a large drop in DENV4 neutralizing antibodies in both DENV4 infection and vaccine sera (FIGS. 1A-1D and Table 2). Depleting DENV4 immune sera with heterotypic DENV2 antigen led to the removal of serotype cross reactive but not DENV4 type-specific antibodies. There was minimal to no loss in neutralization of DENV4 in sera depleted with DENV2 antigen (FIGS. 1A-1D and Table 2). These results demonstrate that type-specific antibodies were mainly responsible for DENV4 neutralization in primary infection and monovalent DENV4 vaccination serum samples.

Isolation of DENV4 Neutralizing Human Monoclonal Antibodies

To further characterize the B cell response to DENV4, we transformed B cells from two DENV4 immune individuals (subjects 002 and 112) and isolated human monoclonal antibodies (hMAbs), as previously described. The transformed B cell culture supernatants were screened for binding to DENV4. Based on the number of positive wells and the number of transformed B cells tested (determined by average colony counts in transformed wells), the frequency of DENV-specific B cells in circulation was estimated to be 0.19 and 0.2% of transformable B cells for subjects 002 and 112, respectively. Previously, it was reported that there may be a long-term set point frequency of 0.1-0.2% DENV specific B cells in the circulating memory B cell pool following DENV infection, and the frequencies of 0.19 and 0.2% in the two subjects studied here are consistent with these previous reports.

Figure 2A:
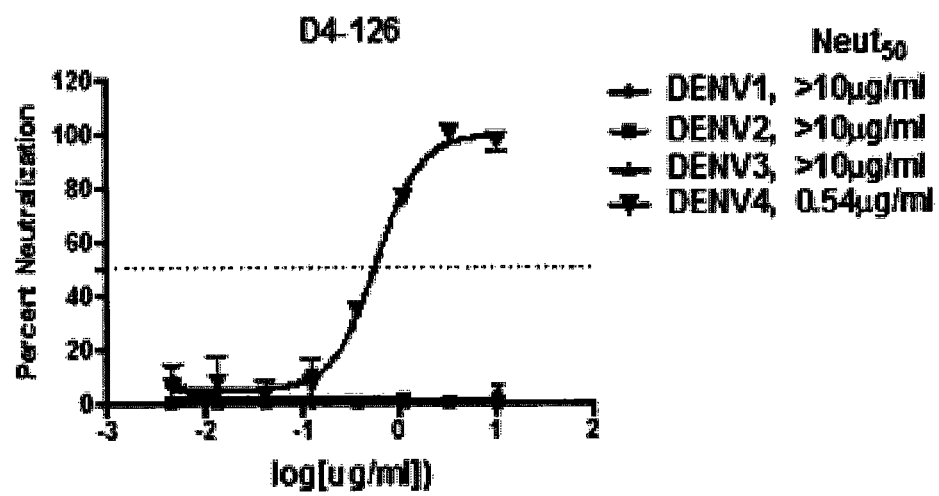
FIGS. 2A-2B. Properties of DENV4 neutralizing human monoclonal antibodies D4-126 and D4-131.
Figure 2A:
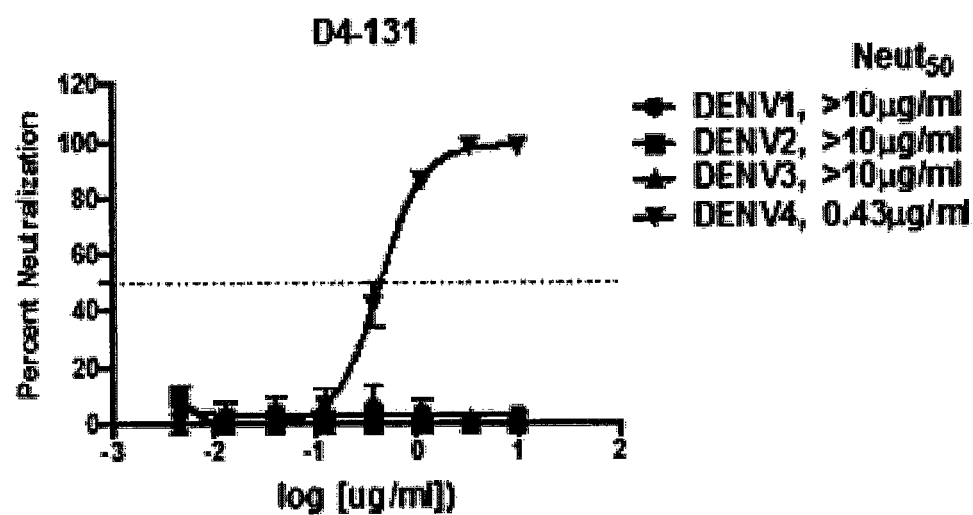
Figure 2B:
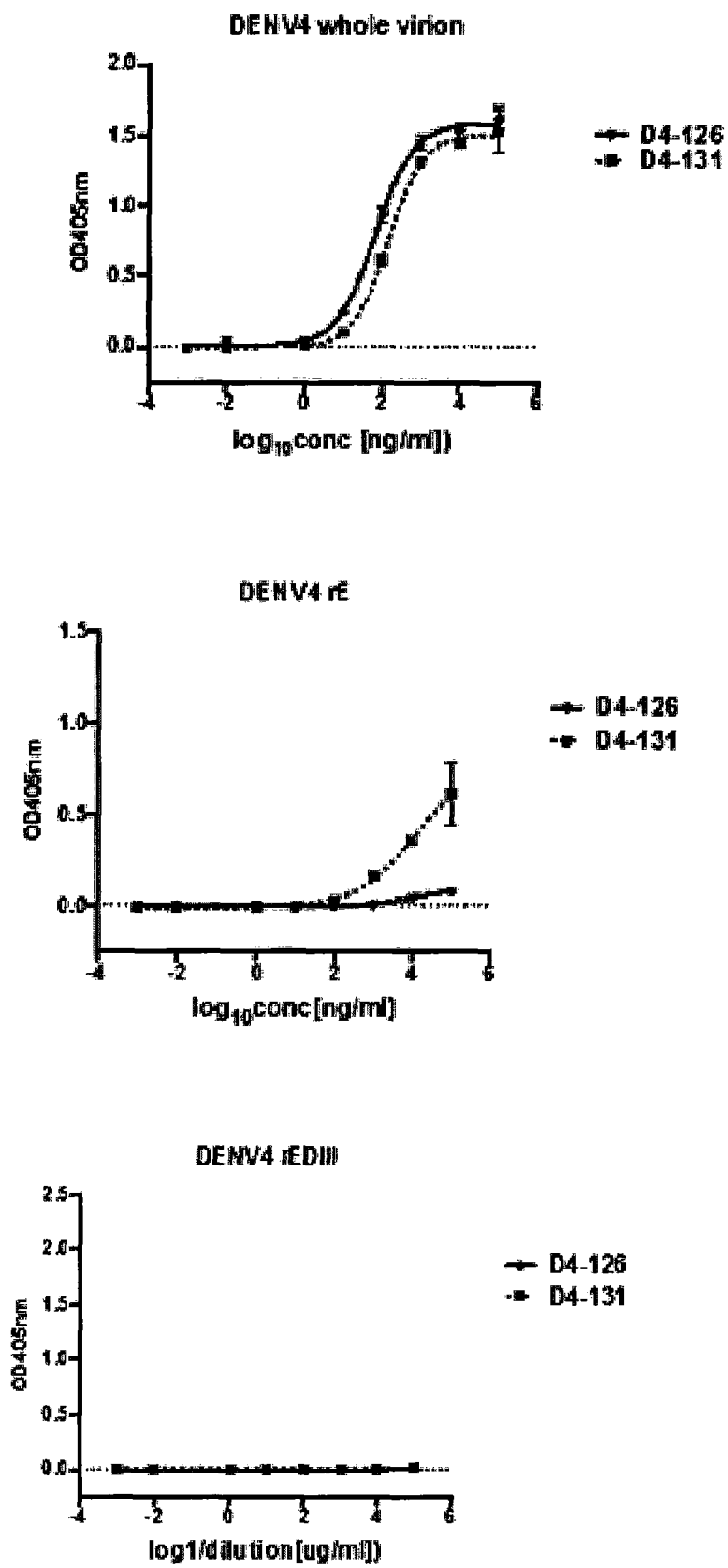

We also determined the DENV serotype specificity of all the positive B cell culture supernatants from subject 112. Of the 34 DENV antigen-reactive supernatants, antibodies in 32% bound only to DENV4 (type-specific) and in 68% bound to two or more serotypes (cross-reactive). From the EBV-transformed B cell lines secreting DENV antigen-reactive antibodies, we isolated 8 human B cell hybridoma cell lines, as previously described. Two lines, designated D4-126 or D4-131, secreted DENV4 type-specific and strongly neutralizing MAbs with neut$_{50}$ values of 0.54 µg/mL or 0.43 µg/mL, respectively (FIG. 2A). To characterize the binding properties of D4-126 and D4-131 MAbs further, we performed binding assays with whole DENV4 virions, rE or rEDIII proteins of DENV4 and increasing concentrations of hMAbs D4-126 or D4-131. Both hMAbs bound to whole DENV4 virus particles similarly (FIG. 2B). HMAb D4-126 did not bind to rE protein, whereas D4-131 exhibited low levels of binding to rE protein at high concentrations (>10 µg/mL) (FIG. 2B). The hMAbs did not bind to rEDIII protein (FIG. 2B). These studies revealed that neutralizing hMAbs D4-126 and D4-131 bound best to intact DENV4 virions.

HMAb Neutralization of Different DENV4 Strains

Figure 3A:
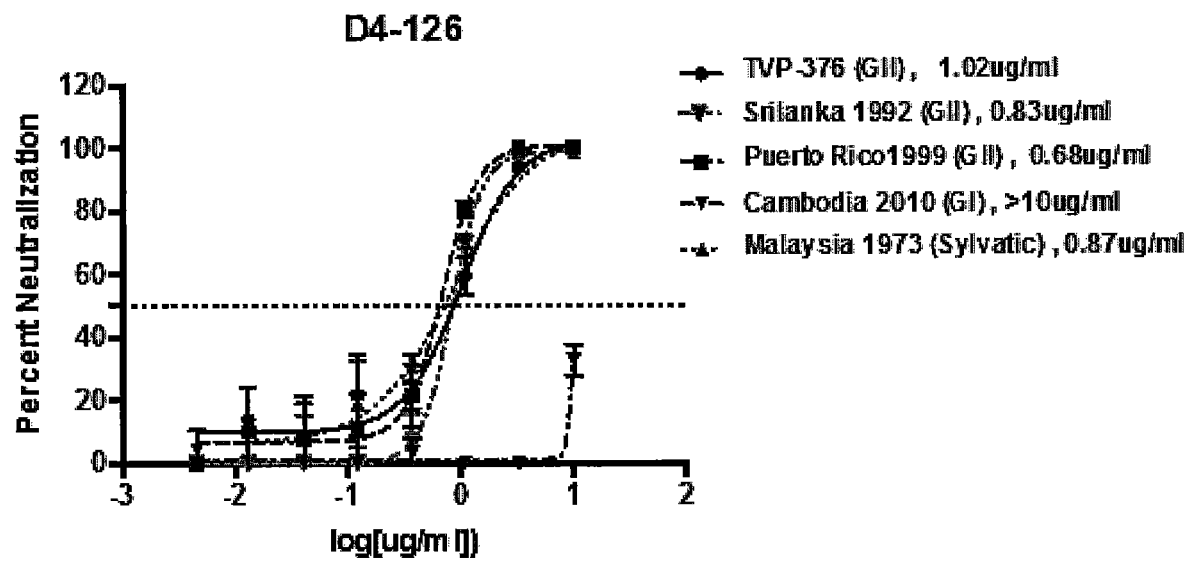
FIGS. 3A-3B. Neutralization of different DENV4 strains by hMAbs D4-126 and D4-131. U937+DC-SIGN flow based neutralization assays were conducted to compare the ability of D4-126 (FIG. 3A) and D4-131 (FIG. 3B) hMAbs to neutralize different laboratory adapted and clinical strains of DENV4. The MAbs neutralized all variants except for the Cambodia 2010 genotype I strain, which was not neutralized by D4-126 and weakly neutralized by D4-131.
Figure 3B:
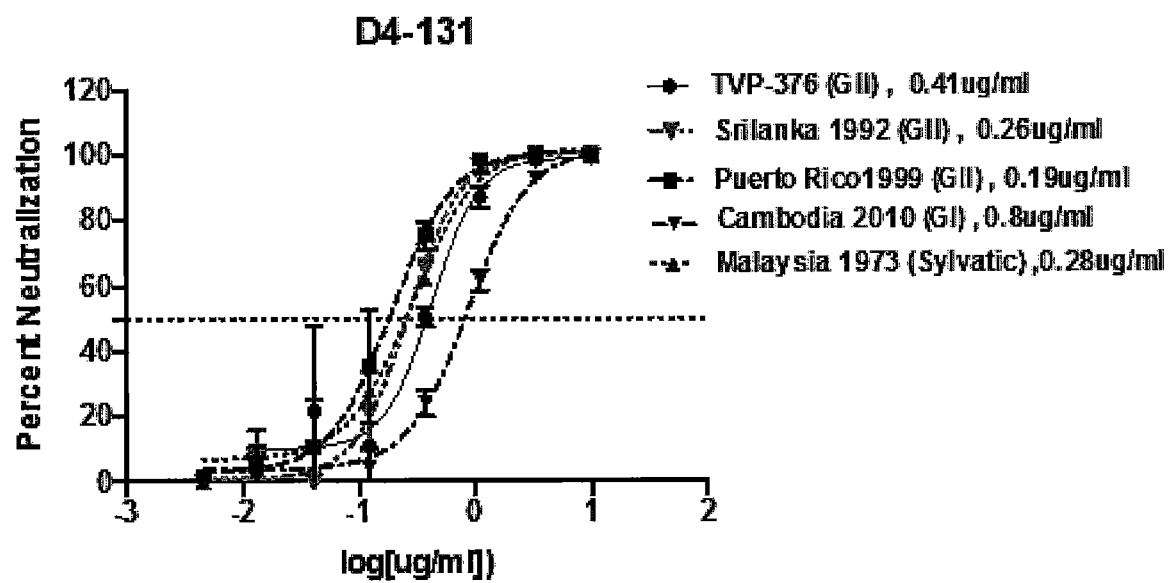

To determine if hMAbs D4-126 and D4-131 neutralized diverse strains of DENV4, we used a panel of recombinant isogenic DENV4 viruses expressing the E protein from different DENV4 genotypes and laboratory strains (Table 3). The hMAbs equally neutralized all variants tested except for a Cambodia 2010 genotype 1 (GI) strain, which was not neutralized by D4-126 and was neutralized weakly by D4-131 (FIG. 3A and FIG. 3B).

Mapping the Epitopes of DENV4 Neutralizing hMAbs

Figure 4A:
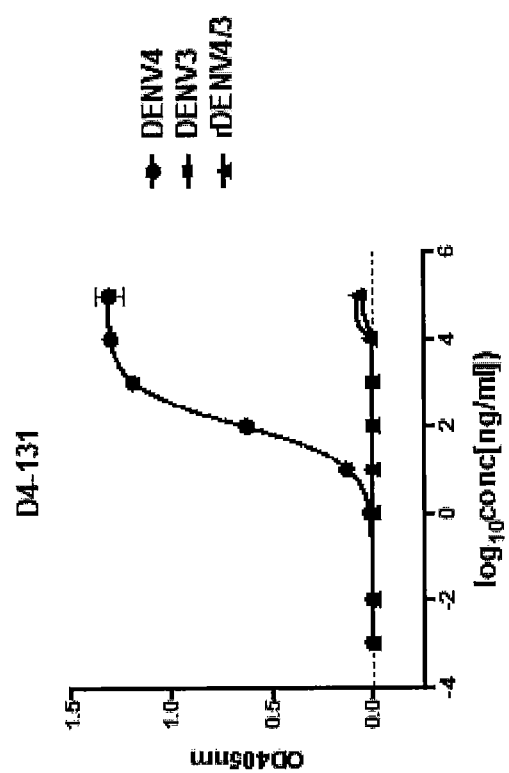
FIGS. 4A-4B. HMAbs D4-126 and D4-131 bind to epitopes near the hinge region between E protein domains I and II.
Figure 4A:
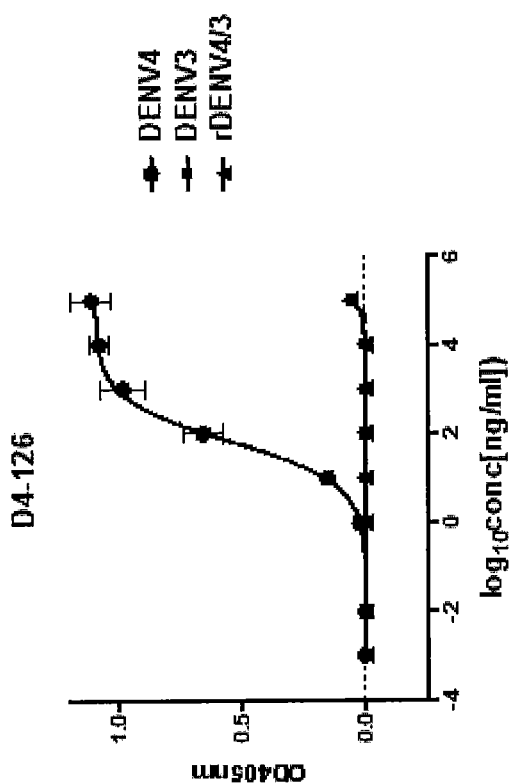
Figure 4B:
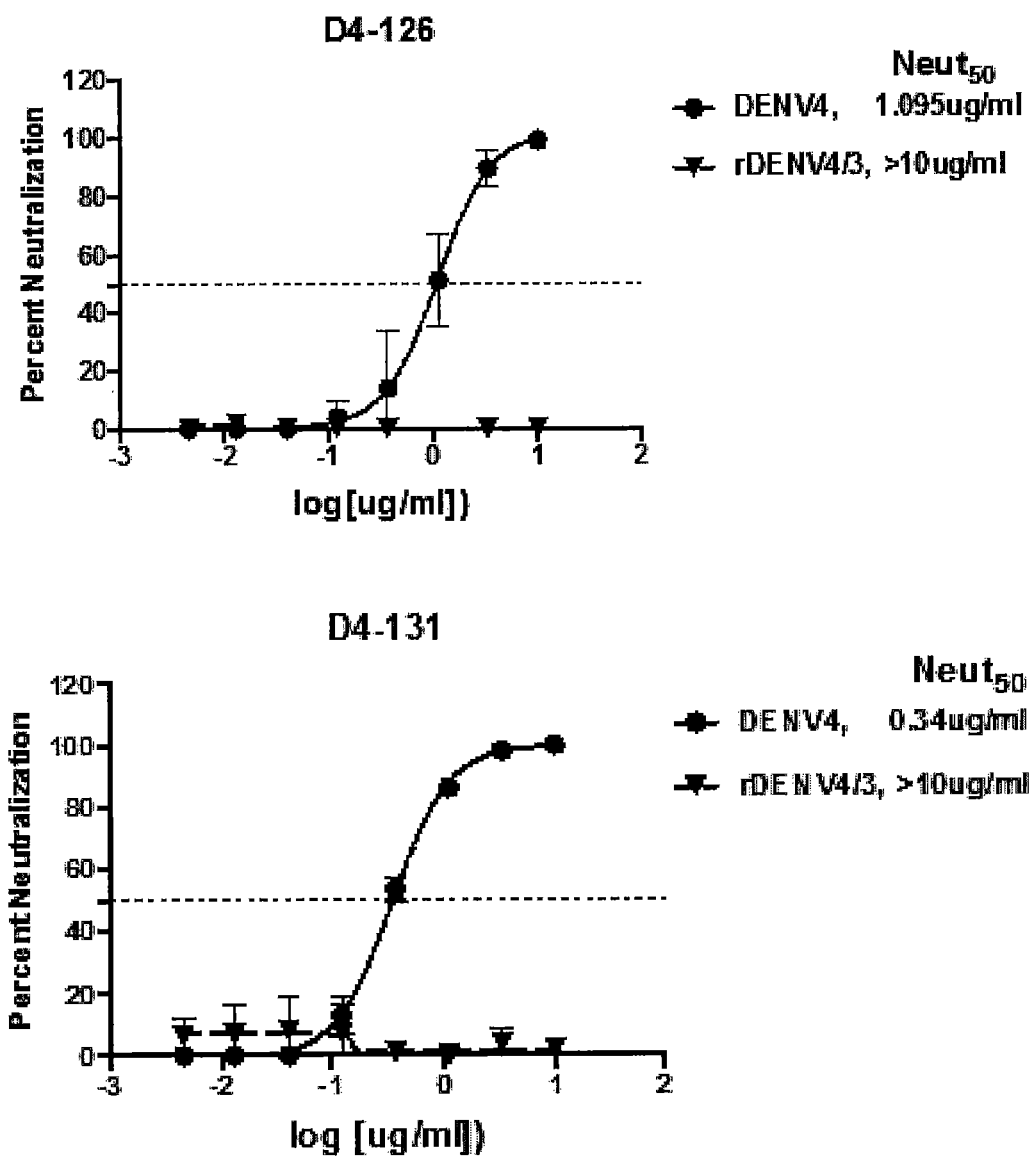

Human DENV1, 2 and 3 type-specific neutralizing antibodies often bind to quaternary structure epitopes centered on the EDI/II hinge and/or the EDIII region. Recently, we demonstrated that it is possible to recover recombinant chimeric DENVs displaying E protein domains or epitopes from viruses of two different serotypes. We used a recombinant DENV4 with a mutated EDI/II hinge region (rDENV4/3) to map the binding sites of hMAbs D4-126 and D4-131. We did not detect any binding or neutralizing activity for the hMAbs D4-126 or D4-131 with the rDENV4/3 virus, indicating that the DENV4 EDI/II hinge residues are part of the epitope recognized by these MAbs (FIG. 4A and FIG. 4B).

As an alternate approach to mapping the epitopes of D4-126 and D4-131, both hMAbs were screened by shotgun mutagenesis against a comprehensive mutation library in which nearly every residue within prM and E was individually mutated to alanine, as described previously. Residues were identified as critical to binding of the DENV4 hMAb if they were required for the binding of DENV4 MAb, but did not other conformation-dependent MAbs. Six amino acids (K51, V53, K124, L135, K200, K234) in the EDI/II hinge and EDII regions were critical for binding of D4-126. Four amino acids (K51, K124, K200, K202) within the EDI/II hinge and EDII region were critical for binding of D4-131. These data validated our observations that the EDI/II hinge region residues are critical for binding of D4-126 and D4-131, and also indicated that the epitopes differ slightly between the two hMAbs.

Figure 5A:
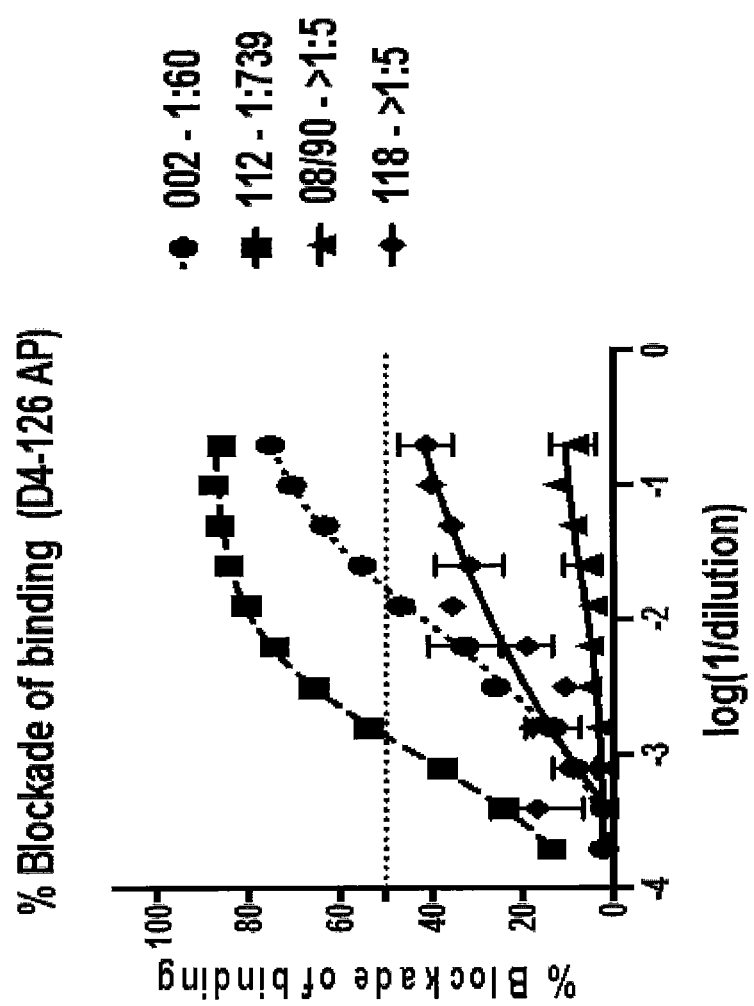
FIGS. 5A-5B. DENV4 immune sera block the binding of hMAbs D4-126 and D4-131 to DENV4. Blockade of binding assays were performed with DENV immune sera and MAbs D4-126 (FIG. 5A), D4-131 (FIG. 5B). Blockade assays were performed using 2 primary DENV4 immune sera (002 and 112), a primary DENV2 immune serum (08/90) and a primary DENV3 immune serum (118). The epitope specific response in the plasma was calculated by determining the titer of the plasma that leads to a 50% reduction in MAb binding to DENV4. The primary DENV4 immune sera efficiently blocked the binding of hMAbs D4-126 and D4-131 to DENV4. Primary DENV2 and DENV3 immune sera failed to block binding.
Figure 5B:
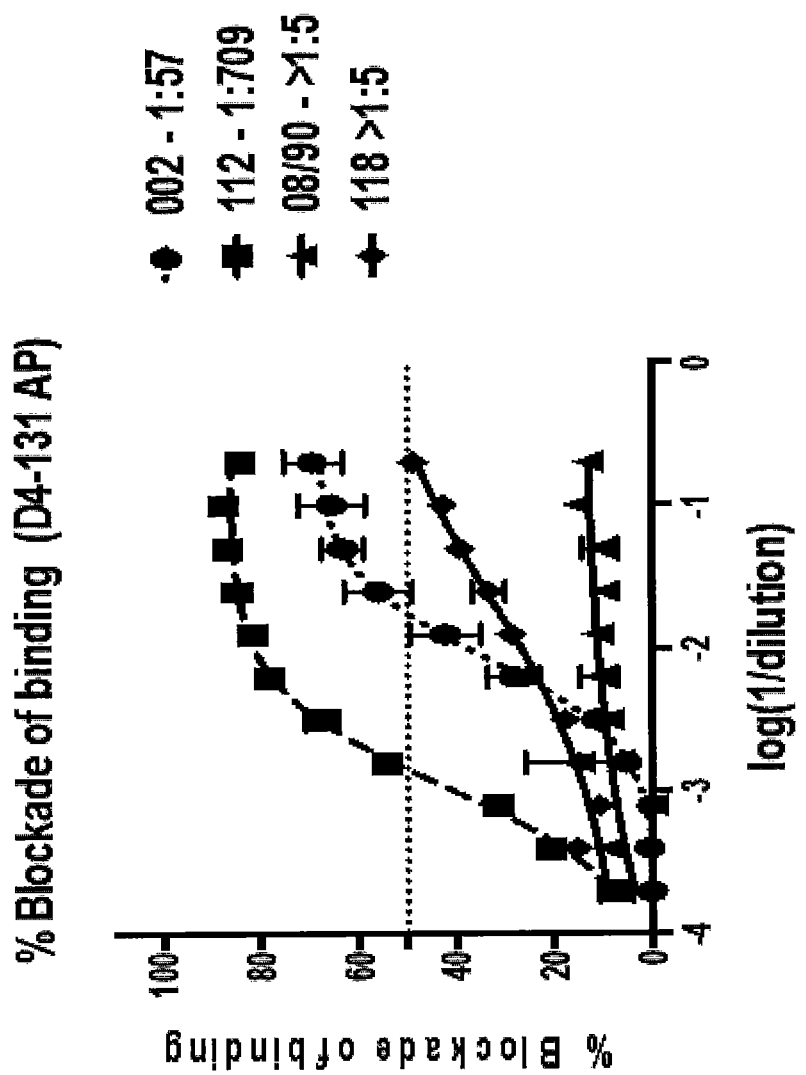

DENV4 Neutralizing hMAbs Define Epitopes Targeted by Serum Antibodies in DENV4 Immune Individuals HMAbs D4-126 and D4-131 were isolated from circulating memory B cells. Serum antibodies are thought generally to derive from secretion of long-lived plasma cells (LLPCs) residing in the bone marrow. To determine if DENV4 polyclonal serum neutralizing antibodies in immune sera secreted by LLPCs also targeted the D4-131 and D4-126 epitopes, we performed competition-binding assays with DENV4 immune serum samples and labeled DENV4-specific MAbs. As depicted in FIG. 5A and FIG. 5B, DENV4 immune sera effectively blocked the binding of each of the MAbs, whereas DENV2 or DENV3 immune sera had marginal effects on MAb binding. The magnitude of the DENV4 immune responses (based on their neutralization titers to DENV4) in serum samples correlated with the ability to block 50% of the binding of D4-126 or D4-131. These findings indicated that there are type-specific antibodies in DENV4 polyclonal antibodies in immune donor serum samples that bind to sites similar to the epitopes of hMAbs D4-126 and D4-131.

Figure 6A:
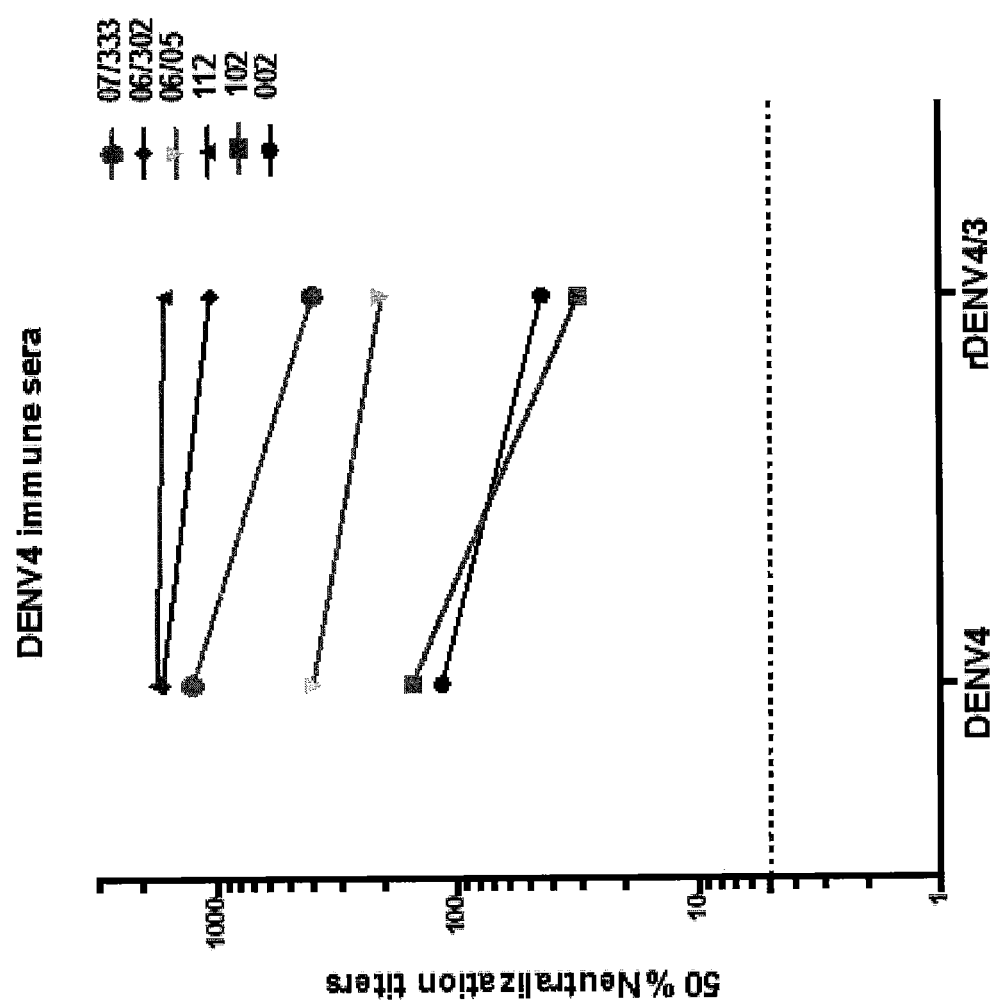
FIGS. 6A-B. The DENV4 E protein domain I/II hinge region is a target of long-lived plasma cell derived serum neutralizing antibodies in people exposed to DENV4 infections or a vaccine. A U937+DC-SIGN flow based neutralization assay was performed with primary DENV4 infection sera (FIG. 6A) or DENV4 monovalent vaccine sera (FIG. 6B) and WT DENV4 and rDENV4/3 viruses. Neut$_{50}$ titers$_{were}$ calculated and plotted. Samples that did not block 50% of infection at the highest concentration were assigned a value of 5.
Figure 6B:
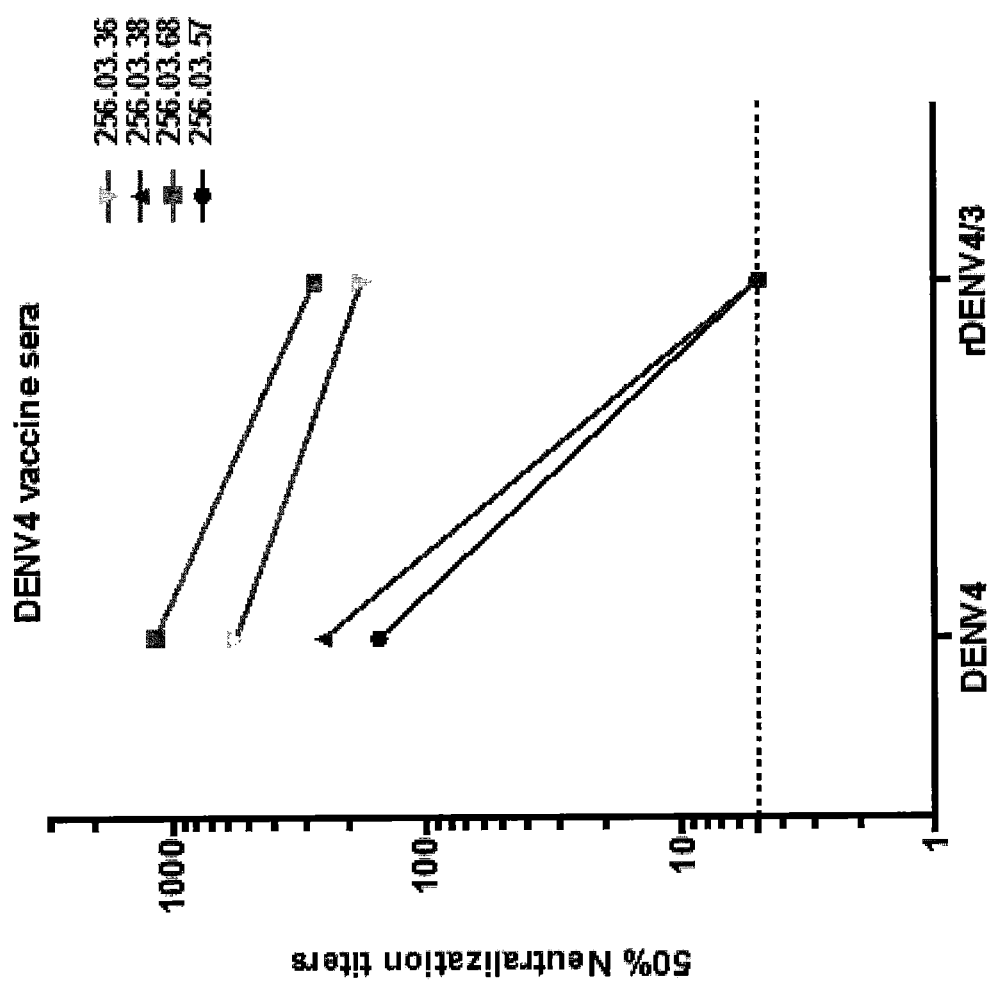

To further assess the epitope specificity of functionally neutralizing antibodies in DENV4 sera collected following infection or experimental vaccination, we performed neutralization assays with the rDENV4/3 virus, which had lost the epitopes recognized by hMAbs 126 and 131. Neutralization assays using the rDENV4/3 virus were performed with sera from six subjects with prior natural DENV4 infection and sera from 4 subjects previously immunized with a DENV4 live attenuated vaccine (FIG. 6A and FIG. 6B). Sera from both types of immune donors neutralized the rDENV4/3 strain poorly compared to WT DENV4 (FIG. 6B). The mean percent loss in neutralization with rDENV4/3 in both naturally infected immune and vaccine sera were significant (p=0.005 and p=0.002 respectively) as determined by one sample t-tests. Of the six DENV4 post-infection sera tested, three subjects (002, 102, 07/333) showed >60% loss in neutralization against rDENV4/3, while the remaining infection sera displayed a more modest to no reduction in neutralization (FIG. 6A). All of the vaccine sera tested neutralized the rDENV4/3 strain poorly compared to WT DENV4 (FIG. 6B). These results suggest that the EDI/II hinge region is a major target of type-specific DENV4 neutralizing antibodies.

Sustained humoral immunity depends on LLPCs to maintain protective levels of antibody and on memory B cells (MBCs), which comprise a subset of cells poised to expand and adapt in response to subsequent exposure to the infecting pathogen. In this study we characterized the properties of MBC- and LLPC-derived human antibodies that neutralize DENV4. Although people exposed to DENV4 infections developed serotype cross-reactive and type-specific antibodies, our results established that the type-specific antibodies were the principal determinants of neutralization of DENV4. Using MAbs isolated from the MBCs of people exposed to DENV4, we identified epitopes centered around the EDI/II hinge that were best displayed on intact virions as major targets of DENV4 neutralizing antibodies. In people exposed to DENV4 infections or a live attenuated vaccine candidate, both MBC- and LLPC-derived neutralizing antibodies recognized complex epitopes centered around the EDI/II hinge of DENV4.

Substantial progress has been made in understanding the epitopes targeted by human antibodies that neutralize DENV serotypes 1, 2, and 3, whereas serotype 4 is relatively understudied. The two DENV4 neutralizing MAbs reported in this study were sensitive to changes in or near the EDI/II hinge region. The hinge region plays a critical role in the conformational change that E protein undergoes at low pH to fuse to the endosomal membrane allowing viral uncoating and the release of viral RNA into the cellular cytoplasm. Because these epitopes are located in this region, we hypothesize that these DENV4 hMAbs act by preventing conformational changes in E protein required for fusion and a productive viral infection.

Some DENV4 epitopes targeted by neutralizing mouse MAbs vary between strains of DENV4. We evaluated if hMAb D4-126 and D4-131 effectively neutralized different strains of DENV4. All strains studied here were neutralized well, except for one GI strain (Cambodia 2010) that was resistant or partially resistant to hMAb D4-126 and D4-131 respectively. There are 16 amino acid differences between the E proteins of SL1992 (GII) neutralization sensitive and the Cambodian 2010 (GI) neutralization resistant strains. Three of the mutations in EDII (122 L->S; 203 T->K; 233 H->Y) overlapped with the region identified by shotgun mutagenesis as the binding sites of D4-126 and D4-131. We propose that natural variation between DENV4 strains leads to poor or altered binding of D4-126 and D4-131 and neutralization escape. Moreover, recent studies demonstrate that some DENV strains flex and "breathe" more than other strains, which can also lead to better exposure of partially hidden epitopes. Mutations outside the main footprints of D4-126 and D4-131 may also indirectly alter epitope exposure and contribute to strain specific differences in neutralization sensitivity.

The LLPC-derived polyclonal serum antibodies likely provide the first line of defense against re-infection in vivo. Our studies using blockade of antibody binding demonstrated that the DENV4 polyclonal immune sera contained antibodies that specifically blocked the binding of MAbs D4-126 and D4-131 to their epitopes. Additionally, a recombinant DENV4 strain missing the D4-126 and D4-131 epitopes was less sensitive to neutralization by DENV4 infection and vaccine sera compared to WT DENV4. These results establish that the region/epitopes defined using MAbs are important targets of the LLPC-derived polyclonal serum antibody response. In some individuals, a fraction or most of the serum DENV4 neutralizing antibody response was unaffected by EDI/II hinge mutations, indicating other regions and epitopes likely are involved in DENV4 neutralization. A chimpanzee DENV4 type-specific strongly neutralizing MAb 5H2 was directed to the EDI region. Cockburn et al. demonstrated that at least a portion of antibodies in DENV4 convalescent patient sera bound to epitopes on DI that overlapped with that of MAb 5H2.

In summary, we propose that the EDI/II hinge region is a target of DENV4 neutralizing human antibodies in both the MBC and LLPC compartments. The EDI/II hinge region is also a target of human type-specific antibodies that neutralize DENV1 and DENV3.

Cells.

*Aedes albopictus* C6/36 cells were maintained in MEM (Gibco) medium at 32° C. Vero cells (American Type Culture Collection; CCL-81) were maintained in Dulbecco's modified Eagle's (DMEM-F12) medium at 37° C. A human monocyte lymphoma cell line U937 ectopically expressing dendritic cell-specific intercellular adhesion molecule-3-grabbing non-integrin DC-SIGN (U937+DC-SIGN)(36, 37) was maintained in RPMI-1640 (Gibco) medium at 37° C. supplemented with 50 mM beta mercaptoethanol. All growth and maintenance media used were supplemented with 5% FBS, 100 U/mL penicillin, 100 mg/mL streptomycin, 0.1 mM non-essential amino acids (Gibco) and 2 mM glutamine. All cells were incubated in the presence of 5% $CO_2$. The 5% FBS was reduced to 2% to make infection medium for each cell line.

Viruses, rE and rEDIII.

The DENV1 (American genotype; strain West Pac74), DENV2 (Asian genotype; strain S-16803), DENV3 (Asian genotype; strain CH-53489), DENV4 (American genotype; strain TVP-376) viruses (provided by Robert Putnak, Walter Reed Army Institute of Research, Silver Spring, Md.) were used for both binding enzyme-linked immunosorbent assays (ELISAs) and neutralization assays. All viruses used in the neutralization assays were grown in C6/36 *Aedes albopictus* mosquito cells at 32° C., as previously described (38). DENV4 virus was purified as previously described. DENV2 (New Guinea C) purified live virus was purchased from Microbix Biosystems, Inc. (Mississauga, Ontario, Canada). Recombinant envelope (rE) proteins (80% of E protein) from each of the four serotypes were produced within our laboratory or purchased from Hawaii Biotech, Inc. Recombinant EDIII proteins were obtained as described previously.

DENV4 Immune Sera.

Convalescent DENV4 immune serum samples were obtained from ongoing studies in dengue endemic countries or from travelers visiting dengue endemic countries. DENV4 immune sera were also obtained from people who received a live attenuated monovalent DENV4 vaccine under development by the US National Institutes of Health. The protocol for obtaining dengue immune blood samples was approved by the Institutional Review Board of the University of North Carolina at Chapel Hill (protocol 08-0895).

Depletion of DENV4-Specific Antibodies from Human Immune Sera Collected from Subjects with Prior DENV4 Infection or Vaccination.

Purified DENV was absorbed onto 4.5-μm Polybead polystyrene microspheres (Polysciences, Inc.) at a bead (μL) to ligand (μg) ratio of 5:2. Polystyrene beads were washed three times with 0.1 M borate buffer (pH 8.5) and incubated with the relevant purified DENV (DENV4 for homotypic depletions and DENV2 for heterotypic depletions) overnight at room temperature (RT). Control beads were incubated overnight with an equivalent amount of bovine serum albumin (BSA). The control and virus-adsorbed beads were blocked with BSA (10 mg/mL) in borate buffer for 30 min at RT three times and washed four times with PBS. DENV4 immune sera from naturally infected individuals or NIH vaccine candidate recipients were depleted of virus-specific antibodies by incubating the samples with virus-adsorbed beads for 1 h at 37° C. with end-over-end mixing. Samples were subjected to at least three sequential rounds of depletions before confirming successful removal of the respective antibodies by ELISA. The ability of the depleted samples to neutralize viruses of all of the four serotypes then was tested after the confirmation ELISA.

Generation of DENV4-Specific MAbs.

Previously cryopreserved peripheral blood mononuclear cells (PBMCs) were thawed rapidly in a 37° C. water bath and washed prior to transformation with Epstein-Barr virus (EBV) and incubated with CpG and additional supplements, as described previously. Cultures were incubated at 37° C. with 5% $CO_2$ for 10 days prior to screening for DENV4-reactive cell lines with ELISA. The minimal frequency of DENV4-reactive B cells was estimated on the basis of the number of wells with DENV4-reactive supernatants as compared to the total number of lymphoblastoid cell line colonies in the transformation plates, as follows: [number of wells with DENV4-reactive supernatants]/[number of LCL colonies in the plate]. Cells from wells with supernatants reacting in the DENV4 capture ELISA were subjected to cytofusion with HMMA2.5 non-secreting myeloma cells, as previously described. Following cytofusion, hybridomas were selected for growth in HAT medium containing ouabin. Wells containing hybridomas producing DENV4-reactive antibodies were cloned biologically by 3 rounds of limiting dilution plating. Once clonal, the cell lines were used to produce MAb immunoglobulin G (IgG) in cell supernatants, using serum-free medium, followed by protein G column purification.

Virus, rE and rEDIII ELISA.

Equivalent quantities of DENV (as previously titrated by ELISA) virus was captured by anti-E mouse mAb 4G2, or rE proteins were directly coated (rE—100 ng/well; rEDIII—200 ng/well) on ELISA plates overnight at 4° C. Plates were blocked with 3% (vol/vol) normal goat serum (Gibco—Thermo Fisher, USA), in Tris-buffered saline (TBS) containing 0.05% (vol/vol) Tween 20 (blocking buffer). Primary antibodies were diluted serially to generate a range of concentrations. Alkaline-phosphotase conjugated secondary antibodies were used to detect binding of primary antibodies with p-nitrophenyl phosphate substrate, and reaction color changes were quantified by spectrophotometry.

Blockade of Binding Assays.

Blockade of binding assays were performed as described previously. Briefly, DENV4 was captured using mouse anti-E MAb 4G2, and blocked as described above. Serial dilutions of DENV serum were added to the DENV4-coated plates and incubated at 37° C. for 1 h. The plates were washed and alkaline-phosphatase conjugated DENV4 hMAbs were added and incubated at 37° C. for 1 h. P-nitrophenyl phosphate substrate was added and reaction color changes were quantified by spectrophotometry. Percentage of blockade of binding was calculated as follows: (100-[OD of sample/OD of negative control]*100).

Flow-Based U937+DC-SIGN Neutralization Assay.

Neutralization potential of the DENV4 immune sera and hMAbs were measured using a flow cytometry-based neutralization assay with U937+DC-SIGN cells as previously described. Briefly, virus and antibody mixtures or serum were incubated for 1 h at 37° C., prior to the addition of U937+DC-SIGN cells. After 2 h of incubation, cells were washed twice with infection media. Cells were then fixed and permeabilized 24 h after infection, probed with 2H2 (anti-prM MAb) conjugated to Alexa-Fluor 488 and infected cells quantified using a Guava flow cytometer (EMD Millipore). Stained cells were analyzed to calculate 50% neutralization titers.

Construction of the rDENV Viruses.

rDENV4/3 viruses were generated as described previously. Briefly, the DENV4 genome was split into 4 separate plasmids (A, B, C, D), allowing production of genomic cDNA. Plasmids were digested, and genome fragments were ligated together into a full-length-cDNA genome from which RNA transcripts were derived. These transcripts were electroporated into cells, and cell culture supernatant containing viable virus was harvested. Virus was passaged two times on C6/36 cell monolayer cultures and stored at −80° C. To generate rDENVs, the nucleotide sequence of the envelope glycoprotein was changed to alter the amino acid residues. rDENV4/3 contains EDI/II hinge residues (25 amino acids) from DENV3.

Generation of DENV4 Strains Displaying Diverse E Glycoproteins.

In order to examine genetic diversity within a serotype, a panel of near-isogenic rDENV4 viruses was generated by replacing the E gene of WT genotype II infectious clone virus (Sri Lanka 1992; Accession: KJ160504.1) with that of E glycoprotein genes representing diverse strains within DENV4. Subgenomic A plasmids were synthesized encoding E protein genes only (all others proteins remained Sri Lanka 1992) representing genotype I (GI; Cambodia 2010; Accession: KF543272.1), genotype II (GII; Puerto Rico 1999; Accession: FJ882599.1), or a sylvatic E sequence (Malaysia 1973; Accession: JF262780). Recombinant subgenomic A plasmids were synthesized, and viral assembly and rescue were performed as described above for generation of rDENV4 viruses.

Shotgun Mutagenesis Epitope Mapping.

Shotgun mutagenesis epitope mapping was performed as described previously. Briefly, a DENV4 prM-E protein expression construct was subjected to high-throughput alanine-scanning mutagenesis to generate a comprehensive mutation library (each residue mutated to alanine, and alanine residues mutated to serine). Mutant proteins (97% coverage) were generated and arrayed into 384-well plates. Mutants were transfected into HEK-293T cells and allowed to express for 22 h. Cells were fixed in 4% (vol/vol) paraformaldehyde (Electron Microscopy Sciences) and permeabilized with 0.1% (wt/vol) saponin (Sigma) in PBS containing calcium and magnesium. Cells were stained with purified anti-DENV4 hMAbs (D4-126, D4-131) diluted in 10% normal goat serum (NGS; Sigma) and 0.1% saponin, pH 9.0. Antibody binding was detected using Alexa Fluor 488-conjugated secondary antibody (Jackson ImmunoResearch Laboratories) in 10% NGS (Sigma) and 0.1% saponin. Cells were washed three times with PBS supplemented with 0.1% saponin, 1 mM $MgCl_2$, and $CaCl_2$ followed by two washes in PBS. The mean cellular fluorescence was detected using a high-throughput flow cytometer (HTFC; Intellicyt). Mutations were identified as critical to the hMAb epitope if they did not bind the test hMAb but did bind other conformation-dependent MAbs. This counter screen strategy facilitated the exclusion of E mutants that were locally misfolded or had expression defects.

The foregoing is illustrative of the present invention, and is not to be construed as limiting thereof. The invention is defined by the following claims, with equivalents of the claims to be included therein.

All publications, patent applications, patents, nucleotide sequences, amino acid sequences, GenBank accession numbers and other references cited herein are incorporated by reference in their entireties for the teachings relevant to the sentence and/or paragraph in which the reference is presented.

```
SEQUENCES
DENV 1 backbone sequence AAs 281-674 of GenBank
Accession No. AAB70694 (DENV 1 E glycoprotein
also in GenBank Accession No. U88535.1)
                                       (SEQ ID NO: 16)
MRCVGIGNRD FVEGLSGATW VDVVLEHGSC VTTMAKDKPT

LDIELLKTEV TNPAVLRKLC IEAKISNTTT DSRCPTQGEA

TLVEEQDTNF VCRRTFVDRG WGNGCGLFGK GSLITCAKFK

CVTKLEGKIV QYENLKYSVI VTVHTGDQHQ VGNETTEHGT

TATITPQAPT SEIQLTDYGA LTLDCSPRTG LDFNEMVLLT

MEKKSWLVHK QWFLDLPLPW TSGASTSQET WNRQDLLVTF

KTAHAKKQEV VVLGSQEGAM HTALTGATEI QTSGTTTIFA

GHLKCRLKMD KLTLKGMSYV MCTGSFKLEK EVAETQHGTV

LVQVKYEGTD APCKIPFSSQ DEKGVTQNGR LITANPIVTD

KEKPVNIEAE PPFGESYIVV GAGEKALKLS WFKK

DENV2 backbone sequence AAs 281-674 of GenBank
Accession No. ADA00411 (DENV 2 E glycoprotein
also in GenBank Accession No. GU289914.1)
                                       (SEQ ID NO: 17)
MRCIGISNRD FVEGVSGGSW VDIVLEHGSC VTTMAKNKPT

LDFELIKTEA KQPATLRKYC IEAKLTNTTT ESRCPTQGEP

SLNEEQDKRF VCKHSMVDRG WGNGCGLFGK GGIVTCAMFT

CKKNMEGKVV QPENLEYTIV VTPHSGEEHA VGNDTGKHGK

EIKVTPQSSI TEAELTGYGT VTMECSPRTG LDFNEMVLLQ

MENKAWLVHR QWFLDLPLPW LPGADTQGSN WIQKETLVTF

KNPHAKKQDV VVLGSQEGAM HTALTGATEI QMSSGNLLFT

GHLKCRLRMD KLQLKGMSYS MCTGKFKVVK EIAETQHGTI

VIRVQYEGDG SPCKIPFEIM DLEKRHVLGR LITVNPIVTE

KDSPVNIEAE PPFGDSYIII GVDPGQLKLN WFKK

DENV3 backbone sequence AAs 281-672 of GenBank
Accession No. AF155000 (DENV 3 E glycoprotein
also in GenBank Accession No. JQ411814.1)
                                       (SEQ ID NO: 18)
MRCVGIGNRD FVEGLSGATW VDVVLEHGGC VTTMAKNKPT

LDIELQKTEA TQLATLRKLC IEGKITNITT DSRCPTQGEA

VLPEEQDQNY VCKHTYVDRG WGNGCGLFGK GSLVTCAKFQ

CLEPIEGKVV QYENLKYTVI ITVHTGDQHQ VGNETQGVTA

EITPQASTTE AILPEYGTLG LECSPRTGLD FNEMILLTMK

NKAWMVHRQW FFDLPLPWTS GATTETPTWN RKELLVTFKN

AHAKKQEVVV LGSQEGAMHT ALTGATEIQN SGGTSIFAGH

LKCRLKMDKL ELKGMSYAMC TNTFVLKKEV SETQHGTILI

KVEYKGEDAP CKIPFSTEDG QGKAHNGRLI TANPVVTKKE

EPVNIEAEPP FGESNTVIGI GDNALKINWY KK

DENV4 backbone sequence AAs 280-673 of GenBank
Accession No. AHN50410 (DENV 4 E glycoprotein
also in GenBank Accession No. KJ160504.1)
                                       (SEQ ID NO: 19)
MRCVGVGNRD FVEGVSGGAW VDLVLEHGGC VTTMAQGKPT

LDFELTKTTA KEVALLRTYC IEASISNITT ATRCPTQGEP

YLKEEQDQQY ICRRDVVDRG WGNGCGLFGK GGVVTCAKFS

CSGKITGNLV QIENLEYTVV VTVHNGDTHA VGNDTSNHGV

TATITPRSPS VEVKLPDYGE LTLDCEPRSG IDFNEMILMK

MKKKTWLVHK QWFLDLPLPW TAGADTSEVH WNYKERMVTF

KVPHAKRQDV TVLGSQEGAM HSALAGATEV DSGDGNHMFA

GHLKCKVRME KLRIKGMSYT MCSGKFSIDK EMAETQHGTT

VVKVKYEGAG APCKVPIEIR DVNKEKVVGR VISSTPLAEN

TNSVTNIELE PPFGDSYIVI GVGNSALTLH WFRK

DENV2/4 M-Complete Modified Swap
                                       (SEQ ID NO: 14)
MNNQRKKARNTPFNMLKRERNRVSTVQQLTKRFSLGMLQGRGPLKLFMAL

VAFLRFLTIPPTAGILKRWGTIKKSKAINVLRGFRKEIGRMLNILNRRRR

SAGMIIMLIPTVMAFHLTTRNGEPHMIVSRQEKGKSLLFKTEDGVNMCTL

MAMDLGELCEDTITYNCPLLRQNEPEDIDCWCNSTSTWVTYGTCTTTGEH
```

-continued

RREKRSVALVPHVGMGLETRTETWMSSEGAWKHAQRIETWILRHPGFTIM
AAILAYTIGTTHFQRALIFILLTAVAPSMTMRCIGISNRDFVEGVSGGSW
VDIVLEHGSCVTTMAKNKPTLDFELTKTTAKEVALLRTYCIEAKISNITT
ESRCPTQGEPYLKEEQDQQYICKHSMVDRGWGNGCGLFGKGGIVTCAKFS
CSGKITGNLVQPENLEYTIVVTPHSGEEHAVGNDTGKHGKEIKVTPQSSI
TEAELTGYGTVTMECSPRTGLDFNEMVLLKMKKKTWLVHKQWFLDLPLPW
TAGADTSEVHWNYKETLVTFKNPHAKKQDVTVLGSQEGAMHTALTGATEV
DSGDGNHMFAGHLKCRLRMDKLQLKGMSYSMCTGKFKVVKEIAETQHGTI

VIRVQYEGDGSPCKIPFEIMDLEKRHVLGRLITVNPIVTEKDSPVNIEAE

PPFGDSYHIGVDPGQLKLNWFKKGSSIGQMFETTMRGAKRMAILGDTAWD

FGSLGGVFTSIGKALHQVFGAIYGAAFSGVSWTMKILIGVIITWIGMNSR

STSLSVSLVLVGIVTLYLGVMVQADSGCVVSWKNKELKCGSGIFITDNVH

TWTEQYKFQPESPSKLASAIQKAQEEGICGIRSVTRLENLMWKQITPELN

HILAENEVKLTIMTGDIKGIMQAGKRSLRPQPTELKYSWKTWGKAKMLST

ESHNQTFLIDGPETAECPNTNRAWNSLEVEDYGFGVFTTNIWLKLKEKQD

AFCDSKLMSAAIKDNRAVHADMGYWIESALNDTWKIEKASFIEVKNCHWP

KSHTLWSNGVLESEMIIPKNLAGPVSQHNYRPGYHTQIAGPWHLGKLEMD

FDFCDGTTVVVTEDCGNRGPSLRTTTASGKLITEWCCRSCTLPPLRYRGE

DGCWYGMEIRPLKEKEENLVNSLVTAGHGQVDNFSLGVLGMALFLEEMLR

TRVGTKHAILLVAVSFVTLITGNMSFRDLGRVVVMVGATMTDDIGMGVTY

LALLAAFKVRPTFAAGLLLRKLTSKELMMTTIGIVLLSQSTIPETILELT

DALALGMMVLKMVRNMEKYQLAVTIMAILCVPNAVILQNAWKVSCTILAV

VSVSPLLLTSSQQKTDWIPLALTIKGLNPTAIFLTTLSRTSKKRSWPLNE

AIMAVGMVSILASSLLKNDIPMTGPLVAGGLLTVCYVLTGRSADLELERA

ADVKWEDQAEISGSSPILSITISEDGSMSIKNEEEEQTLTILIRTGLLVI

SGLFPVSIPITAAAWYLWEVKKQRAGVLWDVPSPPPMGKAELEDGAYRIK

QKGILGYSQIGAGVYKEGTFHTMWHVTRGAVLMHKGKRIEPSWADVKKDL

ISYGGGWKLEGEWKEGEEVQVLALEPGKNPRAVQTKPGLFRTNAGTIGAV

SLDFSPGTSGSPIIDKKGKVVGLYGNGVVTRSGAYVSAIAQTEKSIEDNP

EIEDDIFRKRRLTIMDLHPGAGKTKRYLPAIVREAIKRGLRTLILAPTRV

VAAEMEEALRGLPIRYQTPAIRAEHTGREIVDLMCHATFTMRLLSPVRVP

NYNLIIMDEAHFTDPASIAARGYISTRVEMGEAAGIFMTATPPGSRDPFP

QSNAPIIDEEREIPERSWNSGHEWVTDFKGKTVWFVPSIKAGNDIAACLR

KNGKKVIQLSRKTFDSEYVKTRTNDWDFVVTTDISEMGANFKAERVIDPR

RCMKPVILTDGEERVILAGPMPVTHSSAAQRRGRIGRNPKNENDQYIYMG

EPLENDEDCAHWKEAKMLLDNINTPEGIIPSMFEPEREKVDAIDGEYRLR

GEARKTFVDLMRRGDLPVWLAYKVAAEGINYADRRWCFDGIKNNQILEEN

VEVEIWTKEGERKKLKPRWLDARIYSDPLALKEFKEFAAGRKSLTLNLIT

EMGRLPTFMTQKARDALDNLAVLHTAEAGGRAYNHALSELPETLETLLLL

TLLATVTGGIFLFLMSGRGIGKMTLGMCCIITASILLWYAQIQPHWIAAS

-continued

IILEFFLIVLLIPEPEKQRTPQDNQLTYVVIAILTVVAATMANEMGFLEK

TKKDLGLGSIATQQPESNILDIDLRPASAWTLYAVATTFVTPMLRHSIEN

SSVNVSLTAIANQATVLMGLGKGWPLSKMDIGVPLLAIGCYSQVNPITLT

AALLLLVAHYAIIGPGLQAKATREAQKRAAAGIMKNPTVDGITVIDLDPI

PYDPKFEKQLGQVMLLVLCVTQVLMMRTTWALCEALTLATGPISTLWEGN

PGRFWNTTIAVSMANIFRGSYLAGAGLLFSIMKNTTNTRRGTGNIGETLG

EKWKSRLNALGKSEFQIYKKSGIQEVDRTLAKEGIKRGETDHHAVSRGSA

KLRWFVERNMVTPEGKVVDLGCGRGGWSYYCGGLKNVREVKGLTKGGPGH

EEPIPMSTYGWNLVRLQSGVDVFFIPPEKCDTLLCDIGESSPNPTVEAGR

TLRVLNLVENWLNNNTQFCIKVLNPYMPSVIEKMETLQRKYGGALVRNPL

SRNSTHEMYWVSNASGNIVSSVNMISRMLINRFTMRHKKATYEPDVDLGS

GTRNIGIESEIPNLDIIGKRIEKIKQEHETSWHYDQDHPYKTWAYHGSYE

TKQTGSASSMVNGVVRLLTKPWDVVPMVTQMAMTDTTPFGQQRVFICEKV

DTRTQEPKEGTKKLMKITAEWLWKELGKKKTPRMCTREEFTRKVRSNAAL

GAIFTDENKWKSAREAVEDSRFWELVDKERNLHLEGKCETCVYNMMGKRE

KKLGEFGKAKGSRAIWYMWLGARFLEFEALGFLNEDHWFSRENSLSGVEG

EGLHKLGYILRDVSKKEGGAMYADDTAGWDTRITLEDLKNEEMVTNHMEG

EHKKLAEAIFKLTYQNKVVRVQRPTPRGTVMDIISRRDQRGSGQVGTYGL

NTFTNMEAQLIRQMEGEGVFKNIQHLTVTEEIAVQNWLARVGRERLSRMA

ISGDDCVVKPLDDRFASALTALNDMGKIRKDIQQWEPSRGWNDWTQVPFC

SHHFHELIMKDGRVLVVPCRNQDELIGRARISQGAGWSLRETACLGKSYA

QMWSLMYFHRRDLRLAANAICSAVPSHWVPTSRTTWSIHAKHEWMTTEDM

LTVWNRVVVIQENPWMEDKTPVESWEEIPYLGKREDQWCGSLIGLTSRAT

WAKNIQAAINQVRSLIGNEEYTDYMPSMKRFRREEEEAGVLW

DENV2/4 EDII Swap (SEQ ID NO: 15)

MNNQRKKARNTPFNMLKRERNRVSTVQQLTKRFSLGMLQGRGPLKLFMAL

VAFLRFLTIPPTAGILKRWGTIKKSKAINVLRGFRKEIGRMLNILNRRRR

SAGMIIMLIPTVMAFHLTTRNGEPHMIVSRQEKGKSLLFKTEDGVNMCTL

MAMDLGELCEDTITYNCPLLRQNEPEDIDCWCNSTSTWVTYGTCTTTGEH

RREKRSVALVPHVGMGLETRTETWMSSEGAWKHAQRIETWILRHPGFTIM

AAILAYTIGTTHFQRALIFILLTAVAPSMTMRCIGISNRDFVEGVSGGSW

VDIVLEHGSCVTTMAKNKPTLDFELIKTEAKEVALLRTYCIEASISNITT

ATRCPTQGEPYLKEEQDQQYICRRDVVDRGWGNGCGLFGKGGVVTCAKFS

CSGKITGNLVQIENLEYTIVVTPHSGEEHAVGNDTGKHGKEIKVTPQSSI

TEAELTGYGTVTMECSPRTGLDFNEMILMKMKKKTWLVHKQWFLDLPLPW

TAGADTSEVHWNYKERMVTFKVPHAKRQDVTVLGSQEGAMHSALAGATEV

DSGDGNHMFTGHLKCRLRMDKLQLKGMSYSMCTGKFKVVKEIAETQHGTI

VIRVQYEGDGSPCKIPFEIMDLEKRHVLGRLITVNPIVTEKDSPVNIEAE

PPFGDSYIIIGVDPGQLKLNWFKKGSSIGQMFETTMRGAKRMAILGDTAW

DFGSLGGVFTSIGKALHQVFGAIYGAAFSGVSWTMKILIGVIITWIGMNS

RSTSLSVSLVLVGIVTLYLGVMVQADSGCVVSWKNKELKCGSGIFITDNV

HTWTEQYKFQPESPSKLASAIQKAQEEGICGIRSVTRLENLMWKQITPEL

NHILAENEVKLTIMTGDIKGIMQAGKRSLRPQPTELKYSWKTWGKAKMLS

TESHNQTFLIDGPETAECPNTNRAWNSLEVEDYGFGVFTTNIWLKLKEKQ

DAFCDSKLMSAAIKDNRAVHADMGYWIESALNDTWKIEKASFIEVKNCHW

PKSHTLWSNGVLESEMIIPKNLAGPVSQHNYRPGYHTQIAGPWHLGKLEM

DFDFCDGTTVVVTEDCGNRGPSLRTTTASGKLITEWCCRSCTLPPLRYRG

EDGCWYGMEIRPLKEKEENLVNSLVTAGHGQVDNFSLGVLGMALFLEEML

RTRVGTKHAILLVAVSFVTLITGNMSFRDLGRVVVMVGATMTDDIGMGVT

YLALLAAFKVRPTFAAGLLLRKLTSKELMMTTIGIVLLSQSTIPETILEL

TDALALGMMVLKMVRNMEKYQLAVTIMAILCVPNAVILQNAWKVSCTILA

VVSVSPLLLTSSQQKTDWIPLALTIKGLNPTAIFLTTLSRTSKKRSWPLN

EAIMAVGMVSILASSLLKNDIPMTGPLVAGGLLTVCYVLTGRSADLELER

AADVKWEDQAEISGSSPILSITISEDGSMSIKNEEEEQTLTILIRTGLLV

ISGLFPVSIPITAAAWYLWEVKKQRAGVLWDVPSPPPMGKAELEDGAYRI

KQKGILGYSQIGAGVYKEGTFHTMWHVTRGAVLMHKGKRIEPSWADVKKD

LISYGGGWKLEGEWKEGEEVQVLALEPGKNPRAVQTKPGLFRTNAGTIGA

VSLDFSPGTSGSPIIDKKGKVVGLYGNGVVTRSGAYVSAIAQTEKSIEDN

PEIEDDIFRKRRLTIMDLHPGAGKTKRYLPAIVREAIKRGLRTLILAPTR

VVAAEMEEALRGLPIRYQTPAIRAEHTGREIVDLMCHATFTMRLLSPVRV

PNYNLIIMDEAHFTDPASIAARGYISTRVEMGEAAGIFMTATPPGSRDPF

PQSNAPIIDEEREIPERSWNSGHEWVTDFKGKTVWFVPSIKAGNDIAACL

RKNGKKVIQLSRKTFDSEYVKTRTNDWDFVVTTDISEMGANFKAERVIDP

RRCMKPVILTDGEERVILAGPMPVTHSSAAQRRGRIGRNPKNENDQYIYM

GEPLENDEDCAHWKEAKMLLDNINTPEGIIPSMFEPEREKVDAIDGEYRL

RGEARKTFVDLMRRGDLPVWLAYKVAAEGINYADRRWCFDGIKNNQILEE

NVEVEIWTKEGERKKLKPRWLDARIYSDPLALKEFKEFAAGRKSLTLNLI

TEMGRLPTFMTQKARDALDNLAVLHTAEAGGRAYNHALSELPETLETLLL

LTLLATVTGGIFLFLMSGRGIGKMTLGMCCIITASILLWYAQIQPHWIAA

SIILEFFLIVLLIPEPEKQRTPQDNQLTYVVIAILTVVAATMANEMGFLE

KTKKDLGLGSIATQQPESNILDIDLRPASAWTLYAVATTFVTPMLRHSIE

NSSVNVSLTAIANQATVLMGLGKGWPLSKMDIGVPLLAIGCYSQVNPITL

TAALLLLVAHYAIIGPGLQAKATREAQKRAAAGIMKNPTVDGITVIDLDP

IPYDPKFEKQLGQVMLLVLCVTQVLMMRTTWALCEALTLATGPISTLWEG

NPGRFWNTTIAVSMANIFRGSYLAGAGLLFSIMKNTTNTRRGTGNIGETL

GEKWKSRLNALGKSEFQIYKKSGIQEVDRTLAKEGIKRGETDHHAVSRGS

AKLRWFVERNMVTPEGKVVDLGCGRGGWSYYCGGLKNVREVKGLTKGGPG

HEEPIPMSTYGWNLVRLQSGVDVFFIPPEKCDTLLCDIGESSPNPTVEAG

RTLRVLNLVENWLNNNTQFCIKVLNPYMPSVIEKMETLQRKYGGALVRNP

LSRNSTHEMYWVSNASGNIVSSVNMISRMLINRFTMRHKKATYEPDVDLG

SGTRNIGIESEIPNLDIIGKRIEKIKQEHETSWHYDQDHPYKTWAYHGSY

ETKQTGSASSMVNGVVRLLTKPWDVVPMVTQMAMTDTTPFGQQRVFKEKV

DTRTQEPKEGTKKLMKITAEWLWKELGKKKTPRMCTREEFTRKVRSNAAL

GAIFTDENKWKSAREAVEDSRFWELVDKERNLHLEGKCETCVYNMMGKRE

KKLGEFGKAKGSRAIWYMWLGARFLEFEALGFLNEDHWFSRENSLSGVEG

EGLHKLGYILRDVSKKEGGAMYADDTAGWDTRITLEDLKNEEMVTNHMEG

EHKKLAEAIFKLTYQNKVVRVQRPTPRGTVMDIISRRDQRGSGQVGTYGL

NTFTNMEAQLIRQMEGEGVFKNIQHLTVTEEIAVQNWLARVGRERLSRMA

ISGDDCVVKPLDDRFASALTALNDMGKIRKDIQQWEPSRGWNDWTQVPFC

SHHFHELIMKDGRVLVVPCRNQDELIGRARISQGAGWSLRETACLGKSYA

QMWSLMYFHRRDLRLAANAICSAVPSHWVPTSRTTWSIHAKHEWMTTEDM

LTVWNRVWIQENPWMEDKTPVESWEEIPYLGKREDQWCGSLIGLTSRATW

AKNIQAAINQVRSLIGNEEYTDYMPSMKRFRREEEEAGVLW

E protein for DENV2/4 M14+ hinge with tissue
culture adaption
                    (SEQ ID NO: 22)
MRCIGISNRDFVEGVSGGSWVDIVLEHGSCVTTMAKNKPTLDFELTKTTA

KEVALLRTYCIEAKLTNTTTESRCPTQGEPSLNEEQDKRFVCKHSMVDRG

WGNGCGLFGKGGIVTCAKFSCSGKITGNLVQIENLEYTIVVTPHSGEEHA

VGNDTGKHGKEIKVTPQSSITEAELTGYGTVTMECSPRSGIDFNEMVLLK

MKKKTWLVHKQWFLDLPLPWTAGADTSEVHWNDKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK prM protein for DENV2/4+ hinge with tissue
culture adaption
                    (SEQ ID NO: 23)
FHLTTRNGEPHMIVSRQEKGKSLLFKTEDGVNMCTLMAMDLGELCEDTIT

YNCPLLRQNEPEDIDCWCNSTSTWVTYGTCTTTGEHRREKRSVALVTHVG

MGLETRTETWMSSEGAWKHAQRIETWILRHPGFTIMAAILAYTIGTTHFQ

RALIFILLTAVAPSMT

DENV2/4-Complete Modified Swap E glycoprotein
                    (SEQ ID NO: 24)
MRCIGISNRDFVEGVSGGSWVDIVLEHGSCVTTMAKNKPTLDFELTKTTA

KEVALLRTYCIEAKISNITTESRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKKQDV

TVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK

-continued

DENV2/4 EDII Swap E glycoprotein
(SEQ ID NO: 25)
MRCIGISNRDFVEGVSGGSWVDIVLEHGSCVTTMAKNKPTLDFELIKTEA

KEVALLRTYCIEASISNITTATRCPTQGEPYLKEEQDQQYICRRDVVDRG

WGNGCGLFGKGGVVTCAKFSCSGKITGNLVQIENLEYTIVVTPHSGEEHA

VGNDTGKHGKEIKVTPQSSITEAELTGYGTVTMECSPRTGLDFNEMILMK

MKKKTWLVHKQWFLDLPLPWTAGADTSEVHWNYKERMVTFKVPHAKRQDV

TVLGSQEGAMHSALAGATEVDSGDGNHMFTGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK

TABLE 3

Characteristics of DENV4 strains used in the study

| Virus | Genotype | GenBank Accession No. |
|---|---|---|
| TVP-376 | II | KC963424 |
| Srilanka 1992 | II | KJ160504.1 |
| Puerto Rico 1999 | II | FJ882599.1 |
| Cambodia 2010 | I | KF543272.1 |
| Malaysia 1973 | Sylvatic | JF262780 |

TABLE 1

Panel of DENV immune and monovalent vaccine sera

| | Sera | Year of infection | Location of infection | Time since infection to blood draw | Reciprocal of $Neut_{50}$ titers against DENV1-4* | | | |
|---|---|---|---|---|---|---|---|---|
| | | | | | DENV1 | DENV2 | DENV3 | DENV4 |
| DENV4 immune sera | 002 | 1994 | Guatemala | 15 years | <20 | <20 | 29 | 77 |
| | 102 | 2007 | Honduras | 2 years | <20 | <20 | 41 | 159 |
| | 112 | 2001 | Nicaragua | 2 years | 128 | 346 | 175 | 1639 |
| | 07/333 | Unknown | Thailand | Unknown | <20 | 153 | 367 | >1280 |
| | 06/302 | Unknown | Thailand | Unknown | <20 | 32 | 60 | >1280 |
| | 06/105 | Unknown | Thailand | Unknown | <20 | 26 | 91 | 685 |
| DENV2 immune serum | 08/90 | Unknown | Thailand | Unknown | 20 | >1280 | 60 | 32 |
| DENV3 immune serum | 118 | 2009 | Nicaragua | 1 year | 60 | 32 | 980 | 76 |
| DENV4 vaccine sera | 256.03.36 | | | Vaccinated in 2009 | <20 | <20 | <20 | 142 |
| | 256.03.38 | | | Vaccinated in 2009 | <20 | <20 | <20 | 148 |
| | 256.03.57 | | | Vaccinated in 2009 | <20 | <20 | <20 | 144 |
| | 256.03.68 | | | Vaccinated in 2009 | <20 | <20 | <20 | 988 |

*The $Neut_{50}$ titer values in bold signify the highest $neut_{50}$ reciprocal titers for each sample.

TABLE 2

Neutralization of DENV4 by antibody depleted human DENV4 immune samples[a]

| | | Homotypic depletions | | | Heterotypic depletions | | |
|---|---|---|---|---|---|---|---|
| | Sample ID | Control Depleted $Neut_{50}$ | DENV4 depleted $Neut_{50}$ | % loss of Neutralization (mean ± SD) | Control Depleted $Neut_{50}$ | DENV2 depleted $Neut_{50}$ | % loss of Neutralization (mean ± SD) |
| DENV4 Immune sera | 002 | 58 | <20 | 100 | 82 | 84 | 0 |
| | 102 | 112 | 43 | 62 | 113 | 98 | 13 |
| | 112 | 1263 | <20 | 100 | 773 | 827 | 0 |
| Average | | | | 87 ± 18 | | | 4 ± 8 |
| DENV4 Vaccine sera | 256.03.36 | 175 | <20 | 100 | 175 | 142 | 19 |
| | 256.03.38 | 61 | <20 | 100 | 61 | 83 | 0 |
| | 256.03.57 | 53 | <20 | 100 | 98 | 75 | 23 |
| | 256.03.68 | 425 | 160 | 62 | 409 | 271 | 34 |
| Average | | | | 91 ± 19 | | | 19 ± 12 |

[a] A U937 + DC-SIGN flow based neutralization test was performed on human DENV4 immune sera depleted of DENV4 (homotypic) or DENV2 (heterotypic) binding antibodies and $Neut_{50}$ values (i.e., the dilution factor required to neutralize 50% of infection) were calculated. % loss of neutralization was calculated as follows: % loss of neutralization = 100 − [(DENV4/DENV2 depleted $Neut_{50}$/Control depleted $Neut_{50}$) × 100].

TABLE 4

1-4 Matrix

| | 6 | 15 | 18 | 19 | 23 | 29 | 36 | 37 | 43 | 46 | 49 | 50 | 51 | 52 | 53 | 55 | 58 | 59 |
|---|---|---|---|---|---|---|---|---|---|---|---|---|---|---|---|---|---|---|
| DENV1 | I | L | A | T | V | S | K | D | I | L | E | V | T | N | P | V | K | L |
| M12 | I | L | A | T | V | S | K | D | I | L | E | V | K | E | V | L | T | L |
| M14 | I | L | A | T | V | S | K | D | I | L | E | V | K | E | V | L | T | L |
| M-Comp. | I | L | A | T | V | S | K | D | I | T | T | V | K | E | V | L | T | L |
| DENV4 | V | V | G | A | L | G | Q | G | F | T | T | A | K | E | V | L | T | Y |

| | 125 | 126 | 128 | 129 | 132 | 136 | 138 | 140 | 145 | 148 | 150 | 154 | 156 | 157 | 160 | 167 | 168 | 170 |
|---|---|---|---|---|---|---|---|---|---|---|---|---|---|---|---|---|---|---|
| DENV1 | L | E | K | I | Y | K | S | I | T | Q | Q | E | T | E | T | Q | A | T |
| M12 | I | T | N | L | Y | K | S | I | T | Q | Q | E | T | E | T | Q | A | T |
| M14 | I | T | N | L | Y | K | S | I | T | Q | Q | E | T | E | T | Q | A | T |
| M-Comp. | I | T | N | L | Y | K | S | I | T | Q | Q | E | T | E | T | Q | A | T |
| DENV4 | I | T | N | L | I | E | T | V | N | T | A | D | S | N | V | R | S | S |

| | 234 | 235 | 236 | 237 | 242 | 243 | 247 | 249 | 251 | 262 | 265 | 270 | 271 | 272 | 273 | 274 | 275 | 276 |
|---|---|---|---|---|---|---|---|---|---|---|---|---|---|---|---|---|---|---|
| DENV1 | Q | D | L | L | T | A | K | E | V | T | T | I | Q | T | S | G | T | T |
| M12 | K | D | L | L | T | A | K | E | V | T | T | V | D | S | G | D | T | T |
| M14 | K | D | L | L | T | A | K | E | V | T | T | V | D | S | G | D | T | T |
| M-Comp. | K | D | L | L | T | A | R | E | T | T | T | V | D | S | G | D | T | T |
| DENV4 | K | E | R | M | V | P | R | D | T | S | A | V | D | S | G | D | G | N |

| | 330 | 335 | 337 | 338 | 339 | 340 | 342 | 343 | 344 | 345 | 346 | 347 | 348 | 351 | 353 | 354 | 355 | 357 |
|---|---|---|---|---|---|---|---|---|---|---|---|---|---|---|---|---|---|---|
| DENV1 | D | I | F | S | S | Q | E | K | G | V | T | Q | N | L | T | A | N | I |
| M12 | D | I | F | S | S | Q | E | K | G | V | T | Q | N | L | T | A | N | I |
| M14 | D | I | F | S | S | Q | E | K | G | V | T | Q | N | L | T | A | N | I |
| M-Comp. | D | I | F | S | S | Q | E | K | G | V | T | Q | N | L | T | A | N | I |
| DENV4 | G | V | I | E | I | R | V | N | K | E | K | V | V | V | S | S | T | L |

| | 64 | 68 | 71 | 72 | 80 | 81 | 83 | 88 | 89 | 90 | 91 | 95 | 96 | 112 | 113 | 114 | 120 | 122 | 123 |
|---|---|---|---|---|---|---|---|---|---|---|---|---|---|---|---|---|---|---|---|
| DENV1 | K | T | D | S | A | T | V | T | N | F | V | T | F | S | L | I | K | V | T |
| M12 | K | T | D | S | A | T | V | T | N | F | V | T | F | S | L | I | K | V | T |
| M14 | K | T | D | S | A | T | V | T | N | F | V | T | F | S | L | I | S | S | G |
| M-Comp. | S | I | A | S | A | Y | K | Q | Q | Y | I | T | F | S | L | I | S | S | G |
| DENV4 | S | I | A | T | P | Y | K | Q | Q | Y | I | D | V | G | V | V | S | S | G |

| | 171 | 173 | 174 | 176 | 180 | 186 | 189 | 191 | 197 | 199 | 200 | 202 | 205 | 222 | 225 | 228 | 229 | 230 | 233 |
|---|---|---|---|---|---|---|---|---|---|---|---|---|---|---|---|---|---|---|---|
| DENV1 | S | I | Q | T | A | S | T | L | V | L | T | E | S | S | S | Q | E | T | R |
| M12 | S | I | Q | T | A | S | T | L | V | L | K | K | T | A | S | Q | E | T | R |
| M14 | S | I | Q | T | A | S | T | L | V | L | K | K | T | A | S | E | V | H | Y |
| M-Comp. | S | I | Q | T | A | S | T | L | V | L | K | K | T | A | S | E | V | H | Y |
| DENV4 | V | V | K | P | E | E | S | I | I | M | K | K | T | A | D | E | V | H | Y |

| | 277 | 278 | 286 | 287 | 288 | 290 | 293 | 294 | 300 | 303 | 305 | 307 | 308 | 309 | 312 | 320 | 321 | 323 | 329 |
|---|---|---|---|---|---|---|---|---|---|---|---|---|---|---|---|---|---|---|---|
| DENV1 | T | I | R | L | K | D | T | L | V | T | S | K | L | E | V | V | L | Q | T |
| M12 | H | M | R | L | K | D | T | L | V | T | S | K | L | E | V | V | L | Q | T |
| M14 | H | M | R | L | K | D | T | L | V | T | S | K | L | E | V | V | L | Q | T |
| M-Comp. | H | M | R | L | K | D | T | L | V | T | S | K | L | E | V | V | L | Q | T |
| DENV4 | H | M | K | V | R | E | R | I | T | S | K | S | I | D | M | T | V | K | A |

| | 358 | 359 | 360 | 361 | 362 | 363 | 364 | 365 | 369 | 375 | 380 | 382 | 384 | 385 | 388 | 390 | 393 |
|---|---|---|---|---|---|---|---|---|---|---|---|---|---|---|---|---|---|
| DENV1 | V | T | D | K | E | K | P | V | A | E | V | A | E | K | K | S | K |
| M12 | V | T | D | K | E | K | P | V | A | E | V | A | E | K | K | S | K |
| M14 | V | T | D | K | E | K | P | V | A | E | V | A | E | K | K | S | K |
| M-Comp. | V | T | D | K | E | K | P | V | A | E | V | A | E | K | K | S | K |
| DENV4 | A | E | N | T | N | S | V | T | L | D | I | V | N | S | T | H | R |

TABLE 5

2-4 Matrix

|        | 4   | 6   | 7   | 19  | 23  | 36  | 37  | 46  | 49  | 52  | 53  | 55  | 58  | 64  | 65  | 66  | 68  | 71  |
|--------|-----|-----|-----|-----|-----|-----|-----|-----|-----|-----|-----|-----|-----|-----|-----|-----|-----|-----|
| DENV2  | I   | I   | S   | S   | I   | K   | N   | I   | E   | Q   | P   | T   | K   | K   | L   | T   | T   | E   |
| M12    | I   | I   | S   | S   | I   | K   | N   | I   | E   | E   | V   | L   | T   | K   | L   | T   | T   | E   |
| M14    | I   | I   | S   | S   | I   | K   | N   | I   | E   | E   | V   | L   | T   | K   | L   | T   | T   | E   |
| M-Comp.| I   | I   | S   | S   | I   | K   | N   | T   | T   | E   | V   | L   | T   | S   | I   | S   | I   | A   |
| DENV4  | V   | V   | G   | A   | L   | Q   | G   | T   | T   | E   | V   | L   | T   | S   | I   | S   | I   | A   |

|        | 124 | 125 | 126 | 128 | 129 | 132 | 139 | 143 | 145 | 147 | 148 | 156 | 157 | 160 | 161 | 162 | 163 | 164 |
|--------|-----|-----|-----|-----|-----|-----|-----|-----|-----|-----|-----|-----|-----|-----|-----|-----|-----|-----|
| DENV2  | N   | M   | E   | K   | V   | P   | I   | P   | S   | E   | E   | G   | K   | K   | E   | I   | K   | V   |
| M12    | K   | I   | T   | N   | L   | P   | I   | P   | S   | E   | E   | G   | K   | K   | E   | I   | K   | V   |
| M14    | K   | I   | T   | N   | L   | P   | I   | P   | S   | E   | E   | G   | K   | K   | E   | I   | K   | V   |
| M-Comp.| K   | I   | T   | N   | L   | P   | I   | P   | S   | E   | E   | G   | K   | K   | E   | I   | K   | V   |
| DENV4  | K   | I   | T   | N   | L   | I   | V   | V   | N   | D   | T   | S   | N   | V   | T   | A   | T   | I   |

|        | 199 | 200 | 203 | 205 | 210 | 221 | 222 | 227 | 228 | 229 | 230 | 232 | 233 | 236 | 237 | 242 | 247 | 251 |
|--------|-----|-----|-----|-----|-----|-----|-----|-----|-----|-----|-----|-----|-----|-----|-----|-----|-----|-----|
| DENV2  | L   | Q   | N   | A   | R   | L   | P   | Q   | G   | S   | N   | I   | Q   | T   | L   | N   | K   | V   |
| M12    | L   | K   | K   | T   | K   | T   | A   | Q   | G   | S   | N   | I   | Q   | T   | L   | N   | K   | V   |
| M14    | L   | K   | K   | T   | K   | T   | A   | S   | E   | V   | H   | N   | Y   | T   | L   | N   | K   | V   |
| M-Comp.| L   | K   | K   | T   | K   | T   | A   | S   | E   | V   | H   | N   | Y   | T   | L   | N   | R   | T   |
| DENV4  | M   | K   | K   | T   | K   | T   | A   | S   | E   | V   | H   | N   | Y   | R   | M   | V   | R   | T   |

|        | 303 | 307 | 308 | 309 | 312 | 320 | 322 | 323 | 325 | 329 | 331 | 335 | 337 | 340 | 342 | 343 | 345 | 346 |
|--------|-----|-----|-----|-----|-----|-----|-----|-----|-----|-----|-----|-----|-----|-----|-----|-----|-----|-----|
| DENV2  | T   | K   | V   | V   | I   | I   | I   | R   | Q   | D   | S   | I   | F   | M   | L   | E   | R   | H   |
| M12    | T   | K   | V   | V   | I   | I   | I   | R   | Q   | D   | S   | I   | F   | M   | L   | E   | R   | H   |
| M14    | T   | K   | V   | V   | I   | I   | I   | R   | Q   | D   | S   | I   | F   | M   | L   | E   | R   | H   |
| M-Comp.| T   | K   | V   | V   | I   | I   | I   | R   | Q   | D   | S   | I   | F   | M   | L   | E   | R   | H   |
| DENV4  | S   | S   | I   | D   | M   | T   | V   | K   | K   | A   | A   | V   | I   | R   | V   | N   | E   | K   |

|        | 384 | 385 | 386 | 388 | 390 | 393 |
|--------|-----|-----|-----|-----|-----|-----|
| DENV2  | P   | G   | Q   | K   | N   | K   |
| M12    | P   | G   | Q   | K   | N   | K   |
| M14    | P   | G   | Q   | K   | N   | K   |
| M-Comp.| P   | G   | Q   | K   | N   | K   |
| DENV4  | N   | S   | A   | T   | H   | R   |

|        | 72  | 81  | 83  | 88  | 89  | 90  | 91  | 93  | 94  | 95  | 96  | 113 | 118 | 120 | 122 | 123 |
|--------|-----|-----|-----|-----|-----|-----|-----|-----|-----|-----|-----|-----|-----|-----|-----|-----|
| DENV2  | S   | S   | N   | K   | R   | F   | V   | K   | H   | S   | M   | I   | M   | T   | K   | K   |
| M12    | S   | S   | N   | K   | R   | F   | V   | K   | H   | S   | M   | I   | M   | T   | K   | K   |
| M14    | S   | S   | N   | K   | R   | F   | V   | K   | H   | S   | M   | I   | K   | S   | S   | G   |
| M-Comp.| S   | Y   | K   | Q   | Q   | Y   | I   | K   | H   | S   | M   | I   | K   | S   | S   | G   |
| DENV4  | T   | Y   | K   | Q   | Q   | Y   | I   | R   | R   | D   | V   | V   | K   | S   | S   | G   |

|        | 167 | 169 | 170 | 171 | 173 | 174 | 176 | 177 | 180 | 181 | 183 | 184 | 186 | 189 | 191 | 197 |
|--------|-----|-----|-----|-----|-----|-----|-----|-----|-----|-----|-----|-----|-----|-----|-----|-----|
| DENV2  | Q   | S   | I   | T   | A   | E   | T   | G   | T   | V   | M   | E   | S   | T   | L   | V   |
| M12    | Q   | S   | I   | T   | A   | E   | T   | G   | T   | V   | M   | E   | S   | T   | L   | V   |
| M14    | Q   | S   | I   | T   | A   | E   | T   | G   | T   | V   | M   | E   | S   | T   | L   | V   |
| M-Comp.| Q   | S   | I   | T   | A   | E   | T   | G   | T   | V   | M   | E   | S   | T   | L   | V   |
| DENV4  | R   | P   | S   | V   | V   | K   | P   | D   | E   | L   | L   | D   | E   | S   | I   | I   |

|        | 262 | 265 | 270 | 271 | 272 | 273 | 274 | 277 | 278 | 280 | 286 | 287 | 290 | 293 | 294 | 300 |
|--------|-----|-----|-----|-----|-----|-----|-----|-----|-----|-----|-----|-----|-----|-----|-----|-----|
| DENV2  | T   | T   | I   | Q   | M   | S   | S   | L   | L   | T   | R   | L   | D   | Q   | L   | S   |
| M12    | T   | T   | V   | D   | S   | G   | D   | H   | M   | A   | R   | L   | D   | Q   | L   | S   |
| M14    | T   | T   | V   | D   | S   | G   | D   | H   | M   | A   | R   | L   | D   | Q   | L   | S   |
| M-Comp.| T   | T   | V   | D   | S   | G   | D   | H   | M   | A   | R   | L   | D   | Q   | L   | S   |
| DENV4  | S   | A   | V   | D   | S   | G   | D   | H   | M   | A   | K   | V   | E   | R   | I   | T   |

|        | 348 | 351 | 353 | 354 | 355 | 357 | 358 | 359 | 360 | 361 | 362 | 364 | 365 | 369 | 379 | 383 |
|--------|-----|-----|-----|-----|-----|-----|-----|-----|-----|-----|-----|-----|-----|-----|-----|-----|
| DENV2  | L   | L   | T   | V   | N   | I   | V   | T   | E   | K   | D   | P   | V   | A   | I   | D   |
| M12    | L   | L   | T   | V   | N   | I   | V   | T   | E   | K   | D   | P   | V   | A   | I   | D   |
| M14    | L   | L   | T   | V   | N   | I   | V   | T   | E   | K   | D   | P   | V   | A   | I   | D   |
| M-Comp.| L   | L   | T   | V   | N   | I   | V   | T   | E   | K   | D   | P   | V   | A   | I   | D   |
| DENV4  | V   | V   | S   | S   | T   | L   | A   | E   | N   | T   | N   | V   | T   | L   | V   | G   |

TABLE 6

3-4 Matrix.

|  | 6 | 15 | 18 | 19 | 23 | 36 | 37 | 43 | 46 | 49 | 51 | 52 | 53 | 55 | 58 | 59 | 63 |
|---|---|---|---|---|---|---|---|---|---|---|---|---|---|---|---|---|---|
| DENV3 | I | L | A | T | V | K | N | I | Q | E | T | Q | L | T | K | L | G |
| M12 | I | L | A | T | V | K | N | I | Q | E | K | E | V | L | T | L | G |
| M14 | I | L | A | T | V | K | N | I | Q | E | K | E | V | L | T | L | G |
| M-Comp. | I | L | A | T | V | K | N | I | T | T | K | E | V | L | T | L | G |
| DENV4 | V | V | G | A | L | Q | G | F | T | T | K | E | V | L | T | Y | A |

|  | 120 | 122 | 123 | 124 | 126 | 128 | 129 | 132 | 136 | 140 | 141 | 145 | 148 | 150 | 154 | 156 | 157 |
|---|---|---|---|---|---|---|---|---|---|---|---|---|---|---|---|---|---|
| DENV3 | Q | L | E | P | E | K | V | Y | K | I | I | T | Q | Q | E | — | — |
| M12 | Q | L | E | K | T | N | L | Y | K | I | I | T | Q | Q | E | — | — |
| M14 | S | S | G | K | T | N | L | Y | K | I | I | T | Q | Q | E | — | — |
| M-Comp. | S | S | G | K | T | N | L | Y | K | I | I | T | Q | Q | E | — | — |
| DENV4 | S | S | G | K | T | N | L | I | E | V | V | N | T | A | D | S | N |

|  | 191 | 199 | 200 | 203 | 205 | 207 | 210 | 214 | 222 | 225 | 227 | 228 | 229 | 230 | 233 | 236 | 237 |
|---|---|---|---|---|---|---|---|---|---|---|---|---|---|---|---|---|---|
| DENV3 | L | L | T | N | A | M | R | F | S | T | E | T | P | T | R | L | L |
| M12 | L | L | K | K | T | M | R | F | A | T | E | T | P | T | R | L | L |
| M14 | L | L | K | K | T | M | R | F | A | T | S | E | V | H | Y | L | L |
| M-Comp. | L | L | K | K | T | M | K | F | A | T | S | E | V | H | Y | L | L |
| DENV4 | I | M | K | K | T | L | K | L | A | D | S | E | V | H | Y | R | M |

|  | 286 | 287 | 288 | 290 | 293 | 294 | 300 | 303 | 304 | 305 | 307 | 308 | 309 | 312 | 313 | 320 | 321 |
|---|---|---|---|---|---|---|---|---|---|---|---|---|---|---|---|---|---|
| DENV3 | R | L | K | D | E | L | A | T | N | T | V | L | K | V | S | I | L |
| M12 | R | L | K | D | E | L | A | T | N | T | V | L | K | V | S | I | L |
| M14 | R | L | K | D | E | L | A | T | N | T | V | L | K | V | S | I | L |
| M-Comp. | R | L | K | D | E | L | A | T | N | T | V | L | K | V | S | I | L |
| DENV4 | K | V | R | E | R | I | T | S | G | K | S | I | D | M | A | T | V |

|  | 344 | 345 | 346 | 347 | 348 | 351 | 353 | 354 | 355 | 357 | 358 | 359 | 360 | 361 | 362 | 363 | 364 |
|---|---|---|---|---|---|---|---|---|---|---|---|---|---|---|---|---|---|
| DENV3 | G | K | A | H | N | L | T | A | N | V | V | T | K | K | E | E | P |
| M12 | G | K | A | H | N | L | T | A | N | V | V | T | K | K | E | E | P |
| M14 | G | K | A | H | N | L | T | A | N | V | V | T | K | K | E | E | P |
| M-Comp. | G | K | A | H | N | L | T | A | N | V | V | T | K | K | E | E | P |
| DENV4 | K | E | K | V | V | V | S | S | T | L | A | E | N | T | N | S | V |

|  | 64 | 66 | 71 | 72 | 80 | 81 | 83 | 89 | 91 | 93 | 94 | 95 | 96 | 112 | 113 |
|---|---|---|---|---|---|---|---|---|---|---|---|---|---|---|---|
| DENV3 | K | T | D | S | A | V | P | N | V | K | H | T | Y | S | L |
| M12 | K | T | D | S | A | V | P | N | V | K | H | T | Y | S | L |
| M14 | K | T | D | S | A | V | P | N | V | K | H | T | Y | S | L |
| M-Comp. | S | S | A | S | A | Y | K | Q | I | K | H | T | Y | S | L |
| DENV4 | S | S | A | T | P | Y | K | Q | I | R | R | D | V | G | V |

|  | 158 | 163 | 167 | 168 | 169 | 170 | 171 | 173 | 174 | 177 | 180 | 182 | 184 | 185 | 186 | 189 |
|---|---|---|---|---|---|---|---|---|---|---|---|---|---|---|---|---|
| DENV3 | Q | E | Q | A | S | T | T | A | I | E | T | G | E | C | S | T |
| M12 | Q | E | Q | A | S | T | T | A | I | E | T | G | E | C | S | T |
| M14 | Q | E | Q | A | S | T | T | A | I | E | T | G | E | C | S | T |
| M-Comp. | Q | E | Q | A | S | T | T | A | I | E | T | G | E | C | S | T |
| DENV4 | H | T | R | S | P | S | V | V | K | D | E | T | D | C | E | S |

|  | 242 | 243 | 247 | 249 | 251 | 262 | 265 | 270 | 271 | 272 | 273 | 274 | 276 | 277 | 278 |
|---|---|---|---|---|---|---|---|---|---|---|---|---|---|---|---|
| DENV3 | N | A | K | E | V | T | T | I | Q | N | S | G | T | S | I |
| M12 | N | A | K | E | V | T | T | T | D | S | G | D | T | H | M |
| M14 | N | A | K | E | V | T | T | V | D | S | G | D | T | H | M |
| M-Comp. | N | A | R | E | T | T | T | V | D | S | G | D | T | H | M |
| DENV4 | V | P | R | D | T | S | A | V | D | S | G | D | N | H | M |

|  | 322 | 325 | 327 | 329 | 330 | 335 | 337 | 338 | 339 | 340 | 342 | 343 |
|---|---|---|---|---|---|---|---|---|---|---|---|---|
| DENV3 | I | E | K | E | D | I | F | S | T | E | G | Q |
| M12 | I | E | K | E | D | I | F | S | T | E | G | Q |
| M14 | I | E | K | E | D | I | F | S | T | E | G | Q |
| M-Comp. | I | E | K | E | D | I | F | S | T | E | G | Q |
| DENV4 | V | K | E | A | G | V | I | E | I | R | V | N |

|  | 365 | 369 | 375 | 377 | 382 | 384 | 385 | 388 | 389 | 390 | 392 | 393 |
|---|---|---|---|---|---|---|---|---|---|---|---|---|
| DENV3 | V | A | E | N | I | D | N | K | I | N | Y | K |
| M12 | V | A | E | N | I | D | N | K | I | N | Y | K |

TABLE 6-continued

3-4 Matrix.

| M14    | V | A | E | N | I | D | N | K | I | N | Y | K |
| M-Comp.| V | A | E | N | I | D | N | K | I | N | Y | K |
| DENV4  | T | L | D | Y | V | N | S | T | L | H | F | R |

TABLE 7

Amino acid residues of the DI-DII hinge region and DIII region of dengue virus E glycoproteins of DENV1, DENV2, DENV3, DENV4 and corresponding regions of YFV and JEV. Amino acid numbering is based on amino acid sequences shown in the sequence alignment in FIG. 7.

| Epitope | Amino acid residues |
| --- | --- |
| DI-DII hinge of E protein | DENV1, 2, 3, 4: AA 47, 48, 49, 50, 51, 52, 53, 54, 55, 56, 67, 58, 59<br>YFV: AA 47, 48, 49, 50, 51, 52, 53, 54, 55, 56, 67, 58, 59<br>JEV: AA 47, 48, 49, 50, 51, 52, 53, 54, 55, 56, 67, 58, 59<br>DENV1, 2, 3, 4: AA 124, 125, 126, 127, 128, 129, 130, 131, 132, 133<br>YFV: AA 124, 125, 126, 127, 128, 129, 130, 131, 132, 133<br>JEV: AA 124, 125, 126, 127, 128, 129, 130, 131, 132, 133<br>DENV3: AA 199, 200, 201, 202, 203, 204, 205, 206, 207, 208, 209, 210, 211, 212, 213, 214, 215, 216, 217, 218, 219, 220, 221, 222<br>DENV1, 2, 4: AA 201, 202, 203, 204, 205, 206, 207, 208, 209, 210, 211, 212, 213, 214, 215, 216, 217, 218, 219, 220, 221, 222, 223, 224<br>YFV: AA 198, 199, 200, 201, 202, 203, 204, 205, 206, 207, 208, 209, 210, 211, 212, 213, 214, 215, 216, 217, 218, 219, 220<br>JEV: AA 206, 207, 208, 209, 210, 211, 212, 213, 214, 215, 216, 217, 218, 219, 220, 221, 222, 223, 224, 225, 226, 227, 228 |
| DIII of E protein | DENV3: AA 269-278<br>DENV1, 2, 4: AA 271-280<br>YFV: AA 265-278<br>JEV: AA 273-282<br>DENV3: AA 305, 306, 307, 308<br>DENV1, 2, 4: AA 307, 308, 309, 310<br>YFV: AA 305, 306, 307, 308<br>JEV: AA 309, 310, 311, 312<br>DENV3: AA 323, 324, 325<br>DENV1, 2, 4: AA 325, 326, 327<br>YFV: AA 323, 324, 325<br>JEV: AA 327, 328, 329<br>DENV3: AA 359, 360, 361, 362<br>DENV1, 2, 4: AA 361, 362, 363, 364<br>YFV: AA 359, 360, 361, 362<br>JEV: AA 364, 365, 366, 367, 368, 369<br>DENV3: AA 382, 383<br>DENV1, 2, 4: AA 384, 385<br>YFV: AA 382, 383<br>JEV: AA 389, 390 |

What is claimed is:

1. A chimeric dengue virus E glycoprotein comprising an amino acid sequence selected from the group consisting of:

(SEQ ID NO: 8)
MRCIGISNRDFVEGVSGGSWVDIVLEHGSCVTTMAKNKPTLDFELIKTEA

KEVALLRTYCIEAKLTNTTTESRCPTQGEPSLNEEQDKRFVCKHSMVDRG

WGNGCGLFGKGGIVTCAMFTCKKKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTQGSNWIQKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK;

(SEQ ID NO: 9)
MRCIGISNRDFVEGVSGGSWVDIVLEHGSCVTTMAKNKPTLDFELIKTEA

KEVALLRTYCIEAKLTNTTTESRCPTQGEPSLNEEQDKRFVCKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK;

(SEQ ID NO: 10)
MRCIGISNRDFVEGVSGGSWVDIVLEHGSCVTTMAKNKPTLDFELTKTTA

KEVALLRTYCIEASISNITTASRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKRQDV

TVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK;

(SEQ ID NO: 22)
MRCIGISNRDFVEGVSGGSWVDIVLEHGSCVTTMAKNKPTLDFELTKTTA

KEVALLRTYCIEAKLTNTTTESRCPTQGEPSLNEEQDKRFVCKHSMVDRG

WGNGCGLFGKGGIVTCAKFSCSGKITGNLVQIENLEYTIVVTPHSGEEHA

VGNDTGKHGKEIKVTPQSSITEAELTGYGTVTMECSPRSGIDFNEMVLLK

MKKKTWLVHKQWFLDLPLPWTAGADTSEVHWNDKETLVTFKNPHAKKQDV

VVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK.

(SEQ ID NO: 24)
MRCIGISNRDFVEGVSGGSWVDIVLEHGSCVTTMAKNKPTLDFELTKTTA

KEVALLRTYCIEAKISNITTESRCPTQGEPYLKEEQDQQYICKHSMVDRG

WGNGCGLFGKGGIVTCAKFSCSGKITGNLVQPENLEYTIVVTPHSGEEHA

VGNDTGKHGKEIKVTPQSSITEAELTGYGTVTMECSPRTGLDFNEMVLLK

MKKKTWLVHKQWFLDLPLPWTAGADTSEVHWNYKETLVTFKNPHAKKQDV

TVLGSQEGAMHTALTGATEVDSGDGNHMFAGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK;

(SEQ ID NO: 25)
MRCIGISNRDFVEGVSGGSWVDIVLEHGSCVTTMAKNKPTLDFELIKTEA

KEVALLRTYCIEASISNITTATRCPTQGEPYLKEEQDQQYICRRDVVDRG

WGNGCGLFGKGGVVTCAKFSCSGKITGNLVQIENLEYTIVVTPHSGEEHA

VGNDTGKHGKEIKVTPQSSITEAELTGYGTVTMECSPRTGLDFNEMILMK

MKKKTWLVHKQWFLDLPLPWTAGADTSEVHWNYKERMVTFKVPHAKRQDV

TVLGSQEGAMHSALAGATEVDSGDGNHMFTGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVDPGQLKLNWFKK;

any combination thereof.

2. A flavivirus particle comprising the chimeric dengue virus E glycoprotein of claim 1.

3. A virus like particle (VLP) comprising the chimeric dengue virus E glycoprotein of claim 1.

4. A composition comprising the chimeric dengue virus E glycoprotein of claim 1, in a pharmaceutically acceptable carrier.

5. A method of producing an immune response to a dengue virus in a subject, the method comprising administering to the subject an effective amount of the chimeric dengue virus E glycoprotein of claim 1.

6. A method of treating a dengue virus infection in a subject, the method comprising administering to the subject an effective amount of the chimeric dengue virus E glycoprotein of claim 1.

7. A method of protecting a subject from the effects of dengue virus infection, the method comprising administering to the subject an effective amount of the chimeric dengue virus E glycoprotein of claim 1.

8. A chimeric dengue virus E glycoprotein comprising a dengue virus E glycoprotein backbone that comprises the following amino acid substitutions, wherein the amino acid residue numbering is based on the reference amino acid sequence of SEQ ID NO:2:

I46T, E49T, Q52E, P53V, T55L, K58T, K64S, L65I, T66S, T68I, E71A, S72T, S81Y, N83K, K88Q, R89Q, F90Y, V91I, K93R, H94R, S95D, M96V, I113V, M118K, T120S, K22S, K123G N124K, M125I, E126T, K128N, V129L, P132I, G177D, T189S, L191I, V197I, L199M, Q200K, N203K, A205T, R210K, L221T, P222A, Q227S, G228E, S229V, T232N, Q233Y, T236R, L237M, N242V, K247R, V251T, T262S, T265A, I270V, Q271D, M272S, S273G, S274D, L277H, L278M, and T280A.

9. A flavivirus particle or virus like particle (VLP) comprising the E glycoprotein of claim 8.

10. A composition comprising the E glycoprotein of claim 8 in a pharmaceutically acceptable carrier.

11. A method of producing an immune response to a dengue virus in a subject, the method comprising administering to the subject an effective amount of the chimeric dengue virus E glycoprotein of claim 8.

12. A method of treating a dengue virus infection in a subject, the method comprising administering to the subject an effective amount of the chimeric dengue virus E glycoprotein of claim 8.

13. A method of protecting a subject from the effects of dengue virus infection, the method comprising administering to the subject an effective amount of the chimeric dengue virus E glycoprotein of claim 8.

* * * * *

```
                     SEQUENCE LISTING

<160> NUMBER OF SEQ ID NOS: 25

<210> SEQ ID NO 1
<211> LENGTH: 410
<212> TYPE: PRT
<213> ORGANISM: Dengue virus type 1

<400> SEQUENCE: 1

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
```

```
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Glu Lys Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg
                405                 410

<210> SEQ ID NO 2
<211> LENGTH: 410
<212> TYPE: PRT
<213> ORGANISM: Dengue virus type 2

<400> SEQUENCE: 2

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80
```

-continued

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Val Val Gln Pro Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Asp Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys
                405                 410

<210> SEQ ID NO 3
<211> LENGTH: 410
<212> TYPE: PRT
<213> ORGANISM: Dengue virus type 3

<400> SEQUENCE: 3

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

```
Glu Ala Thr Gln Leu Ala Thr Leu Arg Lys Leu Cys Ile Glu Gly Lys
            50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
                100                 105                 110

Leu Val Thr Cys Ala Lys Phe Gln Cys Leu Glu Pro Ile Glu Gly Lys
            115                 120                 125

Val Val Gln Tyr Glu Asn Leu Lys Tyr Thr Val Ile Ile Thr Val His
        130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
                180                 185                 190

Glu Met Ile Leu Leu Thr Met Lys Asn Lys Ala Trp Met Val His Arg
            195                 200                 205

Gln Trp Phe Phe Asp Leu Pro Leu Pro Trp Thr Ser Gly Ala Thr Thr
        210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
                260                 265                 270

Gly Thr Ser Ile Phe Ala Gly His Leu Lys Cys Arg Leu Lys Met Asp
            275                 280                 285

Lys Leu Glu Leu Lys Gly Met Ser Tyr Ala Met Cys Thr Asn Thr Phe
        290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
                340                 345                 350

Asn Pro Val Val Thr Lys Lys Glu Glu Pro Val Asn Ile Glu Ala Glu
            355                 360                 365

Pro Pro Phe Gly Glu Ser Asn Ile Val Ile Gly Ile Gly Asp Asn Ala
        370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met
                405                 410

<210> SEQ ID NO 4
<211> LENGTH: 410
<212> TYPE: PRT
<213> ORGANISM: Dengue virus type 4

<400> SEQUENCE: 4

Met Arg Cys Val Gly Val Gly Asn Arg Asp Phe Val Glu Gly Val Ser
```

```
1               5                   10                  15
Gly Gly Ala Trp Val Asp Leu Val Leu Glu His Gly Cys Val Thr
                20                  25                  30
Thr Met Ala Gln Gly Lys Pro Thr Leu Asp Phe Glu Leu Thr Lys Thr
            35                  40                  45
Thr Ala Lys Glu Val Ala Leu Leu Arg Thr Tyr Cys Ile Glu Ala Ser
    50                  55                  60
Ile Ser Asn Ile Thr Thr Ala Thr Arg Cys Pro Thr Gln Gly Glu Pro
65                  70                  75                  80
Tyr Leu Lys Glu Glu Gln Asp Gln Gln Tyr Ile Cys Arg Arg Asp Val
                85                  90                  95
Val Asp Arg Gly Trp Gly Asn Gly Cys Gly Leu Phe Gly Lys Gly Gly
                100                 105                 110
Val Val Thr Cys Ala Lys Phe Ser Cys Ser Gly Lys Ile Thr Gly Asn
                115                 120                 125
Leu Val Gln Ile Glu Asn Leu Glu Tyr Thr Val Val Thr Val His
        130                 135                 140
Asn Gly Asp Thr His Ala Val Gly Asn Asp Thr Ser Asn His Gly Val
145                 150                 155                 160
Thr Ala Thr Ile Thr Pro Arg Ser Pro Ser Val Glu Val Lys Leu Pro
                165                 170                 175
Asp Tyr Gly Glu Leu Thr Leu Asp Cys Glu Pro Arg Ser Gly Ile Asp
            180                 185                 190
Phe Asn Glu Met Ile Leu Met Lys Met Lys Lys Thr Trp Leu Val
            195                 200                 205
His Lys Gln Trp Phe Leu Asp Leu Pro Leu Pro Trp Thr Ala Gly Ala
        210                 215                 220
Asp Thr Ser Glu Val His Trp Asn Tyr Lys Glu Arg Met Val Thr Phe
225                 230                 235                 240
Lys Val Pro His Ala Lys Arg Gln Asp Val Thr Val Leu Gly Ser Gln
                245                 250                 255
Glu Gly Ala Met His Ser Ala Leu Ala Gly Ala Thr Glu Val Asp Ser
            260                 265                 270
Gly Asp Gly Asn His Met Phe Ala Gly His Leu Lys Cys Lys Val Arg
        275                 280                 285
Met Glu Lys Leu Arg Ile Lys Gly Met Ser Tyr Thr Met Cys Ser Gly
        290                 295                 300
Lys Phe Ser Ile Asp Lys Glu Met Ala Glu Thr Gln His Gly Thr Thr
305                 310                 315                 320
Val Val Lys Val Lys Tyr Glu Gly Ala Gly Ala Pro Cys Lys Val Pro
                325                 330                 335
Ile Glu Ile Arg Asp Val Asn Lys Glu Lys Val Val Gly Arg Val Ile
            340                 345                 350
Ser Ser Thr Pro Leu Ala Glu Asn Thr Asn Ser Val Thr Asn Ile Glu
            355                 360                 365
Leu Glu Pro Pro Phe Gly Asp Ser Tyr Ile Val Ile Gly Val Gly Asn
        370                 375                 380
Ser Ala Leu Thr Leu His Trp Phe Arg Lys Gly Ser Ser Ile Gly Lys
385                 390                 395                 400
Met Phe Glu Ser Thr Tyr Arg Gly Ala Lys
                405                 410

<210> SEQ ID NO 5
```

<211> LENGTH: 394
<212> TYPE: PRT
<213> ORGANISM: Artificial Sequence
<220> FEATURE:
<223> OTHER INFORMATION: chimeric dengue virus E glycoprotein DENV1/4 M12

<400> SEQUENCE: 5

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Lys Glu Val Ala Leu Leu Arg Thr Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Ile Thr Gly Asn
        115                 120                 125

Leu Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Ser Thr Ser Gln Glu Thr Trp Asn Arg Lys Asp Leu Leu Val Thr Phe
225                 230                 235                 240

Lys Thr Ala His Ala Lys Lys Gln Glu Val Val Leu Gly Ser Gln
                245                 250                 255

Glu Gly Ala Met His Thr Ala Leu Thr Gly Ala Thr Glu Val Asp Ser
            260                 265                 270

Gly Asp Thr Thr His Met Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
```

```
            370                 375                 380
Lys Ala Leu Lys Leu Ser Trp Phe Lys Lys
385                 390

<210> SEQ ID NO 6
<211> LENGTH: 394
<212> TYPE: PRT
<213> ORGANISM: Artificial Sequence
<220> FEATURE:
<223> OTHER INFORMATION: chimeric dengue virus E glycoprotein DENV1/
      4 M14

<400> SEQUENCE: 6

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Lys Glu Val Ala Leu Leu Arg Thr Leu Cys Ile Glu Ala Lys
    50                  55                  60

Ile Ser Asn Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Ser Cys Ser Gly Lys Ile Thr Gly Asn
        115                 120                 125

Leu Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Lys Met Lys Lys Thr Trp Leu Val
        195                 200                 205

His Lys Gln Trp Phe Leu Asp Leu Pro Leu Pro Trp Thr Ala Gly Ala
    210                 215                 220

Ser Thr Ser Glu Val His Trp Asn Tyr Lys Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Val Asp Ser
            260                 265                 270

Gly Asp Thr Thr His Met Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335
```

```
Phe Ser Ser Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Val Gly Ala Gly Glu
        370                 375                 380

Lys Ala Leu Lys Leu Ser Trp Phe Lys Lys
385                 390

<210> SEQ ID NO 7
<211> LENGTH: 394
<212> TYPE: PRT
<213> ORGANISM: Artificial Sequence
<220> FEATURE:
<223> OTHER INFORMATION: chimeric dengue virus E glycoprotein DENV1/
      4 M-Complete

<400> SEQUENCE: 7

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Thr Lys Thr
        35                  40                  45

Thr Val Lys Glu Val Ala Leu Leu Arg Thr Leu Cys Ile Glu Ala Ser
    50                  55                  60

Ile Ser Asn Ile Thr Thr Ala Ser Arg Cys Pro Thr Gln Gly Glu Ala
65                  70                  75                  80

Tyr Leu Lys Glu Glu Gln Asp Gln Gln Tyr Ile Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Ser Cys Ser Gly Lys Ile Thr Gly Asn
        115                 120                 125

Leu Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Ser Thr Ser Glu Val His Trp Asn Tyr Lys Asp Leu Leu Val Thr Phe
225                 230                 235                 240

Lys Thr Ala His Ala Lys Arg Gln Glu Val Thr Val Leu Gly Ser Gln
                245                 250                 255

Glu Gly Ala Met His Thr Ala Leu Thr Gly Ala Thr Glu Val Asp Ser
            260                 265                 270

Gly Asp Thr Thr His Met Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300
```

-continued

```
Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
            325                 330                 335

Phe Ser Ser Gln Asp Glu Lys Gly Val Thr Gln Asn Gly Arg Leu Ile
        340                 345                 350

Thr Ala Asn Pro Ile Val Thr Asp Lys Glu Lys Pro Val Asn Ile Glu
    355                 360                 365

Ala Glu Pro Pro Phe Gly Glu Ser Tyr Ile Val Val Gly Ala Gly Glu
370                 375                 380

Lys Ala Leu Lys Leu Ser Trp Phe Lys Lys
385                 390

<210> SEQ ID NO 8
<211> LENGTH: 394
<212> TYPE: PRT
<213> ORGANISM: Artificial Sequence
<220> FEATURE:
<223> OTHER INFORMATION: chimeric dengue virus E glycoprotein DENV 2/
      4 M12

<400> SEQUENCE: 8

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Glu Val Ala Leu Leu Arg Thr Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Lys Ile Thr Gly Asn
        115                 120                 125

Leu Val Gln Pro Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Val Asp Ser
```

-continued

```
            260                 265                 270
Gly Asp Gly Asn His Met Phe Ala Gly His Leu Lys Cys Arg Leu Arg
        275                 280                 285
Met Asp Lys Leu Gln Leu Lys Gly Met Ser Tyr Ser Met Cys Thr Gly
    290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Met Asp Leu Glu Lys Arg His Val Leu Gly Arg Leu Ile
            340                 345                 350
Thr Val Asn Pro Ile Val Thr Glu Lys Asp Ser Pro Val Asn Ile Glu
        355                 360                 365
Ala Glu Pro Pro Phe Gly Asp Ser Tyr Ile Ile Ile Gly Val Asp Pro
    370                 375                 380
Gly Gln Leu Lys Leu Asn Trp Phe Lys Lys
385                 390
```

<210> SEQ ID NO 9
<211> LENGTH: 394
<212> TYPE: PRT
<213> ORGANISM: Artificial Sequence
<220> FEATURE:
<223> OTHER INFORMATION: chimeric dengue virus E glycoprotein DENV 2/
    4 M14

<400> SEQUENCE: 9

```
Met Arg Cys Ile Gly Ile Ser Asn Arg Asp Phe Val Glu Gly Val Ser
1               5                   10                  15
Gly Gly Ser Trp Val Asp Ile Val Leu Glu His Gly Ser Cys Val Thr
            20                  25                  30
Thr Met Ala Lys Asn Lys Pro Thr Leu Asp Phe Glu Leu Ile Lys Thr
        35                  40                  45
Glu Ala Lys Glu Val Ala Leu Leu Arg Thr Tyr Cys Ile Glu Ala Lys
    50                  55                  60
Leu Thr Asn Thr Thr Thr Glu Ser Arg Cys Pro Thr Gln Gly Glu Pro
65                  70                  75                  80
Ser Leu Asn Glu Glu Gln Asp Lys Arg Phe Val Cys Lys His Ser Met
                85                  90                  95
Val Asp Arg Gly Trp Gly Asn Gly Cys Gly Leu Phe Gly Lys Gly Gly
            100                 105                 110
Ile Val Thr Cys Ala Lys Phe Ser Cys Ser Gly Lys Ile Thr Gly Asn
        115                 120                 125
Leu Val Gln Pro Glu Asn Leu Glu Tyr Thr Ile Val Val Thr Pro His
    130                 135                 140
Ser Gly Glu Glu His Ala Val Gly Asn Asp Thr Gly Lys His Gly Lys
145                 150                 155                 160
Glu Ile Lys Val Thr Pro Gln Ser Ser Ile Thr Glu Ala Glu Leu Thr
                165                 170                 175
Gly Tyr Gly Thr Val Thr Met Glu Cys Ser Pro Arg Thr Gly Leu Asp
            180                 185                 190
Phe Asn Glu Met Val Leu Leu Lys Met Lys Lys Lys Thr Trp Leu Val
        195                 200                 205
His Lys Gln Trp Phe Leu Asp Leu Pro Leu Pro Trp Thr Ala Gly Ala
    210                 215                 220
```

```
Asp Thr Ser Glu Val His Trp Asn Tyr Lys Glu Thr Leu Val Thr Phe
225                 230                 235                 240

Lys Asn Pro His Ala Lys Lys Gln Asp Val Val Leu Gly Ser Gln
            245                 250                 255

Glu Gly Ala Met His Thr Ala Leu Thr Gly Ala Thr Glu Val Asp Ser
                260                 265                 270

Gly Asp Gly Asn His Met Phe Ala Gly His Leu Lys Cys Arg Leu Arg
            275                 280                 285

Met Asp Lys Leu Gln Leu Lys Gly Met Ser Tyr Ser Met Cys Thr Gly
        290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
                355                 360                 365

Ala Glu Pro Pro Phe Gly Asp Ser Tyr Ile Ile Ile Gly Val Asp Pro
370                 375                 380

Gly Gln Leu Lys Leu Asn Trp Phe Lys Lys
385                 390

<210> SEQ ID NO 10
<211> LENGTH: 394
<212> TYPE: PRT
<213> ORGANISM: Artificial Sequence
<220> FEATURE:
<223> OTHER INFORMATION: chimeric dengue virus E glycoprotein DENV 2/
      4 M-complete

<400> SEQUENCE: 10

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Ser Arg Cys Pro Thr Gln Gly Glu Pro
65                  70                  75                  80

Tyr Leu Lys Glu Glu Gln Asp Gln Gln Tyr Ile Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Lys Phe Ser Cys Ser Gly Lys Ile Thr Gly Asn
        115                 120                 125

Leu Val Gln Pro Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190
```

```
Phe Asn Glu Met Val Leu Leu Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Thr Leu Val Thr Phe
225                 230                 235                 240

Lys Asn Pro His Ala Lys Arg Gln Asp Val Thr Val Leu Gly Ser Gln
                245                 250                 255

Glu Gly Ala Met His Thr Ala Leu Thr Gly Ala Thr Glu Val Asp Ser
                260                 265                 270

Gly Asp Gly Asn His Met Phe Ala Gly His Leu Lys Cys Arg Leu Arg
                275                 280                 285

Met Asp Lys Leu Gln Leu Lys Gly Met Ser Tyr Ser Met Cys Thr Gly
290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
                355                 360                 365

Ala Glu Pro Pro Phe Gly Asp Ser Tyr Ile Ile Ile Gly Val Asp Pro
                370                 375                 380

Gly Gln Leu Lys Leu Asn Trp Phe Lys Lys
385                 390

<210> SEQ ID NO 11
<211> LENGTH: 392
<212> TYPE: PRT
<213> ORGANISM: Artificial Sequence
<220> FEATURE:
<223> OTHER INFORMATION: chimeric dengue virus E glycoprotein DENV 3/
      4 M12

<400> SEQUENCE: 11

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Gln Lys Thr
            35                  40                  45

Glu Ala Lys Glu Val Ala Leu Leu Arg Thr Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
                100                 105                 110

Leu Val Thr Cys Ala Lys Phe Gln Cys Leu Glu Lys Ile Thr Gly Asn
            115                 120                 125

Leu Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
```

```
                145                 150                 155                 160
Glu Ile Thr Pro Gln Ala Ser Thr Thr Glu Ala Ile Leu Pro Glu Tyr
                    165                 170                 175
Gly Thr Leu Gly Leu Glu Cys Ser Pro Arg Thr Gly Leu Asp Phe Asn
                    180                 185                 190
Glu Met Ile Leu Leu Lys Met Lys Lys Thr Trp Met Val His Arg
                    195                 200                 205
Gln Trp Phe Phe Asp Leu Pro Leu Pro Trp Thr Ala Gly Ala Thr Thr
                    210                 215                 220
Glu Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                    245                 250                 255
Ala Met His Thr Ala Leu Thr Gly Ala Thr Glu Val Asp Ser Gly Asp
                    260                 265                 270
Gly Thr His Met Phe Ala Gly His Leu Lys Cys Arg Leu Lys Met Asp
                    275                 280                 285
Lys Leu Glu Leu Lys Gly Met Ser Tyr Ala Met Cys Thr Asn Thr Phe
                    290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                    325                 330                 335
Thr Glu Asp Gly Gln Gly Lys Ala His Asn Gly Arg Leu Ile Thr Ala
                    340                 345                 350
Asn Pro Val Val Thr Lys Lys Glu Glu Pro Val Asn Ile Glu Ala Glu
                    355                 360                 365
Pro Pro Phe Gly Glu Ser Asn Ile Val Ile Gly Ile Gly Asp Asn Ala
                    370                 375                 380
Leu Lys Ile Asn Trp Tyr Lys Lys
385                 390

<210> SEQ ID NO 12
<211> LENGTH: 392
<212> TYPE: PRT
<213> ORGANISM: Artificial Sequence
<220> FEATURE:
<223> OTHER INFORMATION: chimeric dengue virus E glycoprotein DENV 3/
      4 M14

<400> SEQUENCE: 12

Met Arg Cys Val Gly Ile Gly Asn Arg Asp Phe Val Glu Gly Leu Ser
1               5                   10                  15
Gly Ala Thr Trp Val Asp Val Val Leu Glu His Gly Gly Cys Val Thr
                    20                  25                  30
Thr Met Ala Lys Asn Lys Pro Thr Leu Asp Ile Glu Leu Gln Lys Thr
                    35                  40                  45
Glu Ala Lys Glu Val Ala Leu Leu Arg Thr Leu Cys Ile Glu Gly Lys
                    50                  55                  60
Ile Thr Asn Ile Thr Thr Asp Ser Arg Cys Pro Thr Gln Gly Glu Ala
65                  70                  75                  80
Val Leu Pro Glu Glu Gln Asp Gln Asn Tyr Val Cys Lys His Thr Tyr
                    85                  90                  95
Val Asp Arg Gly Trp Gly Asn Gly Cys Gly Leu Phe Gly Lys Gly Ser
                    100                 105                 110
```

```
Leu Val Thr Cys Ala Lys Phe Ser Cys Ser Gly Lys Ile Thr Gly Asn
            115                 120                 125

Leu Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Lys Met Lys Lys Thr Trp Met Val His Arg
    195                 200                 205

Gln Trp Phe Phe Asp Leu Pro Leu Pro Trp Thr Ala Gly Ala Thr Thr
    210                 215                 220

Ser Glu Val His Trp Asn Tyr Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Val Asp Ser Gly Asp
            260                 265                 270

Gly Thr His Met Phe Ala Gly His Leu Lys Cys Arg Leu Lys Met Asp
    275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
            355                 360                 365

Pro Pro Phe Gly Glu Ser Asn Ile Val Ile Gly Ile Gly Asp Asn Ala
    370                 375                 380

Leu Lys Ile Asn Trp Tyr Lys Lys
385                 390

<210> SEQ ID NO 13
<211> LENGTH: 392
<212> TYPE: PRT
<213> ORGANISM: Artificial Sequence
<220> FEATURE:
<223> OTHER INFORMATION: chimeric dengue virus E glycoproeitn DENV 3/
      4 M-Complete

<400> SEQUENCE: 13

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Thr Lys Thr
        35                  40                  45

Thr Ala Lys Glu Val Ala Leu Leu Arg Thr Leu Cys Ile Glu Gly Ser
    50                  55                  60

Ile Ser Asn Ile Thr Thr Ala Ser Arg Cys Pro Thr Gln Gly Glu Ala
65                  70                  75                  80
```

```
Tyr Leu Lys Glu Glu Gln Asp Gln Gln Tyr Ile Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Ser Cys Ser Gly Lys Ile Thr Gly Asn
        115                 120                 125

Leu Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Lys Met Lys Lys Thr Trp Met Val His Lys
        195                 200                 205

Gln Trp Phe Phe Asp Leu Pro Leu Pro Trp Thr Ala Gly Ala Thr Thr
    210                 215                 220

Ser Glu Val His Trp Asn Tyr Lys Glu Leu Leu Val Thr Phe Lys Asn
225                 230                 235                 240

Ala His Ala Lys Arg Gln Glu Val Thr Val Leu Gly Ser Gln Glu Gly
                245                 250                 255

Ala Met His Thr Ala Leu Thr Gly Ala Thr Glu Val Asp Ser Gly Asp
            260                 265                 270

Gly Thr His Met Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Asn Ala
    370                 375                 380

Leu Lys Ile Asn Trp Tyr Lys Lys
385                 390

<210> SEQ ID NO 14
<211> LENGTH: 3391
<212> TYPE: PRT
<213> ORGANISM: Artificial Sequence
<220> FEATURE:
<223> OTHER INFORMATION: chimeric dengue virus DENV 2/4 M-Complete
      modified swap

<400> SEQUENCE: 14

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
```

```
                    35                  40                  45
Ala Leu Val Ala Phe Leu Arg Phe Leu Thr Ile Pro Pro Thr Ala Gly
 50                  55                  60

Ile Leu Lys Arg Trp Gly Thr Ile Lys Lys Ser Lys Ala Ile Asn Val
 65                  70                  75                  80

Leu Arg Gly Phe Arg Lys Glu Ile Gly Arg Met Leu Asn Ile Leu Asn
                     85                  90                  95

Arg Arg Arg Arg Ser Ala Gly Met Ile Ile Met Leu Ile Pro Thr Val
                100                 105                 110

Met Ala Phe His Leu Thr Thr Arg Asn Gly Glu Pro His Met Ile Val
                115                 120                 125

Ser Arg Gln Glu Lys Gly Lys Ser Leu Leu Phe Lys Thr Glu Asp Gly
130                 135                 140

Val Asn Met Cys Thr Leu Met Ala Met Asp Leu Gly Glu Leu Cys Glu
145                 150                 155                 160

Asp Thr Ile Thr Tyr Asn Cys Pro Leu Leu Arg Gln Asn Glu Pro Glu
                165                 170                 175

Asp Ile Asp Cys Trp Cys Asn Ser Thr Ser Thr Trp Val Thr Tyr Gly
                180                 185                 190

Thr Cys Thr Thr Thr Gly Glu His Arg Arg Glu Lys Arg Ser Val Ala
                195                 200                 205

Leu Val Pro His Val Gly Met Gly Leu Glu Thr Arg Thr Glu Thr Trp
210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Ala Leu Ile Phe Ile Leu Leu
                260                 265                 270

Thr Ala Val Ala Pro Ser Met Thr Met Arg Cys Ile Gly Ile Ser Asn
                275                 280                 285

Arg Asp Phe Val Glu Gly Val Ser Gly Gly Ser Trp Val Asp Ile Val
290                 295                 300

Leu Glu His Gly Ser Cys Val Thr Met Ala Lys Asn Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Lys Ile Ser Asn Ile Thr Thr Glu Ser
                340                 345                 350

Arg Cys Pro Thr Gln Gly Glu Pro Tyr Leu Lys Glu Glu Gln Asp Gln
                355                 360                 365

Gln Tyr Ile Cys Lys His Ser Met Val Asp Arg Gly Trp Gly Asn Gly
370                 375                 380

Cys Gly Leu Phe Gly Lys Gly Ile Val Thr Cys Ala Lys Phe Ser
385                 390                 395                 400

Cys Ser Gly Lys Ile Thr Gly Asn Leu Val Gln Pro Glu Asn Leu Glu
                405                 410                 415

Tyr Thr Ile Val Val Thr Pro His Ser Gly Glu Glu His Ala Val Gly
                420                 425                 430

Asn Asp Thr Gly Lys His Gly Lys Glu Ile Lys Val Thr Pro Gln Ser
                435                 440                 445

Ser Ile Thr Glu Ala Glu Leu Thr Gly Tyr Gly Thr Val Thr Met Glu
450                 455                 460
```

```
Cys Ser Pro Arg Thr Gly Leu Asp Phe Asn Glu Met Val Leu Leu Lys
465                 470                 475                 480

Met Lys Lys Lys Thr Trp Leu Val His Lys Gln Trp Phe Leu Asp Leu
            485                 490                 495

Pro Leu Pro Trp Thr Ala Gly Ala Asp Thr Ser Glu Val His Trp Asn
        500                 505                 510

Tyr Lys Glu Thr Leu Val Thr Phe Lys Asn Pro His Ala Lys Lys Gln
    515                 520                 525

Asp Val Thr Val Leu Gly Ser Gln Glu Gly Ala Met His Thr Ala Leu
530                 535                 540

Thr Gly Ala Thr Glu Val Asp Ser Gly Asp Gly Asn His Met Phe Ala
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Asp Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Ile Val Thr Leu Tyr
        755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala Gln Glu Glu Gly Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ala Glu Asn Glu Val Lys Leu Thr Ile Met
850                 855                 860

Thr Gly Asp Ile Lys Gly Ile Met Gln Ala Gly Lys Arg Ser Leu Arg
865                 870                 875                 880
```

```
Pro Gln Pro Thr Glu Leu Lys Tyr Ser Trp Lys Thr Gly Lys Ala
            885                 890                 895

Lys Met Leu Ser Thr Glu Ser His Asn Gln Thr Phe Leu Ile Asp Gly
        900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Asn Ile Trp Leu
    930                 935                 940

Lys Leu Lys Glu Lys Gln Asp Ala Phe Cys Asp Ser Lys Leu Met Ser
945                 950                 955                 960

Ala Ala Ile Lys Asp Asn Arg Ala Val His Ala Asp Met Gly Tyr Trp
            965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
            995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Ala Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Val Val Met Val Gly
    1175                1180                1185

Ala Thr Met Thr Asp Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Lys Glu Leu Met Met Thr Thr Ile
    1220                1225                1230

Gly Ile Val Leu Leu Ser Gln Ser Thr Ile Pro Glu Thr Ile Leu
    1235                1240                1245

Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
```

```
                1280                1285                1290

Val Ser Cys Thr Ile Leu Ala Val Val Ser Val Ser Pro Leu Leu
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Arg Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650

Glu Asp Asp Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680
```

```
Arg Glu Ala Ile Lys Arg Gly Leu Arg Thr Leu Ile Leu Ala Pro
1685                1690                1695

Thr Arg Val Val Ala Ala Glu Met Glu Glu Ala Leu Arg Gly Leu
    1700            1705                1710

Pro Ile Arg Tyr Gln Thr Pro Ala Ile Arg Ala Glu His Thr Gly
    1715            1720                1725

Arg Glu Ile Val Asp Leu Met Cys His Ala Thr Phe Thr Met Arg
    1730            1735                1740

Leu Leu Ser Pro Val Arg Val Pro Asn Tyr Asn Leu Ile Ile Met
    1745            1750                1755

Asp Glu Ala His Phe Thr Asp Pro Ala Ser Ile Ala Ala Arg Gly
    1760            1765                1770

Tyr Ile Ser Thr Arg Val Glu Met Gly Glu Ala Ala Gly Ile Phe
    1775            1780                1785

Met Thr Ala Thr Pro Pro Gly Ser Arg Asp Pro Phe Pro Gln Ser
    1790            1795                1800

Asn Ala Pro Ile Ile Asp Glu Glu Arg Glu Ile Pro Glu Arg Ser
    1805            1810                1815

Trp Asn Ser Gly His Glu Trp Val Thr Asp Phe Lys Gly Lys Thr
    1820            1825                1830

Val Trp Phe Val Pro Ser Ile Lys Ala Gly Asn Asp Ile Ala Ala
    1835            1840                1845

Cys Leu Arg Lys Asn Gly Lys Lys Val Ile Gln Leu Ser Arg Lys
    1850            1855                1860

Thr Phe Asp Ser Glu Tyr Val Lys Thr Arg Thr Asn Asp Trp Asp
    1865            1870                1875

Phe Val Val Thr Thr Asp Ile Ser Glu Met Gly Ala Asn Phe Lys
    1880            1885                1890

Ala Glu Arg Val Ile Asp Pro Arg Arg Cys Met Lys Pro Val Ile
    1895            1900                1905

Leu Thr Asp Gly Glu Glu Arg Val Ile Leu Ala Gly Pro Met Pro
    1910            1915                1920

Val Thr His Ser Ser Ala Ala Gln Arg Arg Gly Arg Ile Gly Arg
    1925            1930                1935

Asn Pro Lys Asn Glu Asn Asp Gln Tyr Ile Tyr Met Gly Glu Pro
    1940            1945                1950

Leu Glu Asn Asp Glu Asp Cys Ala His Trp Lys Glu Ala Lys Met
    1955            1960                1965

Leu Leu Asp Asn Ile Asn Thr Pro Glu Gly Ile Ile Pro Ser Met
    1970            1975                1980

Phe Glu Pro Glu Arg Glu Lys Val Asp Ala Ile Asp Gly Glu Tyr
    1985            1990                1995

Arg Leu Arg Gly Glu Ala Arg Lys Thr Phe Val Asp Leu Met Arg
    2000            2005                2010

Arg Gly Asp Leu Pro Val Trp Leu Ala Tyr Lys Val Ala Ala Glu
    2015            2020                2025

Gly Ile Asn Tyr Ala Asp Arg Arg Trp Cys Phe Asp Gly Ile Lys
    2030            2035                2040

Asn Asn Gln Ile Leu Glu Glu Asn Val Glu Val Glu Ile Trp Thr
    2045            2050                2055

Lys Glu Gly Glu Arg Lys Lys Leu Lys Pro Arg Trp Leu Asp Ala
    2060            2065                2070
```

Arg Ile Tyr Ser Asp Pro Leu Ala Leu Lys Glu Phe Lys Glu Phe
2075                2080                2085

Ala Ala Gly Arg Lys Ser Leu Thr Leu Asn Leu Ile Thr Glu Met
2090                2095                2100

Gly Arg Leu Pro Thr Phe Met Thr Gln Lys Ala Arg Asp Ala Leu
2105                2110                2115

Asp Asn Leu Ala Val Leu His Thr Ala Glu Ala Gly Gly Arg Ala
2120                2125                2130

Tyr Asn His Ala Leu Ser Glu Leu Pro Glu Thr Leu Glu Thr Leu
2135                2140                2145

Leu Leu Leu Thr Leu Leu Ala Thr Val Thr Gly Gly Ile Phe Leu
2150                2155                2160

Phe Leu Met Ser Gly Arg Gly Ile Gly Lys Met Thr Leu Gly Met
2165                2170                2175

Cys Cys Ile Ile Thr Ala Ser Ile Leu Leu Trp Tyr Ala Gln Ile
2180                2185                2190

Gln Pro His Trp Ile Ala Ala Ser Ile Ile Leu Glu Phe Phe Leu
2195                2200                2205

Ile Val Leu Leu Ile Pro Glu Pro Glu Lys Gln Arg Thr Pro Gln
2210                2215                2220

Asp Asn Gln Leu Thr Tyr Val Val Ile Ala Ile Leu Thr Val Val
2225                2230                2235

Ala Ala Thr Met Ala Asn Glu Met Gly Phe Leu Glu Lys Thr Lys
2240                2245                2250

Lys Asp Leu Gly Leu Gly Ser Ile Ala Thr Gln Gln Pro Glu Ser
2255                2260                2265

Asn Ile Leu Asp Ile Asp Leu Arg Pro Ala Ser Ala Trp Thr Leu
2270                2275                2280

Tyr Ala Val Ala Thr Thr Phe Val Thr Pro Met Leu Arg His Ser
2285                2290                2295

Ile Glu Asn Ser Ser Val Asn Val Ser Leu Thr Ala Ile Ala Asn
2300                2305                2310

Gln Ala Thr Val Leu Met Gly Leu Gly Lys Gly Trp Pro Leu Ser
2315                2320                2325

Lys Met Asp Ile Gly Val Pro Leu Leu Ala Ile Gly Cys Tyr Ser
2330                2335                2340

Gln Val Asn Pro Ile Thr Leu Thr Ala Ala Leu Leu Leu Leu Val
2345                2350                2355

Ala His Tyr Ala Ile Ile Gly Pro Gly Leu Gln Ala Lys Ala Thr
2360                2365                2370

Arg Glu Ala Gln Lys Arg Ala Ala Ala Gly Ile Met Lys Asn Pro
2375                2380                2385

Thr Val Asp Gly Ile Thr Val Ile Asp Leu Asp Pro Ile Pro Tyr
2390                2395                2400

Asp Pro Lys Phe Glu Lys Gln Leu Gly Gln Val Met Leu Leu Val
2405                2410                2415

Leu Cys Val Thr Gln Val Leu Met Met Arg Thr Thr Trp Ala Leu
2420                2425                2430

Cys Glu Ala Leu Thr Leu Ala Thr Gly Pro Ile Ser Thr Leu Trp
2435                2440                2445

Glu Gly Asn Pro Gly Arg Phe Trp Asn Thr Thr Ile Ala Val Ser
2450                2455                2460

Met Ala Asn Ile Phe Arg Gly Ser Tyr Leu Ala Gly Ala Gly Leu

```
              2465                2470                2475
Leu Phe Ser Ile Met Lys Asn Thr Thr Asn Thr Arg Arg Gly Thr
        2480                2485                2490

Gly Asn Ile Gly Glu Thr Leu Gly Glu Lys Trp Lys Ser Arg Leu
        2495                2500                2505

Asn Ala Leu Gly Lys Ser Glu Phe Gln Ile Tyr Lys Lys Ser Gly
        2510                2515                2520

Ile Gln Glu Val Asp Arg Thr Leu Ala Lys Glu Gly Ile Lys Arg
        2525                2530                2535

Gly Glu Thr Asp His His Ala Val Ser Arg Gly Ser Ala Lys Leu
        2540                2545                2550

Arg Trp Phe Val Glu Arg Asn Met Val Thr Pro Glu Gly Lys Val
        2555                2560                2565

Val Asp Leu Gly Cys Gly Arg Gly Gly Trp Ser Tyr Tyr Cys Gly
        2570                2575                2580

Gly Leu Lys Asn Val Arg Glu Val Lys Gly Leu Thr Lys Gly Gly
        2585                2590                2595

Pro Gly His Glu Glu Pro Ile Pro Met Ser Thr Tyr Gly Trp Asn
        2600                2605                2610

Leu Val Arg Leu Gln Ser Gly Val Asp Val Phe Phe Ile Pro Pro
        2615                2620                2625

Glu Lys Cys Asp Thr Leu Leu Cys Asp Ile Gly Glu Ser Ser Pro
        2630                2635                2640

Asn Pro Thr Val Glu Ala Gly Arg Thr Leu Arg Val Leu Asn Leu
        2645                2650                2655

Val Glu Asn Trp Leu Asn Asn Thr Gln Phe Cys Ile Lys Val
        2660                2665                2670

Leu Asn Pro Tyr Met Pro Ser Val Ile Glu Lys Met Glu Thr Leu
        2675                2680                2685

Gln Arg Lys Tyr Gly Gly Ala Leu Val Arg Asn Pro Leu Ser Arg
        2690                2695                2700

Asn Ser Thr His Glu Met Tyr Trp Val Ser Asn Ala Ser Gly Asn
        2705                2710                2715

Ile Val Ser Ser Val Asn Met Ile Ser Arg Met Leu Ile Asn Arg
        2720                2725                2730

Phe Thr Met Arg His Lys Lys Ala Thr Tyr Glu Pro Asp Val Asp
        2735                2740                2745

Leu Gly Ser Gly Thr Arg Asn Ile Gly Ile Glu Ser Glu Ile Pro
        2750                2755                2760

Asn Leu Asp Ile Ile Gly Lys Arg Ile Glu Lys Ile Lys Gln Glu
        2765                2770                2775

His Glu Thr Ser Trp His Tyr Asp Gln Asp His Pro Tyr Lys Thr
        2780                2785                2790

Trp Ala Tyr His Gly Ser Tyr Glu Thr Lys Gln Thr Gly Ser Ala
        2795                2800                2805

Ser Ser Met Val Asn Gly Val Val Arg Leu Leu Thr Lys Pro Trp
        2810                2815                2820

Asp Val Val Pro Met Val Thr Gln Met Ala Met Thr Asp Thr Thr
        2825                2830                2835

Pro Phe Gly Gln Gln Arg Val Phe Lys Glu Lys Val Asp Thr Arg
        2840                2845                2850

Thr Gln Glu Pro Lys Glu Gly Thr Lys Lys Leu Met Lys Ile Thr
        2855                2860                2865
```

```
Ala Glu Trp Leu Trp Lys Glu Leu Gly Lys Lys Lys Thr Pro Arg
2870              2875              2880

Met Cys Thr Arg Glu Glu Phe Thr Arg Lys Val Arg Ser Asn Ala
2885              2890              2895

Ala Leu Gly Ala Ile Phe Thr Asp Glu Asn Lys Trp Lys Ser Ala
2900              2905              2910

Arg Glu Ala Val Glu Asp Ser Arg Phe Trp Glu Leu Val Asp Lys
2915              2920              2925

Glu Arg Asn Leu His Leu Glu Gly Lys Cys Glu Thr Cys Val Tyr
2930              2935              2940

Asn Met Met Gly Lys Arg Glu Lys Lys Leu Gly Glu Phe Gly Lys
2945              2950              2955

Ala Lys Gly Ser Arg Ala Ile Trp Tyr Met Trp Leu Gly Ala Arg
2960              2965              2970

Phe Leu Glu Phe Glu Ala Leu Gly Phe Leu Asn Glu Asp His Trp
2975              2980              2985

Phe Ser Arg Glu Asn Ser Leu Ser Gly Val Glu Gly Glu Gly Leu
2990              2995              3000

His Lys Leu Gly Tyr Ile Leu Arg Asp Val Ser Lys Lys Glu Gly
3005              3010              3015

Gly Ala Met Tyr Ala Asp Asp Thr Ala Gly Trp Asp Thr Arg Ile
3020              3025              3030

Thr Leu Glu Asp Leu Lys Asn Glu Glu Met Val Thr Asn His Met
3035              3040              3045

Glu Gly Glu His Lys Lys Leu Ala Glu Ala Ile Phe Lys Leu Thr
3050              3055              3060

Tyr Gln Asn Lys Val Val Arg Val Gln Arg Pro Thr Pro Arg Gly
3065              3070              3075

Thr Val Met Asp Ile Ile Ser Arg Arg Asp Gln Arg Gly Ser Gly
3080              3085              3090

Gln Val Gly Thr Tyr Gly Leu Asn Thr Phe Thr Asn Met Glu Ala
3095              3100              3105

Gln Leu Ile Arg Gln Met Glu Gly Glu Gly Val Phe Lys Asn Ile
3110              3115              3120

Gln His Leu Thr Val Thr Glu Glu Ile Ala Val Gln Asn Trp Leu
3125              3130              3135

Ala Arg Val Gly Arg Glu Arg Leu Ser Arg Met Ala Ile Ser Gly
3140              3145              3150

Asp Asp Cys Val Val Lys Pro Leu Asp Asp Arg Phe Ala Ser Ala
3155              3160              3165

Leu Thr Ala Leu Asn Asp Met Gly Lys Ile Arg Lys Asp Ile Gln
3170              3175              3180

Gln Trp Glu Pro Ser Arg Gly Trp Asn Asp Trp Thr Gln Val Pro
3185              3190              3195

Phe Cys Ser His His Phe His Glu Leu Ile Met Lys Asp Gly Arg
3200              3205              3210

Val Leu Val Val Pro Cys Arg Asn Gln Asp Glu Leu Ile Gly Arg
3215              3220              3225

Ala Arg Ile Ser Gln Gly Ala Gly Trp Ser Leu Arg Glu Thr Ala
3230              3235              3240

Cys Leu Gly Lys Ser Tyr Ala Gln Met Trp Ser Leu Met Tyr Phe
3245              3250              3255
```

```
His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390

<210> SEQ ID NO 15
<211> LENGTH: 3391
<212> TYPE: PRT
<213> ORGANISM: Artificial Sequence
<220> FEATURE:
<223> OTHER INFORMATION: chimeric dengue virus DENV2/4 EDII swap

<400> SEQUENCE: 15

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
                20                  25                  30

Phe Ser Leu Gly Met Leu Gln Gly Arg Gly Pro Leu Lys Leu Phe Met
            35                  40                  45

Ala Leu Val Ala Phe Leu Arg Phe Leu Thr Ile Pro Pro Thr Ala Gly
        50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
                100                 105                 110

Met Ala Phe His Leu Thr Thr Arg Asn Gly Glu Pro His Met Ile Val
            115                 120                 125

Ser Arg Gln Glu Lys Gly Lys Ser Leu Leu Phe Lys Thr Glu Asp Gly
        130                 135                 140

Val Asn Met Cys Thr Leu Met Ala Met Asp Leu Gly Glu Leu Cys Glu
145                 150                 155                 160

Asp Thr Ile Thr Tyr Asn Cys Pro Leu Leu Arg Gln Asn Glu Pro Glu
                165                 170                 175

Asp Ile Asp Cys Trp Cys Asn Ser Thr Ser Thr Trp Val Thr Tyr Gly
                180                 185                 190

Thr Cys Thr Thr Thr Gly Glu His Arg Arg Glu Lys Arg Ser Val Ala
            195                 200                 205

Leu Val Pro His Val Gly Met Gly Leu Glu Thr Arg Thr Glu Thr Trp
        210                 215                 220
```

-continued

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
            245                 250                 255

Thr Ile Gly Thr Thr His Phe Gln Arg Ala Leu Ile Phe Ile Leu Leu
        260                 265                 270

Thr Ala Val Ala Pro Ser Met Thr Met Arg Cys Ile Gly Ile Ser Asn
    275                 280                 285

Arg Asp Phe Val Glu Gly Val Ser Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Glu Val Ala Leu Leu
            325                 330                 335

Arg Thr Tyr Cys Ile Glu Ala Ser Ile Ser Asn Ile Thr Thr Ala Thr
        340                 345                 350

Arg Cys Pro Thr Gln Gly Glu Pro Tyr Leu Lys Glu Glu Gln Asp Gln
    355                 360                 365

Gln Tyr Ile Cys Arg Arg Asp Val Val Asp Arg Gly Trp Gly Asn Gly
370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Ile Glu Asn Leu Glu
            405                 410                 415

Tyr Thr Ile Val Val Thr Pro His Ser Gly Glu Glu His Ala Val Gly
        420                 425                 430

Asn Asp Thr Gly Lys His Gly Lys Glu Ile Lys Val Thr Pro Gln Ser
    435                 440                 445

Ser Ile Thr Glu Ala Glu Leu Thr Gly Tyr Gly Thr Val Thr Met Glu
450                 455                 460

Cys Ser Pro Arg Thr Gly Leu Asp Phe Asn Glu Met Ile Leu Met Lys
465                 470                 475                 480

Met Lys Lys Lys Thr Trp Leu Val His Lys Gln Trp Phe Leu Asp Leu
            485                 490                 495

Pro Leu Pro Trp Thr Ala Gly Ala Asp Thr Ser Glu Val His Trp Asn
        500                 505                 510

Tyr Lys Glu Arg Met Val Thr Phe Lys Val Pro His Ala Lys Arg Gln
    515                 520                 525

Asp Val Thr Val Leu Gly Ser Gln Glu Gly Ala Met His Ser Ala Leu
530                 535                 540

Ala Gly Ala Thr Glu Val Asp Ser Gly Asp Gly Asn His Met Phe Thr
545                 550                 555                 560

Gly His Leu Lys Cys Arg Leu Arg Met Asp Lys Leu Gln Leu Lys Gly
            565                 570                 575

Met Ser Tyr Ser Met Cys Thr Gly Lys Phe Lys Val Val Lys Glu Ile
        580                 585                 590

Ala Glu Thr Gln His Gly Thr Ile Val Ile Arg Val Gln Tyr Glu Gly
    595                 600                 605

Asp Gly Ser Pro Cys Lys Ile Pro Phe Glu Ile Met Asp Leu Glu Lys
610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser

```
                645                 650                 655
Tyr Ile Ile Ile Gly Val Asp Pro Gly Gln Leu Lys Leu Asn Trp Phe
            660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
            725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Ile Val Thr Leu Tyr
            755                 760                 765

Leu Gly Val Met Val Gln Ala Asp Ser Gly Cys Val Val Ser Trp Lys
            770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
            805                 810                 815

Leu Ala Ser Ala Ile Gln Lys Ala Gln Glu Glu Gly Ile Cys Gly Ile
            820                 825                 830

Arg Ser Val Thr Arg Leu Glu Asn Leu Met Trp Lys Gln Ile Thr Pro
            835                 840                 845

Glu Leu Asn His Ile Leu Ala Glu Asn Glu Val Lys Leu Thr Ile Met
850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
            915                 920                 925

Glu Val Glu Asp Tyr Gly Phe Gly Val Phe Thr Thr Asn Ile Trp Leu
            930                 935                 940

Lys Leu Lys Glu Lys Gln Asp Ala Phe Cys Asp Ser Lys Leu Met Ser
945                 950                 955                 960

Ala Ala Ile Lys Asp Asn Arg Ala Val His Ala Asp Met Gly Tyr Trp
            965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
            995                 1000                1005

Asn Gly Val Leu Glu Ser Glu Met Ile Ile Pro Lys Asn Leu Ala
            1010                1015                1020

Gly Pro Val Ser Gln His Asn Tyr Arg Pro Gly Tyr His Thr Gln
            1025                1030                1035

Ile Ala Gly Pro Trp His Leu Gly Lys Leu Glu Met Asp Phe Asp
            1040                1045                1050

Phe Cys Asp Gly Thr Thr Val Val Val Thr Glu Asp Cys Gly Asn
            1055                1060                1065
```

```
Arg Gly Pro Ser Leu Arg Thr Thr Ala Ser Gly Lys Leu Ile
1070            1075            1080

Thr Glu Trp Cys Cys Arg Ser Cys Thr Leu Pro Pro Leu Arg Tyr
1085            1090            1095

Arg Gly Glu Asp Gly Cys Trp Tyr Gly Met Glu Ile Arg Pro Leu
1100            1105            1110

Lys Glu Lys Glu Asn Leu Val Asn Ser Leu Val Thr Ala Gly
1115            1120            1125

His Gly Gln Val Asp Asn Phe Ser Leu Gly Val Leu Gly Met Ala
1130            1135            1140

Leu Phe Leu Glu Glu Met Leu Arg Thr Arg Val Gly Thr Lys His
1145            1150            1155

Ala Ile Leu Leu Val Ala Val Ser Phe Val Thr Leu Ile Thr Gly
1160            1165            1170

Asn Met Ser Phe Arg Asp Leu Gly Arg Val Val Met Val Gly
1175            1180            1185

Ala Thr Met Thr Asp Asp Ile Gly Met Gly Val Thr Tyr Leu Ala
1190            1195            1200

Leu Leu Ala Ala Phe Lys Val Arg Pro Thr Phe Ala Ala Gly Leu
1205            1210            1215

Leu Leu Arg Lys Leu Thr Ser Lys Glu Leu Met Met Thr Thr Ile
1220            1225            1230

Gly Ile Val Leu Leu Ser Gln Ser Thr Ile Pro Glu Thr Ile Leu
1235            1240            1245

Glu Leu Thr Asp Ala Leu Ala Leu Gly Met Met Val Leu Lys Met
1250            1255            1260

Val Arg Asn Met Glu Lys Tyr Gln Leu Ala Val Thr Ile Met Ala
1265            1270            1275

Ile Leu Cys Val Pro Asn Ala Val Ile Leu Gln Asn Ala Trp Lys
1280            1285            1290

Val Ser Cys Thr Ile Leu Ala Val Val Ser Val Ser Pro Leu Leu
1295            1300            1305

Leu Thr Ser Ser Gln Gln Lys Thr Asp Trp Ile Pro Leu Ala Leu
1310            1315            1320

Thr Ile Lys Gly Leu Asn Pro Thr Ala Ile Phe Leu Thr Thr Leu
1325            1330            1335

Ser Arg Thr Ser Lys Lys Arg Ser Trp Pro Leu Asn Glu Ala Ile
1340            1345            1350

Met Ala Val Gly Met Val Ser Ile Leu Ala Ser Ser Leu Leu Lys
1355            1360            1365

Asn Asp Ile Pro Met Thr Gly Pro Leu Val Ala Gly Gly Leu Leu
1370            1375            1380

Thr Val Cys Tyr Val Leu Thr Gly Arg Ser Ala Asp Leu Glu Leu
1385            1390            1395

Glu Arg Ala Ala Asp Val Lys Trp Glu Asp Gln Ala Glu Ile Ser
1400            1405            1410

Gly Ser Ser Pro Ile Leu Ser Ile Thr Ile Ser Glu Asp Gly Ser
1415            1420            1425

Met Ser Ile Lys Asn Glu Glu Glu Gln Thr Leu Thr Ile Leu
1430            1435            1440

Ile Arg Thr Gly Leu Leu Val Ile Ser Gly Leu Phe Pro Val Ser
1445            1450            1455
```

| | | | | | | | | | | |
|---|---|---|---|---|---|---|---|---|---|---|
|Ile|Pro|Ile|Thr|Ala|Ala|Ala|Trp|Tyr|Leu|Trp|Glu|Val|Lys|Lys|
|1460| | | | |1465| | | | |1470| | | | |

Ile Pro Ile Thr Ala Ala Ala Trp Tyr Leu Trp Glu Val Lys Lys
1460 1465 1470

Gln Arg Ala Gly Val Leu Trp Asp Val Pro Ser Pro Pro Pro Met
1475 1480 1485

Gly Lys Ala Glu Leu Glu Asp Gly Ala Tyr Arg Ile Lys Gln Lys
1490 1495 1500

Gly Ile Leu Gly Tyr Ser Gln Ile Gly Ala Gly Val Tyr Lys Glu
1505 1510 1515

Gly Thr Phe His Thr Met Trp His Val Thr Arg Gly Ala Val Leu
1520 1525 1530

Met His Lys Gly Lys Arg Ile Glu Pro Ser Trp Ala Asp Val Lys
1535 1540 1545

Lys Asp Leu Ile Ser Tyr Gly Gly Gly Trp Lys Leu Glu Gly Glu
1550 1555 1560

Trp Lys Glu Gly Glu Glu Val Gln Val Leu Ala Leu Glu Pro Gly
1565 1570 1575

Lys Asn Pro Arg Ala Val Gln Thr Lys Pro Gly Leu Phe Arg Thr
1580 1585 1590

Asn Ala Gly Thr Ile Gly Ala Val Ser Leu Asp Phe Ser Pro Gly
1595 1600 1605

Thr Ser Gly Ser Pro Ile Ile Asp Lys Lys Gly Lys Val Val Gly
1610 1615 1620

Leu Tyr Gly Asn Gly Val Val Thr Arg Ser Gly Ala Tyr Val Ser
1625 1630 1635

Ala Ile Ala Gln Thr Glu Lys Ser Ile Glu Asp Asn Pro Glu Ile
1640 1645 1650

Glu Asp Asp Ile Phe Arg Lys Arg Arg Leu Thr Ile Met Asp Leu
1655 1660 1665

His Pro Gly Ala Gly Lys Thr Lys Arg Tyr Leu Pro Ala Ile Val
1670 1675 1680

Arg Glu Ala Ile Lys Arg Gly Leu Arg Thr Leu Ile Leu Ala Pro
1685 1690 1695

Thr Arg Val Val Ala Ala Glu Met Glu Glu Ala Leu Arg Gly Leu
1700 1705 1710

Pro Ile Arg Tyr Gln Thr Pro Ala Ile Arg Ala Glu His Thr Gly
1715 1720 1725

Arg Glu Ile Val Asp Leu Met Cys His Ala Thr Phe Thr Met Arg
1730 1735 1740

Leu Leu Ser Pro Val Arg Val Pro Asn Tyr Asn Leu Ile Ile Met
1745 1750 1755

Asp Glu Ala His Phe Thr Asp Pro Ala Ser Ile Ala Ala Arg Gly
1760 1765 1770

Tyr Ile Ser Thr Arg Val Glu Met Gly Glu Ala Ala Gly Ile Phe
1775 1780 1785

Met Thr Ala Thr Pro Pro Gly Ser Arg Asp Pro Phe Pro Gln Ser
1790 1795 1800

Asn Ala Pro Ile Ile Asp Glu Glu Arg Glu Ile Pro Glu Arg Ser
1805 1810 1815

Trp Asn Ser Gly His Glu Trp Val Thr Asp Phe Lys Gly Lys Thr
1820 1825 1830

Val Trp Phe Val Pro Ser Ile Lys Ala Gly Asn Asp Ile Ala Ala
1835 1840 1845

Cys Leu Arg Lys Asn Gly Lys Lys Val Ile Gln Leu Ser Arg Lys

```
                    1850                1855                1860
Thr Phe Asp Ser Glu Tyr Val Lys Thr Arg Thr Asn Asp Trp Asp
    1865                1870                1875
Phe Val Val Thr Thr Asp Ile Ser Glu Met Gly Ala Asn Phe Lys
    1880                1885                1890
Ala Glu Arg Val Ile Asp Pro Arg Arg Cys Met Lys Pro Val Ile
    1895                1900                1905
Leu Thr Asp Gly Glu Glu Arg Val Ile Leu Ala Gly Pro Met Pro
    1910                1915                1920
Val Thr His Ser Ser Ala Ala Gln Arg Arg Gly Arg Ile Gly Arg
    1925                1930                1935
Asn Pro Lys Asn Glu Asn Asp Gln Tyr Ile Tyr Met Gly Glu Pro
    1940                1945                1950
Leu Glu Asn Asp Glu Asp Cys Ala His Trp Lys Glu Ala Lys Met
    1955                1960                1965
Leu Leu Asp Asn Ile Asn Thr Pro Glu Gly Ile Ile Pro Ser Met
    1970                1975                1980
Phe Glu Pro Glu Arg Glu Lys Val Asp Ala Ile Asp Gly Glu Tyr
    1985                1990                1995
Arg Leu Arg Gly Glu Ala Arg Lys Thr Phe Val Asp Leu Met Arg
    2000                2005                2010
Arg Gly Asp Leu Pro Val Trp Leu Ala Tyr Lys Val Ala Ala Glu
    2015                2020                2025
Gly Ile Asn Tyr Ala Asp Arg Arg Trp Cys Phe Asp Gly Ile Lys
    2030                2035                2040
Asn Asn Gln Ile Leu Glu Glu Asn Val Glu Val Glu Ile Trp Thr
    2045                2050                2055
Lys Glu Gly Glu Arg Lys Lys Leu Lys Pro Arg Trp Leu Asp Ala
    2060                2065                2070
Arg Ile Tyr Ser Asp Pro Leu Ala Leu Lys Glu Phe Lys Glu Phe
    2075                2080                2085
Ala Ala Gly Arg Lys Ser Leu Thr Leu Asn Leu Ile Thr Glu Met
    2090                2095                2100
Gly Arg Leu Pro Thr Phe Met Thr Gln Lys Ala Arg Asp Ala Leu
    2105                2110                2115
Asp Asn Leu Ala Val Leu His Thr Ala Glu Ala Gly Gly Arg Ala
    2120                2125                2130
Tyr Asn His Ala Leu Ser Glu Leu Pro Glu Thr Leu Glu Thr Leu
    2135                2140                2145
Leu Leu Leu Thr Leu Leu Ala Thr Val Thr Gly Gly Ile Phe Leu
    2150                2155                2160
Phe Leu Met Ser Gly Arg Gly Ile Gly Lys Met Thr Leu Gly Met
    2165                2170                2175
Cys Cys Ile Ile Thr Ala Ser Ile Leu Leu Trp Tyr Ala Gln Ile
    2180                2185                2190
Gln Pro His Trp Ile Ala Ala Ser Ile Ile Leu Glu Phe Phe Leu
    2195                2200                2205
Ile Val Leu Leu Ile Pro Glu Pro Glu Lys Gln Arg Thr Pro Gln
    2210                2215                2220
Asp Asn Gln Leu Thr Tyr Val Val Ile Ala Ile Leu Thr Val Val
    2225                2230                2235
Ala Ala Thr Met Ala Asn Glu Met Gly Phe Leu Glu Lys Thr Lys
    2240                2245                2250
```

```
Lys Asp Leu Gly Leu Gly Ser Ile Ala Thr Gln Gln Pro Glu Ser
    2255                2260                2265

Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Leu Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415

Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640
```

-continued

```
Asn Pro Thr Val Glu Ala Gly Arg Thr Leu Arg Val Leu Asn Leu
    2645                2650                2655

Val Glu Asn Trp Leu Asn Asn Thr Gln Phe Cys Ile Lys Val
    2660                2665                2670

Leu Asn Pro Tyr Met Pro Ser Val Ile Glu Lys Met Glu Thr Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg His Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
```

```
                3035                3040                3045
Glu Gly Glu His Lys Lys Leu Ala Glu Ala Ile Phe Lys Leu Thr
    3050                3055                3060
Tyr Gln Asn Lys Val Val Arg Val Gln Arg Pro Thr Pro Arg Gly
    3065                3070                3075
Thr Val Met Asp Ile Ile Ser Arg Arg Asp Gln Arg Gly Ser Gly
    3080                3085                3090
Gln Val Gly Thr Tyr Gly Leu Asn Thr Phe Thr Asn Met Glu Ala
    3095                3100                3105
Gln Leu Ile Arg Gln Met Glu Gly Glu Gly Val Phe Lys Asn Ile
    3110                3115                3120
Gln His Leu Thr Val Thr Glu Glu Ile Ala Val Gln Asn Trp Leu
    3125                3130                3135
Ala Arg Val Gly Arg Glu Arg Leu Ser Arg Met Ala Ile Ser Gly
    3140                3145                3150
Asp Asp Cys Val Val Lys Pro Leu Asp Asp Arg Phe Ala Ser Ala
    3155                3160                3165
Leu Thr Ala Leu Asn Asp Met Gly Lys Ile Arg Lys Asp Ile Gln
    3170                3175                3180
Gln Trp Glu Pro Ser Arg Gly Trp Asn Asp Trp Thr Gln Val Pro
    3185                3190                3195
Phe Cys Ser His His Phe His Glu Leu Ile Met Lys Asp Gly Arg
    3200                3205                3210
Val Leu Val Val Pro Cys Arg Asn Gln Asp Glu Leu Ile Gly Arg
    3215                3220                3225
Ala Arg Ile Ser Gln Gly Ala Gly Trp Ser Leu Arg Glu Thr Ala
    3230                3235                3240
Cys Leu Gly Lys Ser Tyr Ala Gln Met Trp Ser Leu Met Tyr Phe
    3245                3250                3255
His Arg Arg Asp Leu Arg Leu Ala Ala Asn Ala Ile Cys Ser Ala
    3260                3265                3270
Val Pro Ser His Trp Val Pro Thr Ser Arg Thr Thr Trp Ser Ile
    3275                3280                3285
His Ala Lys His Glu Trp Met Thr Thr Glu Asp Met Leu Thr Val
    3290                3295                3300
Trp Asn Arg Val Trp Ile Gln Glu Asn Pro Trp Met Glu Asp Lys
    3305                3310                3315
Thr Pro Val Glu Ser Trp Glu Ile Pro Tyr Leu Gly Lys Arg
    3320                3325                3330
Glu Asp Gln Trp Cys Gly Ser Leu Ile Gly Leu Thr Ser Arg Ala
    3335                3340                3345
Thr Trp Ala Lys Asn Ile Gln Ala Ala Ile Asn Gln Val Arg Ser
    3350                3355                3360
Leu Ile Gly Asn Glu Glu Tyr Thr Asp Tyr Met Pro Ser Met Lys
    3365                3370                3375
Arg Phe Arg Arg Glu Glu Glu Ala Gly Val Leu Trp
    3380                3385                3390

<210> SEQ ID NO 16
<211> LENGTH: 394
<212> TYPE: PRT
<213> ORGANISM: Dengue virus type 1

<400> SEQUENCE: 16
```

Met Arg Cys Val Gly Ile Gly Asn Arg Asp Phe Val Glu Gly Leu Ser
1               5                   10                  15

Gly Ala Thr Trp Val Asp Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Glu Lys Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys
385                 390

<210> SEQ ID NO 17
<211> LENGTH: 394
<212> TYPE: PRT

<213> ORGANISM: Dengue virus type 2

<400> SEQUENCE: 17

Met Arg Cys Ile Gly Ile Ser Asn Arg Asp Phe Val

```
<210> SEQ ID NO 18
<211> LENGTH: 392
<212> TYPE: PRT
<213> ORGANISM: Dengue virus type 3

<400> SEQUENCE: 18

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Asn Ala
    370                 375                 380
```

Leu Lys Ile Asn Trp Tyr Lys Lys
385                 390

<210> SEQ ID NO 19
<211> LENGTH: 394
<212> TYPE: PRT
<213> ORGANISM: Dengue virus type 4

<400> SEQUENCE: 19

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
            340                 345                 350

Ser Ser Thr Pro Leu Ala Glu Asn Thr Asn Ser Val Thr Asn Ile Glu

```
                355                 360                 365
Leu Glu Pro Pro Phe Gly Asp Ser Tyr Ile Val Ile Gly Val Gly Asn
370                 375                 380

Ser Ala Leu Thr Leu His Trp Phe Arg Lys
385                 390

<210> SEQ ID NO 20
<211> LENGTH: 410
<212> TYPE: PRT
<213> ORGANISM: Yellow fever virus

<400> SEQUENCE: 20

Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Arg Pro Ala Glu Val Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125

Glu Val Asp Gln Thr Lys Ile Gln Tyr Val Ile Arg Ala Gln Leu His
    130                 135                 140

Val Gly Ala Lys Gln Glu Asn Trp Thr Thr Asp Ile Lys Thr Leu Lys
145                 150                 155                 160

Phe Asp Ala Leu Ser Gly Ser Gln Glu Val Glu Phe Ile Gly Tyr Gly
                165                 170                 175

Lys Ala Thr Leu Glu Cys Gln Val Gln Thr Ala Val Asp Phe Gly Asn
            180                 185                 190

Ser Tyr Ile Ala Glu Met Glu Thr Glu Ser Trp Ile Val Asp Arg Gln
        195                 200                 205

Trp Ala Gln Asp Leu Thr Leu Pro Trp Gln Ser Gly Ser Gly Gly Val
    210                 215                 220

Trp Arg Glu Met His His Leu Val Glu Phe Glu Pro Pro His Ala Ala
225                 230                 235                 240

Thr Ile Arg Val Leu Ala Leu Gly Asn Gln Glu Gly Ser Leu Lys Thr
                245                 250                 255

Ala Leu Thr Gly Ala Met Arg Val Thr Lys Asp Thr Asn Asp Asn Asn
            260                 265                 270

Leu Tyr Lys Leu His Gly Gly His Val Ser Cys Arg Val Lys Leu Ser
        275                 280                 285

Ala Leu Thr Leu Lys Gly Thr Ser Tyr Lys Ile Cys Thr Asp Lys Met
    290                 295                 300

Phe Phe Val Lys Asn Pro Thr Asp Thr Gly His Gly Thr Val Val Met
305                 310                 315                 320

Gln Val Lys Val Ser Lys Gly Ala Pro Cys Arg Ile Pro Val Ile Val
                325                 330                 335
```

```
Ala Asp Asp Leu Thr Ala Ala Ile Asn Lys Gly Ile Leu Val Thr Val
                340                 345                 350

Asn Pro Ile Ala Ser Thr Asn Asp Glu Val Leu Ile Glu Val Asn
            355                 360                 365

Pro Pro Phe Gly Asp Ser Tyr Ile Ile Val Gly Arg Gly Asp Ser Arg
        370                 375                 380

Leu Thr Tyr Gln Trp His Lys Glu Gly Ser Ser Ile Gly Lys Leu Phe
385                 390                 395                 400

Thr Gln Thr Met Lys Gly Val Glu Arg Leu
                405                 410

<210> SEQ ID NO 21
<211> LENGTH: 410
<212> TYPE: PRT
<213> ORGANISM: Japanese encephalitis virus

<400> SEQUENCE: 21

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
                20                  25                  30

Ile Met Ala Asn Asp Lys Pro Thr Leu Asp Val Arg Met Ile Asn Ile
            35                  40                  45

Glu Ala Ser Gln Leu Ala Glu Val Arg Ser Tyr Cys Tyr His Ala Ser
50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
290                 295                 300
```

```
Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
                355                 360                 365

Lys Val Leu Val Glu Met Glu Pro Pro Phe Gly Asp Ser Tyr Ile Val
            370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr
                405                 410

<210> SEQ ID NO 22
<211> LENGTH: 394
<212> TYPE: PRT
<213> ORGANISM: Artificial Sequence
<220> FEATURE:
<223> OTHER INFORMATION: E protein for DENV2/4 M14+ hinge with tissue
      culture adaption

<400> SEQUENCE: 22

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Thr Lys Thr
            35                  40                  45

Thr Ala Lys Glu Val Ala Leu Leu Arg Thr Tyr Cys Ile Glu Ala Lys
        50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Lys Phe Ser Cys Ser Gly Lys Ile Thr Gly Asn
        115                 120                 125

Leu Val Gln Ile Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Ser Gly Ile Asp
            180                 185                 190

Phe Asn Glu Met Val Leu Leu Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Asp Lys Glu Thr Leu Val Thr Phe
225                 230                 235                 240

Lys Asn Pro His Ala Lys Lys Gln Asp Val Val Val Leu Gly Ser Gln
```

```
                        245                 250                 255
Glu Gly Ala Met His Thr Ala Leu Thr Gly Ala Thr Glu Val Asp Ser
                    260                 265                 270
Gly Asp Gly Asn His Met Phe Ala Gly His Leu Lys Cys Arg Leu Arg
                275                 280                 285
Met Asp Lys Leu Gln Leu Lys Gly Met Ser Tyr Ser Met Cys Thr Gly
            290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Met Asp Leu Glu Lys Arg His Val Leu Gly Arg Leu Ile
                340                 345                 350
Thr Val Asn Pro Ile Val Thr Glu Lys Asp Ser Pro Val Asn Ile Glu
            355                 360                 365
Ala Glu Pro Pro Phe Gly Asp Ser Tyr Ile Ile Gly Val Asp Pro
        370                 375                 380
Gly Gln Leu Lys Leu Asn Trp Phe Lys Lys
385                 390

<210> SEQ ID NO 23
<211> LENGTH: 166
<212> TYPE: PRT
<213> ORGANISM: Artificial Sequence
<220> FEATURE:
<223> OTHER INFORMATION: prM protein for DENV2/4+ hinge with tissue
      culture adaption

<400> SEQUENCE: 23

Phe His Leu Thr Thr Arg Asn Gly Glu Pro His Met Ile Val Ser Arg
1               5                   10                  15
Gln Glu Lys Gly Lys Ser Leu Leu Phe Lys Thr Glu Asp Gly Val Asn
                20                  25                  30
Met Cys Thr Leu Met Ala Met Asp Leu Gly Glu Leu Cys Glu Asp Thr
            35                  40                  45
Ile Thr Tyr Asn Cys Pro Leu Leu Arg Gln Asn Glu Pro Glu Asp Ile
        50                  55                  60
Asp Cys Trp Cys Asn Ser Thr Ser Thr Trp Val Thr Tyr Gly Thr Cys
65                  70                  75                  80
Thr Thr Thr Gly Glu His Arg Arg Glu Lys Arg Ser Val Ala Leu Val
                85                  90                  95
Thr His Val Gly Met Gly Leu Glu Thr Arg Thr Glu Thr Trp Met Ser
            100                 105                 110
Ser Glu Gly Ala Trp Lys His Ala Gln Arg Ile Glu Thr Trp Ile Leu
        115                 120                 125
Arg His Pro Gly Phe Thr Ile Met Ala Ala Ile Leu Ala Tyr Thr Ile
    130                 135                 140
Gly Thr Thr His Phe Gln Arg Ala Leu Ile Phe Ile Leu Leu Thr Ala
145                 150                 155                 160
Val Ala Pro Ser Met Thr
                165

<210> SEQ ID NO 24
<211> LENGTH: 394
<212> TYPE: PRT
<213> ORGANISM: Artificial Sequence
<220> FEATURE:
```

<223> OTHER INFORMATION: chimeric dengue virus E glycoprotein DENV2/
    4-Complete Modified Swap

<400> SEQUENCE: 24

```
Met Arg Cys Ile Gly Ile Ser Asn Arg Asp Phe Val Glu Gly Val Ser
1               5                   10                  15
Gly Gly Ser Trp Val Asp Ile Val Leu Glu His Gly Ser Cys Val Thr
            20                  25                  30
Thr Met Ala Lys Asn Lys Pro Thr Leu Asp Phe Glu Leu Thr Lys Thr
        35                  40                  45
Thr Ala Lys Glu Val Ala Leu Leu Arg Thr Tyr Cys Ile Glu Ala Lys
50                  55                  60
Ile Ser Asn Ile Thr Thr Glu Ser Arg Cys Pro Thr Gln Gly Glu Pro
65                  70                  75                  80
Tyr Leu Lys Glu Glu Gln Asp Gln Gln Tyr Ile Cys Lys His Ser Met
                85                  90                  95
Val Asp Arg Gly Trp Gly Asn Gly Cys Gly Leu Phe Gly Lys Gly Gly
            100                 105                 110
Ile Val Thr Cys Ala Lys Phe Ser Cys Ser Gly Lys Ile Thr Gly Asn
        115                 120                 125
Leu Val Gln Pro Glu Asn Leu Glu Tyr Thr Ile Val Val Thr Pro His
130                 135                 140
Ser Gly Glu Glu His Ala Val Gly Asn Asp Thr Gly Lys His Gly Lys
145                 150                 155                 160
Glu Ile Lys Val Thr Pro Gln Ser Ser Ile Thr Glu Ala Glu Leu Thr
                165                 170                 175
Gly Tyr Gly Thr Val Thr Met Glu Cys Ser Pro Arg Thr Gly Leu Asp
            180                 185                 190
Phe Asn Glu Met Val Leu Leu Lys Met Lys Lys Thr Trp Leu Val
        195                 200                 205
His Lys Gln Trp Phe Leu Asp Leu Pro Leu Pro Trp Thr Ala Gly Ala
210                 215                 220
Asp Thr Ser Glu Val His Trp Asn Tyr Lys Glu Thr Leu Val Thr Phe
225                 230                 235                 240
Lys Asn Pro His Ala Lys Lys Gln Asp Val Thr Val Leu Gly Ser Gln
                245                 250                 255
Glu Gly Ala Met His Thr Ala Leu Thr Gly Ala Thr Glu Val Asp Ser
            260                 265                 270
Gly Asp Gly Asn His Met Phe Ala Gly His Leu Lys Cys Arg Leu Arg
        275                 280                 285
Met Asp Lys Leu Gln Leu Lys Gly Met Ser Tyr Ser Met Cys Thr Gly
290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Met Asp Leu Glu Lys Arg His Val Leu Gly Arg Leu Ile
            340                 345                 350
Thr Val Asn Pro Ile Val Thr Glu Lys Asp Ser Pro Val Asn Ile Glu
        355                 360                 365
Ala Glu Pro Pro Phe Gly Asp Ser Tyr Ile Ile Ile Gly Val Asp Pro
370                 375                 380
Gly Gln Leu Lys Leu Asn Trp Phe Lys Lys
385                 390
```

<210> SEQ ID NO 25
<211> LENGTH: 394
<212> TYPE: PRT
<213> ORGANISM: Artificial Sequence
<220> FEATURE:
<223> OTHER INFORMATION: chimeric dengue virus E glycoprotein DENV2/
      4 EDII Swap

<400> SEQUENCE: 25

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu

```
             355                 360                 365
Ala Glu Pro Pro Phe Gly Asp Ser Tyr Ile Ile Ile Gly Val Asp Pro
    370                 375                 380

Gly Gln Leu Lys Leu Asn Trp Phe Lys Lys
385                 390
```

UNITED STATES PATENT AND TRADEMARK OFFICE
CERTIFICATE OF CORRECTION

PATENT NO. : 11,241,491 B2
APPLICATION NO. : 16/615350
DATED : February 8, 2022
INVENTOR(S) : Baric et al.

Page 1 of 3

It is certified that error appears in the above-identified patent and that said Letters Patent is hereby corrected as shown below:

In the Specification

Column 4, Line 33:
Please correct "(DEN V3/4 M-Complete)" to read -- (DENV3/4 M-Complete) --

Column 4, Line 51:
Please correct "(DENV2/4 M14/)" to read -- (DENV2/4 M14+) --

In the Claims

Column 139, Line 30 – Column 140, Line 42, Claim 1:
Please correct:

"(SEQ ID NO:9)
MRCIGISNRDFVEGVSGGSWVDIVLEHGSCVTTMAKNKPTLDFELIKTEAKEVALLRTY
CIEAKLTNTTTESRCPTQGEPSLNEEQDKRFVCKHSMVDRGWGNGCGLFGKGGIVTCA
KFSCSGKITGNLVQPENLEYTIVVTPHSGEEHAVGNDTGKHGKEIKVTPQSSITEAELTG
YGTVTMECSPRTGLDFNEMVLLKMKKKTWLVHKQWFLDLPLPWTAGADTSEVHWNY
KETLVTFKNPHAKKQDVVVLGSQEGAMHTALTGATEVDSGDGNHMFAGHLKCRLRM
DKLQLKGMSYSMCTGKFKVVKEIAETQHGTIVIRVQYEGDGSPCKIPFEIMDLEKRHVL
GRLITVNPIVTEKDSPVNIEAEPPFGDSYIIIGVDPGQLKLNWFKK;

(SEQ ID NO:10)
MRCIGISNRDFVEGVSGGSWVDIVLEHGSCVTTMAKNKPTLDFELTKTTAKEVALLRTY
CIEASISNITTASRCPTQGEPYLKEEQDQQYICKHSMVDRGWGNGCGLFGKGGIVTCAK
FSCSGKITGNLVQPENLEYTIVVTPHSGEEHAVGNDTGKHGKEIKVTPQSSITEAELTGY
GTVTMECSPRTGLDFNEMVLLKMKKKTWLVHKQWFLDLPLPWTAGADTSEVHWNYK
ETLVTFKNPHAKRQDVTVLGSQEGAMHTALTGATEVDSGDGNHMFAGHLKCRLRMD
KLQLKGMSYSMCTGKFKVVKEIAETQHGTIVIRVQYEGDGSPCKIPFEIMDLEKRHVLG
RLITVNPIVTEKDSPVNIEAEPPFGDSYIIIGVDPGQLKLNWFKK;

Signed and Sealed this
Twenty-first Day of June, 2022

Katherine Kelly Vidal
*Director of the United States Patent and Trademark Office*

(SEQ ID NO:22)

MRCIGISNRDFVEGVSGGSWVDIVLEHGSCVTTMAKNKPTLDFELTKTTAKEVALLRTY
CIEAKLTNTTTESRCPTQGEPSLNEEQDKRFVCKHSMVDRGWGNGCGLFGKGGIVTCA
KFSCSGKITGNLVQIENLEYTIVVTPHSGEEHAVGNDTGKHGKEIKVTPOSSITEAELTGY
GTVTMECSPRSGIDFNEMVLLKMKKKTWLVHKQWFLDLPLPWTAGADTSEVHWNDK
ETLVTFKNPHAKKQDVVVLGSQEGAMHTALTGATEVDSGDGNHMFAGHLKCRLRMD
KLQLKGMSYSMCTGKFKVVKEIAETQHGTIVIRVQYEGDGSPCKIPFEIMDLEKRHVLG
RLITVNPIVTEKDSPVNIEAEPPFGDSYIIGVDPGQLKLNWFKK.

(SEQ ID NO:24)

MRCIGISNRDFVEGVSGGSWVDIVLEHGSCVTTMAKNKPTLDFELTKTTAKEVALLRTY
CIEAKISNITTESRCPTQGEPYLKEEQDQQYICKHSMVDRGWGNGCGLFGKGGIVTCAK
FSCSGKITGNLVQPENLEYTIVVTPHSGEEHAVGNDTGKHGKEIKVTPQSSITEAELTGY
GTVTMECSPRTGLDFNEMVLLKMKKKTWLVHKQWFLDLPLPWTAGADTSEVHWNYK
ETLVTFKNPHAKKQDVTVLGSQEGAMHTALTGATEVDSGDGNHMFAGHLKCRLRMD
KLQLKGMSYSMCTGKFKVVKEIAETQHGTIVIRVQYEGDGSPCKIPFEIMDLEKRHVLG
RLITVNPIVTEKDSPVNIEAEPPFGDSYIIGVDPGQLKLNWFKK;

(SEQ ID NO:25)
MRCIGISNRDFVEGVSGGSWVDIVLEHGSCVTTMAKNKPTLDFELIKTEAKEVALLRT
YCIEASISNITTATRCPTQGEPYLKEEQDQQYICRRDVVDRGWGNGCGLFGKGGVVT
CAKFSCSGKITGNLVQIENLEYTIVVTPHSGEEHAVGNDTGKHGKEIKVTPQSSITEAE
LTGYGTVTMECSPRTGLDFNEMILMKMKKKTWLVHKQWFLDLPLPWTAGADTSEV
HWNYKERMVTFKVPHAKRQDVTVLGSQEGAMHSALAGATEVDSGDGNHMFTGHL
KCRLRMDKLQLKGMSYSMCTGKFKVVKEIAETQHGTIVIRVQYEGDGSPCKIPFEIM
DLEKRHVLGRLITVNPIVTEKDSPVNIEAEPPFGDSYIIGVDPGQLKLNWFKK;",

To read:
-- MRCIGISNRDFVEGVSGGSWVDIVLEHGSCVTTMAKNKPTLDFELIKTEAKEVALLRTY
CIEAKLTNTTTESRCPTQGEPSLNEEQDKRFVCKHSMVDRGWGNGCGLFGKGGIVTCA
KFSCSGKITGNLVQPENLEYTIVVTPHSGEEHAVGNDTGKHGKEIKVTPQSSITEAELTG
YGTVTMECSPRTGLDFNEMVLLKMKKKTWLVHKQWFLDLPLPWTAGADTSEVHWNY
KETLVTFKNPHAKKQDVVVLGSQEGAMHTALTGATEVDSGDGNHMFAGHLKCRLRM
DKLQLKGMSYSMCTGKFKVVKEIAETQHGTIVIRVQYEGDGSPCKIPFEIMDLEKRHVL
GRLITVNPIVTEKDSPVNIEAEPPFGDSYIIGVDPGQLKLNWFKK (SEQ ID NO:9);

MRCIGISNRDFVEGVSGGSWVDIVLEHGSCVTTMAKNKPTLDFELTKTTAKEVALLRTY
CIEASISNITTASRCPTQGEPYLKEEQDQQYICKHSMVDRGWGNGCGLFGKGGIVTCAK
FSCSGKITGNLVQPENLEYTIVVTPHSGEEHAVGNDTGKHGKEIKVTPQSSITEAELTGY
GTVTMECSPRTGLDFNEMVLLKMKKKTWLVHKQWFLDLPLPWTAGADTSEVHWNYK
ETLVTFKNPHAKRQDVTVLGSQEGAMHTALTGATEVDSGDGNHMFAGHLKCRLRMD
KLQLKGMSYSMCTGKFKVVKEIAETQHGTIVIRVQYEGDGSPCKIPFEIMDLEKRHVLG
RLITVNPIVTEKDSPVNIEAEPPFGDSYIIGVDPGQLKLNWFKK (SEQ ID NO:10);

MRCIGISNRDFVEGVSGGSWVDIVLEHGSCVTTMAKNKPTLDFELTKTTAKEVALLRTY
CIEAKLTNTTTESRCPTQGEPSLNEEQDKRFVCKHSMVDRGWGNGCGLFGKGGIVTCA
KFSCSGKITGNLVQIENLEYTIVVTPHSGEEHAVGNDTGKHGKEIKVTPQSSITEAELTGY
GTVTMECSPRSGIDFNEMVLLKMKKKTWLVHKQWFLDLPLPWTAGADTSEVHWNDK
ETLVTFKNPHAKKQDVVVLGSQEGAMHTALTGATEVDSGDGNHMFAGHLKCRLRMD
KLQLKGMSYSMCTGKFKVVKEIAETQHGTIVIRVQYEGDGSPCKIPFEIMDLEKRHVLG
RLITVNPIVTEKDSPVNIEAEPPFGDSYIIIGVDPGQLKLNWFKK (SEQ ID NO:22);

MRCIGISNRDFVEGVSGGSWVDIVLEHGSCVTTMAKNKPTLDFELTKTTAKEVALLRTY
CIEAKISNITTESRCPTQGEPYLKEEQDQQYICKHSMVDRGWGNGCGLFGKGGIVTCAK
FSCSGKITGNLVQPENLEYTIVVTPHSGEEHAVGNDTGKHGKEIKVTPQSSITEAELTGY
GTVTMECSPRTGLDFNEMVLLKMKKKTWLVHKQWFLDLPLPWTAGADTSEVHWNYK
ETLVTFKNPHAKKQDVTVLGSQEGAMHTALTGATEVDSGDGNHMFAGHLKCRLRMD
KLQLKGMSYSMCTGKFKVVKEIAETQHGTIVIRVQYEGDGSPCKIPFEIMDLEKRHVLG
RLITVNPIVTEKDSPVNIEAEPPFGDSYIIIGVDPGQLKLNWFKK (SEQ ID NO:24);

MRCIGISNRDFVEGVSGGSWVDIVLEHGSCVTTMAKNKPTLDFELIKTEAKEVALLRT
YCIEASISNITTATRCPTQGEPYLKEEQDQQYICRRDVVDRGWGNGCGLFGKGGVVT
CAKFSCSGKITGNLVQIENLEYTIVVTPHSGEEHAVGNDTGKHGKEIKVTPQSSITEAE
LTGYGTVTMECSPRTGLDFNEMILMKMKKKTWLVHKQWFLDLPLPWTAGADTSEV
HWNYKERMVTFKVPHAKRQDVTVLGSQEGAMHSALAGATEVDSGDGNHMFTGHL
KCRLRMDKLQLKGMSYSMCTGKFKVVKEIAETQHGTIVIRVQYEGDGSPCKIPFEIM
DLEKRHVLGRLITVNPIVTEKDSPVNIEAEPPFGDSYIIIGVDPGQLKLNWFKK **(SEQ
ID NO:25)**;